US007449190B2

(12) United States Patent
Nabel et al.

(10) Patent No.: US 7,449,190 B2
(45) Date of Patent: Nov. 11, 2008

(54) ASSAYS FOR ASSEMBLY OF EBOLA VIRUS NUCLEOCAPSIDS

(75) Inventors: Gary Nabel, Washington, DC (US); Yue Huang, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 345 days.

(21) Appl. No.: 11/031,921

(22) Filed: Jan. 7, 2005

(65) Prior Publication Data

US 2005/0180993 A1    Aug. 18, 2005

Related U.S. Application Data

(63) Continuation of application No. PCT/US03/21757, filed on Jul. 11, 2003.

(60) Provisional application No. 60/451,317, filed on Feb. 28, 2003, provisional application No. 60/395,876, filed on Jul. 12, 2002.

(51) Int. Cl.
*A61K 39/00*       (2006.01)
(52) U.S. Cl. .................................. 424/204.1
(58) Field of Classification Search ........................ None
See application file for complete search history.

(56) References Cited

U.S. PATENT DOCUMENTS

| 4,722,840 | A | 2/1988 | Valenzuela et al. |
| 5,679,342 | A | 10/1997 | Houghton et al. |
| 6,200,577 | B1 | 3/2001 | McLaughlan et al. |
| 2004/0057967 | A1 * | 3/2004 | Bavari et al. ............. 424/204.1 |

FOREIGN PATENT DOCUMENTS

| WO | WO 95/32310 | 11/1995 |
| WO | WO 00/09158 A1 | 2/2000 |

OTHER PUBLICATIONS

Reed et al., Status and challenges of filovirus vaccines, Vaccine 25 (2007) 1923-1934.*
Warfield et al., Filovirus-like particles as vaccines and discovery tools, Expert Rev Vaccines, 2005, 4(3):429-440.*
Aoki, K. et al. 1999 "Efficient generation of recombinant adenoviral vectors by cre-lox recombination in vitro." *Mol. Med.* 5:224-231.
Becker, S. et al. 1994 "The nucleoprotein of marburg virus is phosphorylated." *J. Gen. Virol.* 75:809-818.
Becker, S. et al. 1998 "Interactions of marburg virus nucleocapsid proteins." *Virology* 249:406-417.
Chen, C. et al. 1987 "High-efficiency transformation of mammalian cells by plasmid DNA." *Mol. Cell. Biol.* 7:2745-2752.
Delchambre, M. et al. 1989 "The gag precursor of simian immunodeficiency virus assembles into virus-like particles." *EMBO J.* 8:2653-2660.

Dessen, A. et al. 2000 "Crystal structure of the matrix protein VP40 from ebola virus." *EMBO J.* 19:4228-4236.
Elliott, L.H. et al. 1985 "Descriptive analysis of ebola virus proteins." *Virology* 147:169-176.
Feldmann, H. et al. 1992 "Marburg virus, a filovirus: messenger RNAs, gene order, and regulatory elements of the replication cycle." *Virus Res.* 24:1-19.
Feldmann, H. et al. 1996 "Filovirus-induced endothelial leakage triggered by infected monocytes/macrophages." *J. Virol.* 70:2208-2214.
Feldmann, H. et al. 1996 "Marburg and ebola viruses." *Adv. Virus Res.* 47:1-52.
Feldmann, H. et al. 1999 "Classification, structure, and replication of filoviruses." *Curr. Top. Microbiol. Immunol.* 235:1-21.
Feldmann, H. et al. 2001 "Biosynthesis and role of filoviral glycoproteins." *J. Gen. Virol.* 82:2839-2848.
Friborg, J. Jr. et al. 1999 "p53 inhibition by the LANA protein of KSHV protects against cell death." *Nature* 402:889-894.
Garoff, H. et al 1998. "Virus maturation by budding." *Microbiol. Molec. Biol. Rev.* 62:1171-1190.
Geisbert, T.W. et al. 1992 "Association of ebola-related reston virus particles and antigen with tissue lesions of monkeys imported to the United States." *J. Compar. Pathol.* 106:137-152.
Geisbert, T.W. et al. 1995 "Differentiation in filoviruses by electron microscopy." *Virus Res.* 39:129-150.
Gheysen, D. et al. 1989 "Assembly and release of HIV-1 precursor Pr55$^{gag}$ virus-like particles from recombinant baculovirus-infected insect cells." *Cell* 59:103-112.
Han, I. et al. 1997 "Reduced O glycosylation of Sp1 is associated with increased proteasome susceptibility." *Mol. Cell. Biol.* 17:2550-2558.
Hanover, J.A. 2001 "Glycan-dependent signaling: O-linked N-acetylglucosamine." *FASEB J.* 15:1865-1876.
Horikami, S.M. et al. 1992 "Complexes of sendai virus NP-P and P-L proteins are required for defective interfering particle genome replication in vitro." *J. Virol.* 66:4901-4908.

(Continued)

*Primary Examiner*—Bruce Campell
*Assistant Examiner*—Nicole Kinsey White
(74) *Attorney, Agent, or Firm*—Knobbe Martens Olson & Bear LLP

(57) ABSTRACT

The present invention relates to assays for the identification of compounds that inhibit assembly of NP, VP35, and VP24, or inhibit the glycosylation of NP, required for nucleocapsid formation, for use as anti-viral agents. The invention also relates to assays for the identification of compounds that block glycosylation of proteins having a glycosylation domain that is substantially homologous to a glycosylation domain of NP required for polymerization. The invention further relates to pseudoparticles for presentation of antigens or antigenic epitopes for immunogenic or vaccination purposes.

10 Claims, 51 Drawing Sheets

OTHER PUBLICATIONS

Huang, Y. et al. 2001 "Human immunodeficiency virus type 1-specific immunity after genetic immunization is enhanced by modification of Gag and Pol expression." *J. Virol.* 75:4947-4951.

Huang, Y. et al. 2002 "The assembly of Ebola virus nucleocapsid requires virion-associated proteins 35 and 24 and posttranslational modification of nucleoprotein." *Mol. Cell* 10:307-316.

Huber, M. et al. 1991 "Measles virus phosphoprotein retains the nucleocapsid protein in the cytoplasm." *Virology* 185:299-308.

Jasenosky, L.D. et al. 2001 "Ebola virus VP40-induced particle formation and association with the lipid bilayer." *J. Virol.* 75:5205-5214.

Kiley, M.P. et al. 1988 "Physicochemical properties of marburg virus: evidence for three distinct virus strains and their relationship to ebola virus." *J. Gen. Virol.* 69:1956-1967.

Le Guenno, B. et al. 1995 "Isolation and partial characterisation of a new strain of ebola virus." *Lancet* 345:1271-1274.

Lowe, J.B. 2001 "Glycosylation, immunity, and autoimmunity." *Cell* 104:809-812.

Luo, L. et al. 1994 "Mapping of functional domains for HIV-2 gag assembly into virus-like particles." *Virology* 205:496-502.

Martin-Serrano, J. et al. 2001 "HIV-1 and ebola virus encode small peptide motifs that recruit Tsg101 to sites of particle assembly to facilitate egress." *Nat. Med.* 7:1313-1319.

Maruyama, T. et al. 1999 "Ebola virus can be effectively neutralized by antibody produced in natural human infection." *J. Virol.* 73:6024-6030.

Moody, A.M. et al. 2001 "Developmentally regulated glycosylation of the CD8αβ coreceptor stalk modulates ligand binding." *Cell* 107:501-512.

Muhlberger, E. et al. 1998 "Three of the four nucleocapsid proteins of marburg virus, NP, VP35, and L, are sufficient to mediate replication and transcription of marburg virus-specific monocistronic minigenomes." *J. Virol.* 72:8756-8764.

Muhlberger, E. et al. 1999 "Comparison of the transcription and replication strategies of marburg virus and ebola virus by using artificial replication systems." *J. Virol.* 73:2333-2342.

Roquemore, E.P. et al. 1994 "Detection of O-linked N-acetylglucosamine (O-GlcNAc) on cytoplasmic and nuclear proteins." *Meth. Enzymol.* 230:443-460.

Ruigrok, R.W. et al. 2000 "Structural characterization and membrane binding properties of the matrix protein VP40 of ebola virus." *J. Mol. Biol.* 300:103-112.

Sanchez, A. et al. 1993 "Sequence analysis of the ebola virus genome: organization, genetic elements, and comparison with the genome of marburg virus." *Virus Res.* 29:215-240.

Schnittler, H-J. et al. 1993 "Replication of marburg virus in human endothelial cells: a possible mechanism for the development of viral hemorrhagic disease." *J. Clin. Invest.* 91:1301-1309.

Schwemmle, M. et al. 1998 "Interactions of the borna disease virus P, N, and X proteins and their functional implications." *J. Biol. Chem.* 273:9007-9012.

Smith, A.J. et al. 1993 "Requirements for incorporation of Pr160$^{gag-pol}$ from human immunodeficiency virus type 1 into virus-like particles." *J. Virol.* 67:2266-2275.

Starr, C.M. et al. 1990 "Glycosylation of nuclear pore protein p62. Reticulocyte lysate catalyzes O-linked N-acetylglucosamine addition in vitro." *J. Biol. Chem.* 265:6868-6873.

Sullivan, N.J. et al. 2000 "Development of a preventive vaccine for ebola virus infection in primates." *Nature* 408:605-609.

Timmins, J. et al. 2001 "Vesicular release of ebola virus matrix protein VP40." *Virology* 283:1-6.

Tooze, J. et al. 1988 "Site of addition of N-Acetyl-galactosamine to the E1 glycoprotein of mouse hepatitis virus-A59." *J. Cell Biol.* 106:1475-1487.

Volchkov, V.E. et al. 2001 "Recovery of infectious ebola virus from complementary DNA: RNA editing of the GP gene and viral cytotoxicity." *Science* 291:1965-1969.

Wells, L. et al. 2001 "Glycosylation of nucleocytoplasmic proteins: signal transduction and O-GlcNAc." *Science* 291:2376-2378.

Wills, J.W. et al. 1989 "Creation and expression of myristylated forms of rous sarcoma virus gag protein in mammalian cells." *J. Virol.* 63:4331-4343.

Yang, Z.-Y. et al. 1998 "Ebola virus, neutrophils, and antibody specificity (technical comment)." *Science* 282:845a in 4 pages.

Yang, Z.-Y. et al. 2000 "Identification of the ebola virus glycoprotein as the main viral determinant of vascular cell cytotoxicity and injury." *Nat. Med.* 6:886-889.

Adams, S.E. et al. 1987 "The expression of hybrid HIV:Ty virus-like particles in yeast." *Nature* 329: 68-70.

Brown, J.R. et al. 1997 "Hydrophobic mannosides act as acceptors for trypanosome α-mannosyltransferases." *Glycobiology* 7: 549-558.

European Patent Office Communication (Supplementary Partial European Search Report) dated Apr. 11, 2007, pursuant to European Patent Application No. 03751792.7.

European Patent Office Communication (Supplementary Partial European Search Report) dated Nov. 13, 2006, pursuant to European Patent Application No. 03751792.7.

Myers, T.M. et al. 1997 "A Highly Conserved Region of the Sendai Virus Nucleocapsid Protein Contributes to the NP-NP Binding Domain." *Virology* 229: 322-335.

Pal, R. et al. 1981 "Pardaxin, a Hydrophobic Toxin of the Red Sea Flatfish, Disassembles the Intact Membrane of Vesicular Stomatitis Virus." *J. Biol. Chem.* 256: 10209-10212.

Patton, J.T. et al. 1983 "Cell-Free Synthesis and Assembly of Vesicular Stomatitis Virus Nucleocapsids." *J. Virol.* 45: 155-164.

Sanchez, A. et al. 1986 "Conserved Structures among the Nucleocapsid Proteins of the Paramyxoviridae: Complete Nucleotide Sequence of Human Parainfluenza Virus Type 3 NP mRNA." *Virology* 152: 171-180.

Sanchez, A. et al. 1998 "Biochemical Analysis of the Secreted and Virion Glycoproteins of Ebola Virus." *J. Virol.* 72: 6442-6447.

Sanchez, A. et al. 1998 "Variation in the Glycoprotein and VP35 Genes of Marburg Virus Strains." *Virology* 240: 138-146.

Tindle, R.W. et al. 1994 "Chimeric Hepatitis B Core Antigen Particles Containing B- and Th- Epitopes of Human Papillomavirus Type 16 E7 Protein Induce Specific Antibody and T-Helper Responses in Immunised Mice." *Virology* 200: 547-557.

\* cited by examiner

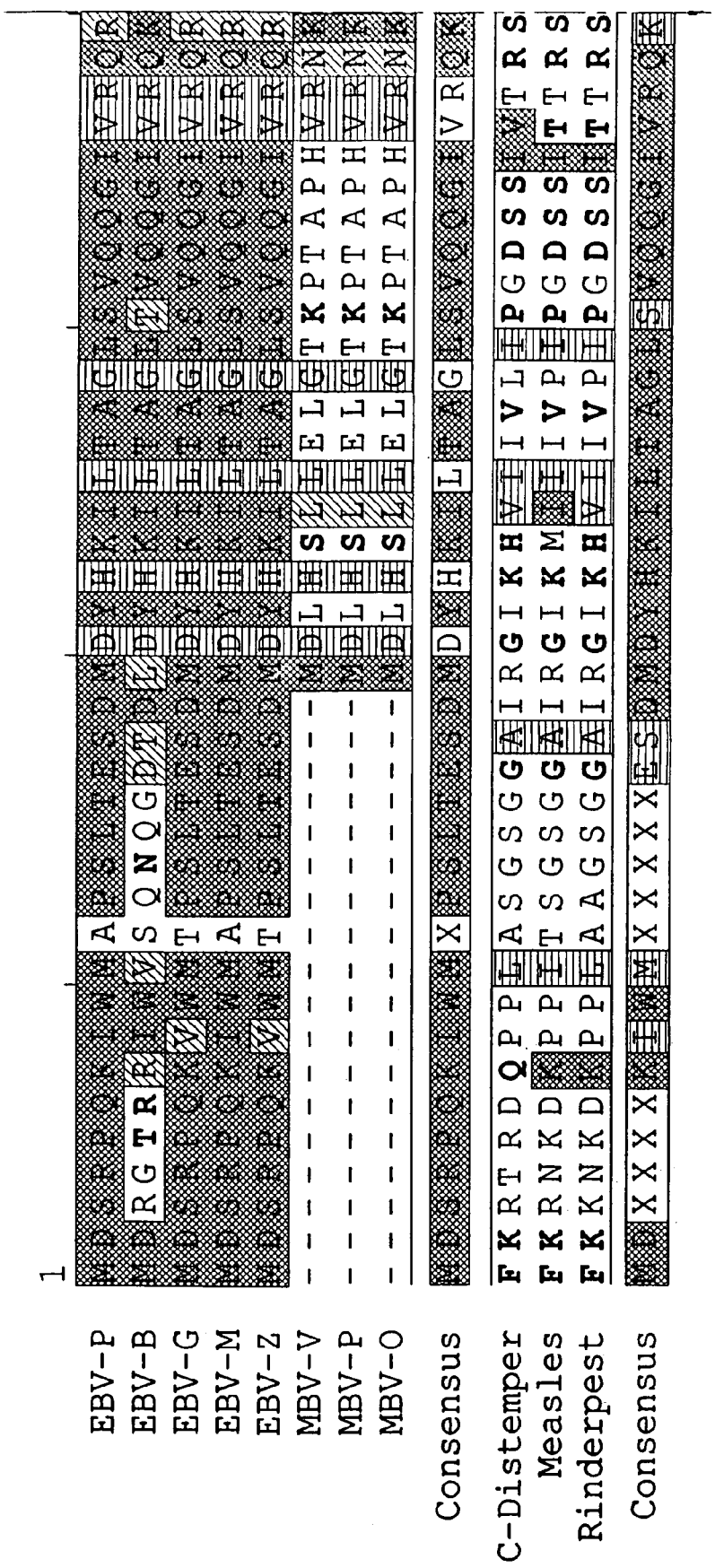
FIG. 6A₁

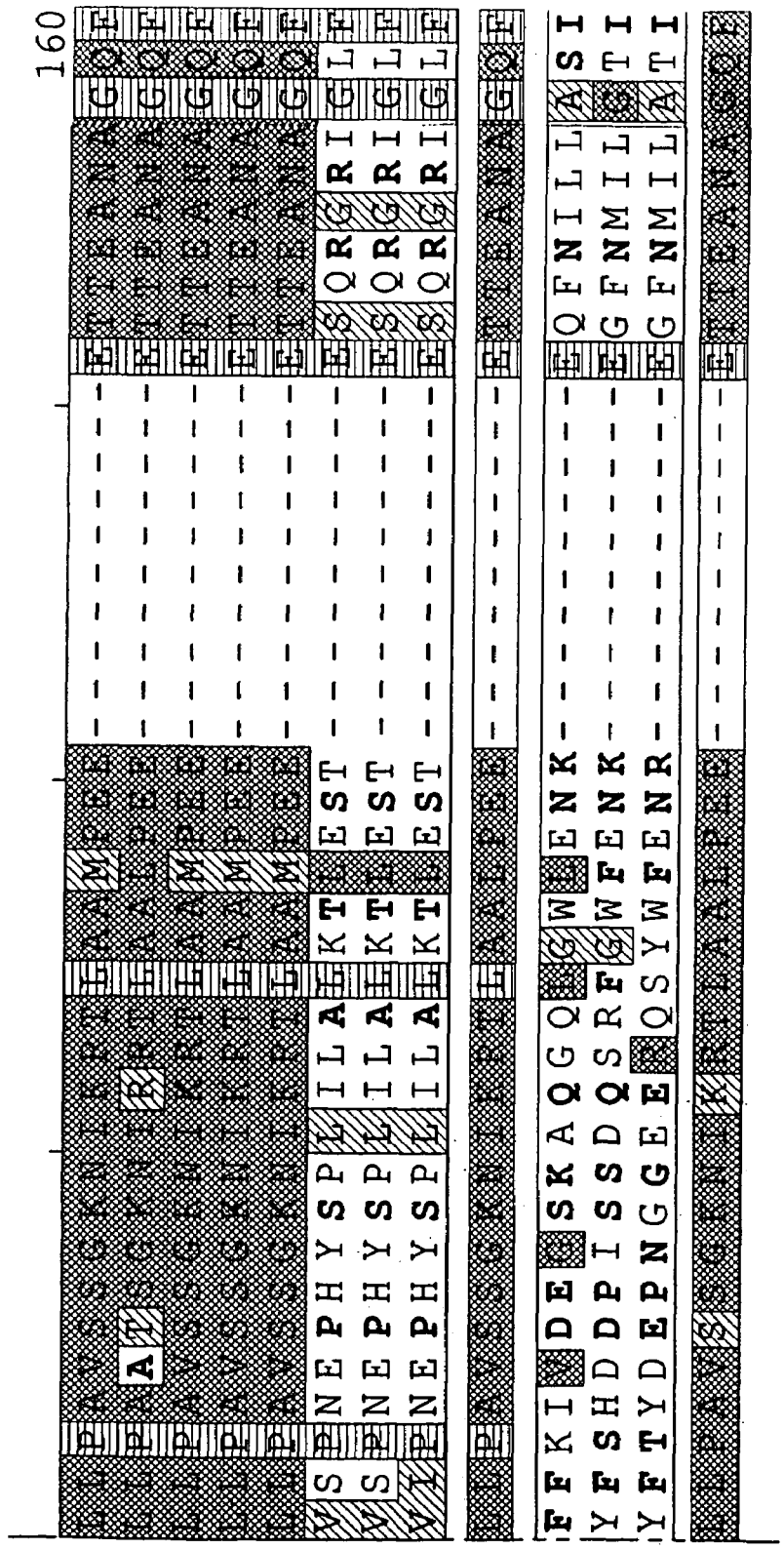
FIG. 6A₄

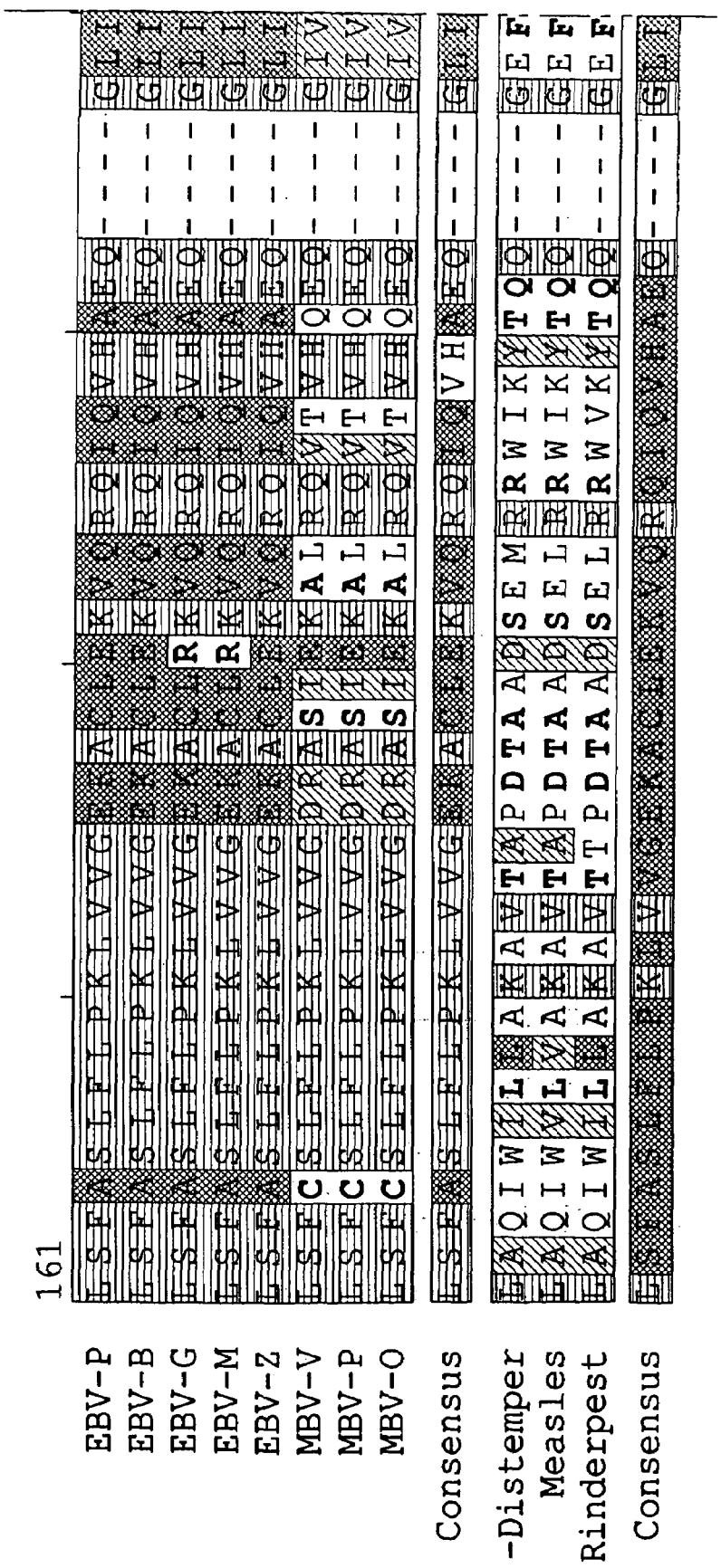
FIG. 6A5

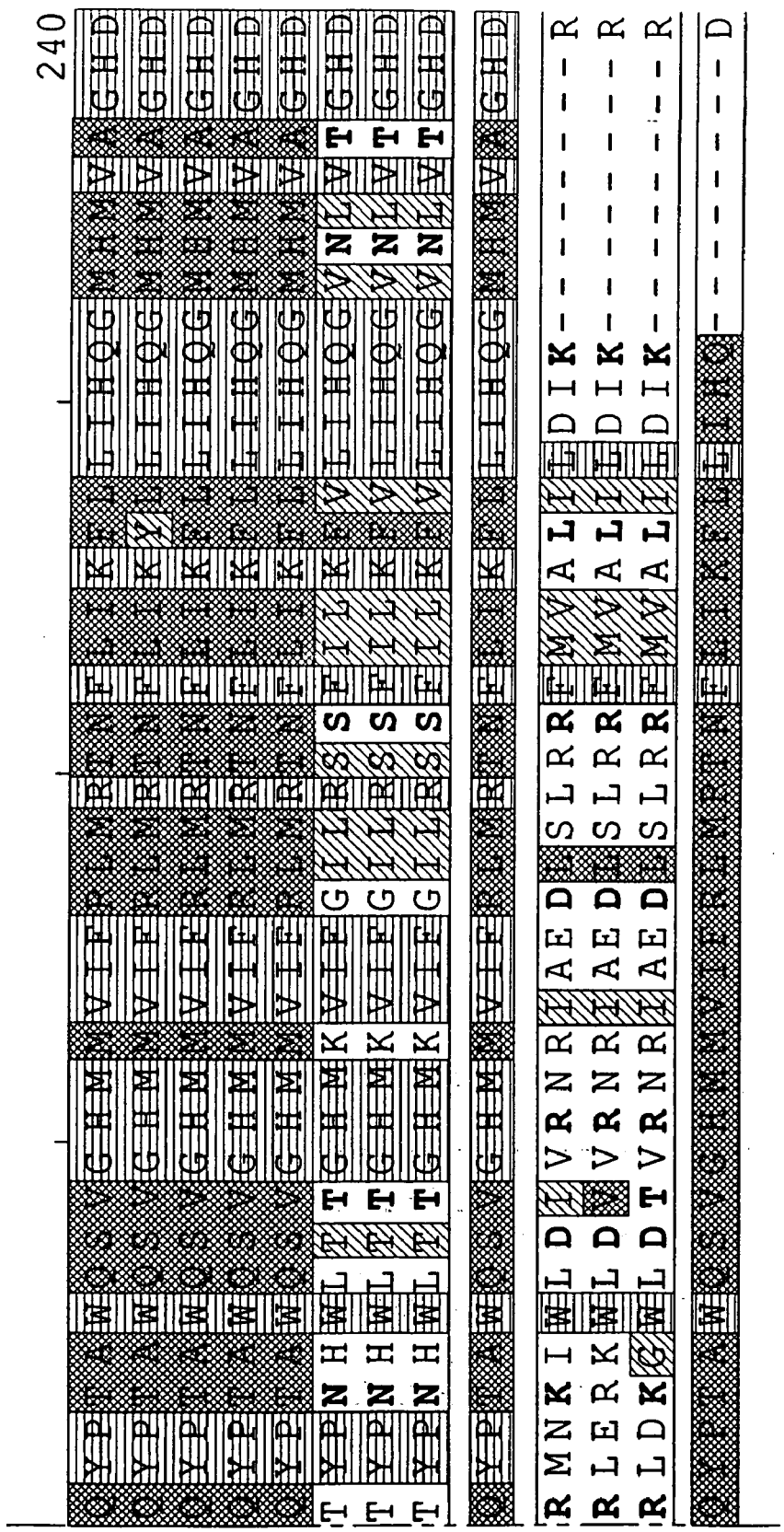
FIG. 6A6

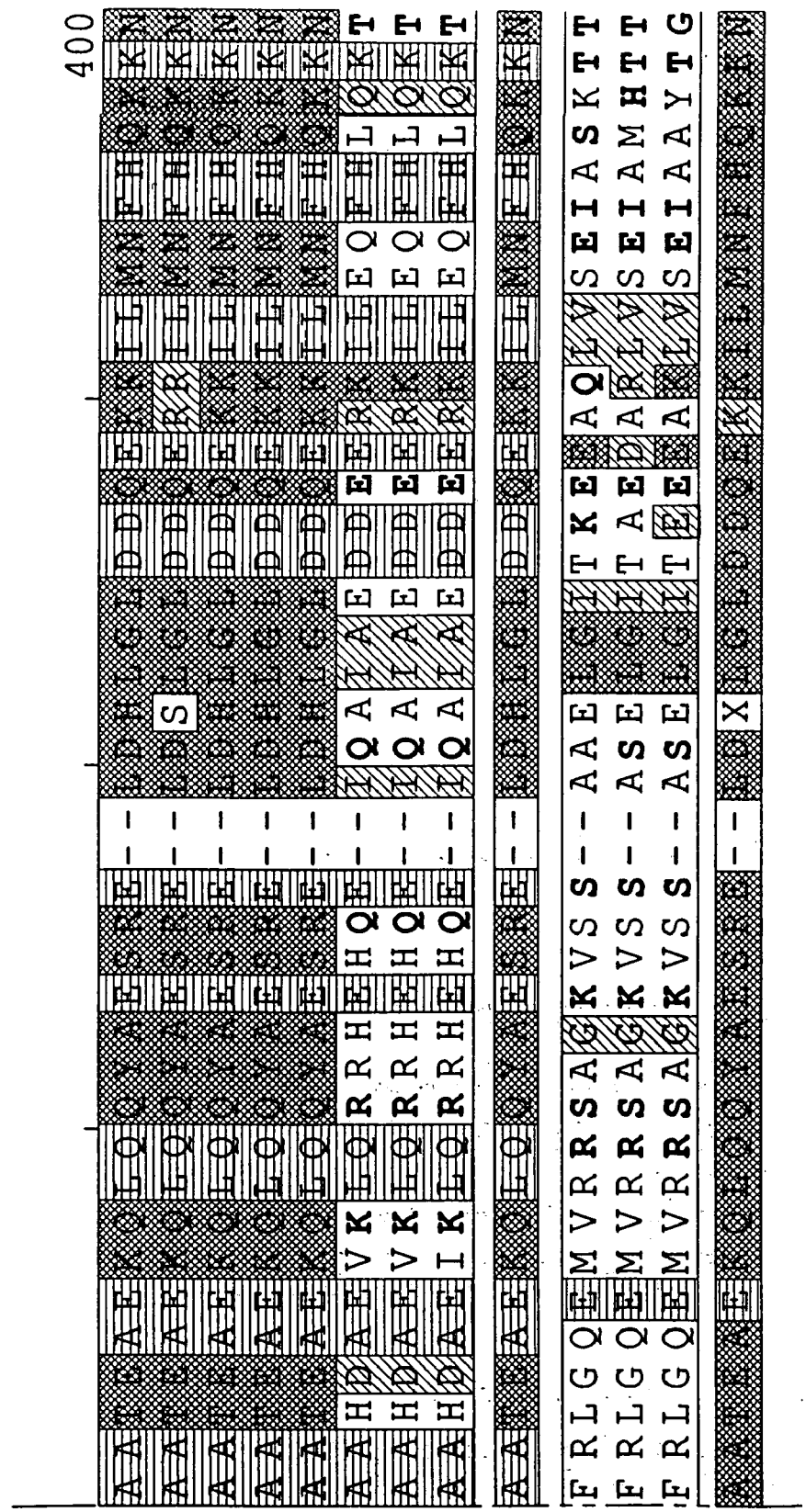
FIG. 6A₁₀

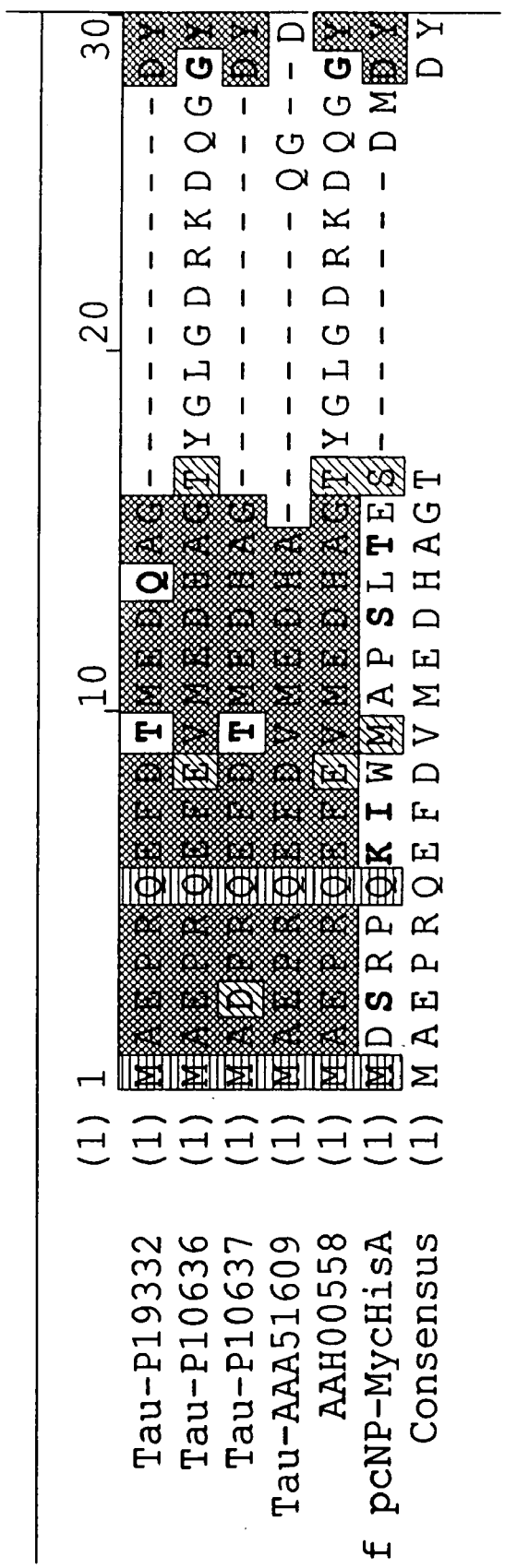
FIG. 7A₁

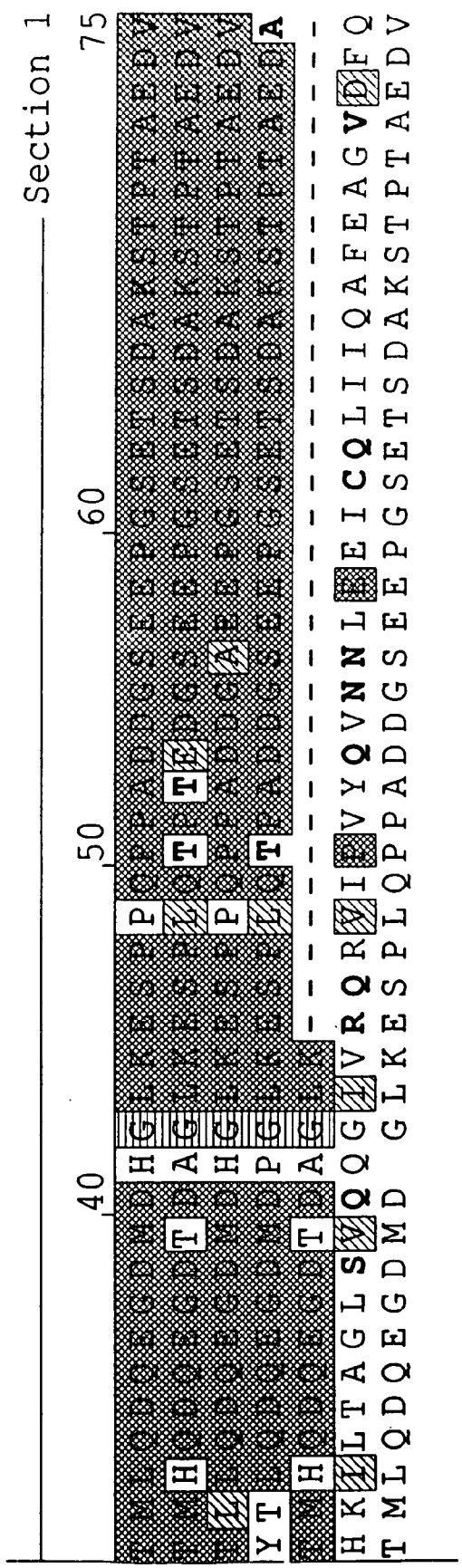
FIG. 7A2

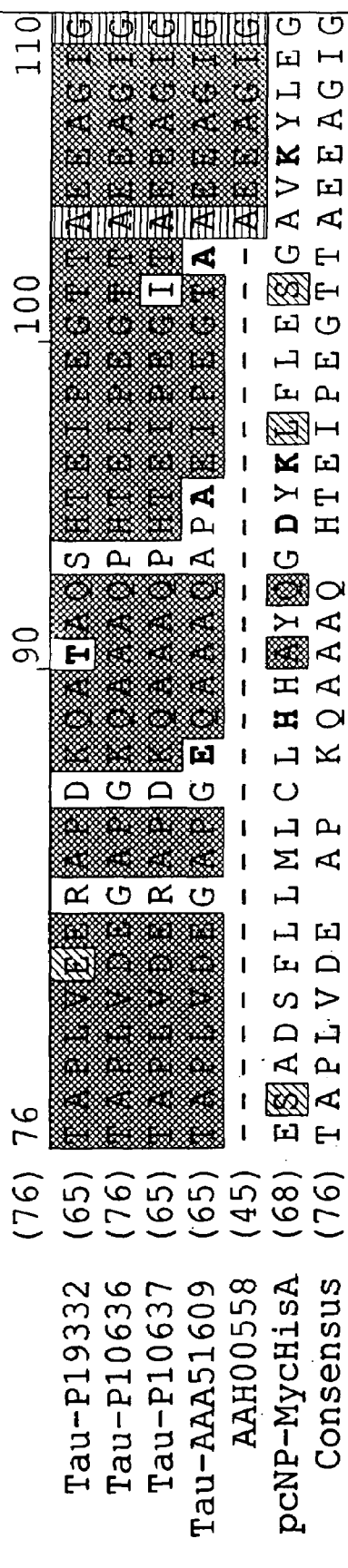
FIG. 7A3

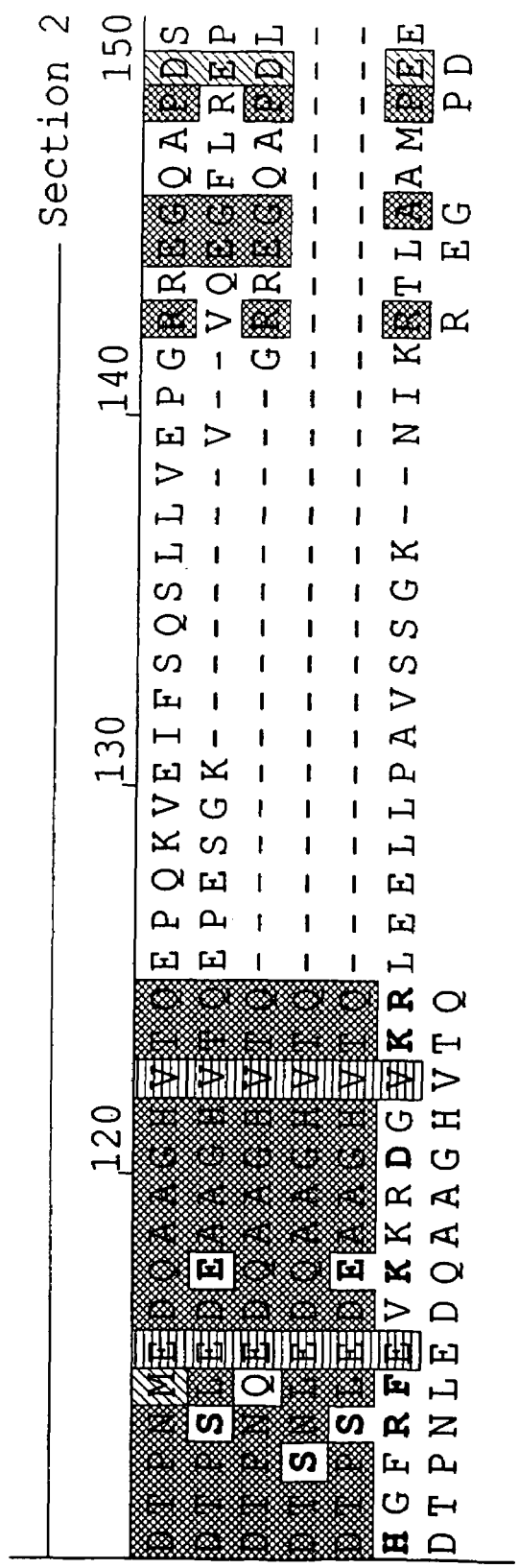
FIG. 7A4

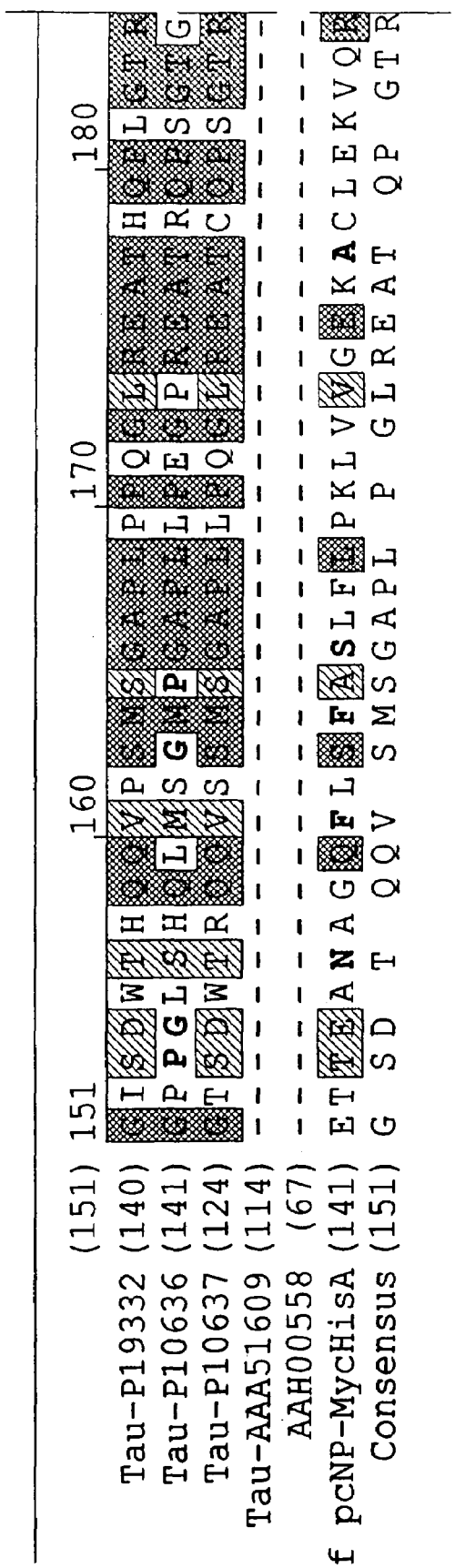
FIG. 7A5

FIG. 7A6

| FIG. 7B₁ | FIG. 7B₂ |
|---|---|
| FIG. 7B₃ | FIG. 7B₄ |
| FIG. 7B₅ | FIG. 7B₆ |

FIG. 7B

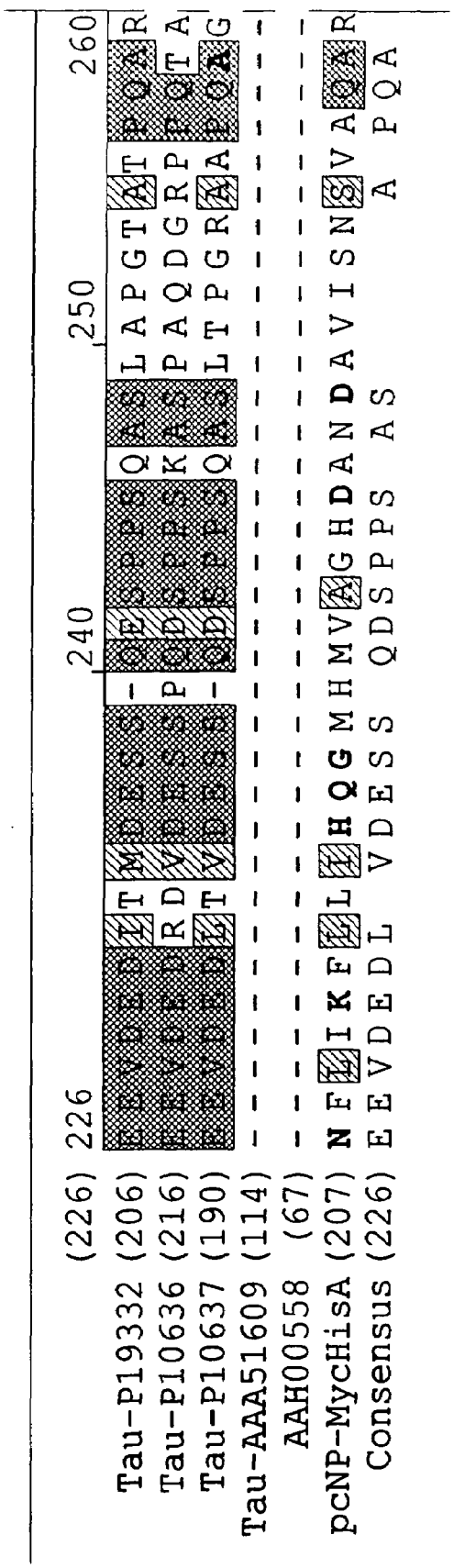
FIG. 7B₁

FIG. 7B₂

```
                       301                310              320              330
Tau-P19332    (280)    PE GT PSEE H E  AP    P  T E  KASAP KEQ
Tau-P10636    (284)    PD SV RAK- QDAPL  P  E E  TPNVQ EQA
Tau-P10637    (261)    PE GT PME E H E  AP    P  T  V  KASTP KEQ
Tau-AAA51609  (114)    — — — — — — — — — — — — — — — — — — — — — — — — — — — —
AAH00558       (67)    — — — — — — — — — — — — — — — — — — — — — — — — — — — —
pcNP-MycHisA  (282)    AALSSL  KHG  YAPF RLLNLSGVNNLEHGLFPQ
Consensus    (301)    PEGP    G       EG EAA EFTFHVEI        KEQ
```

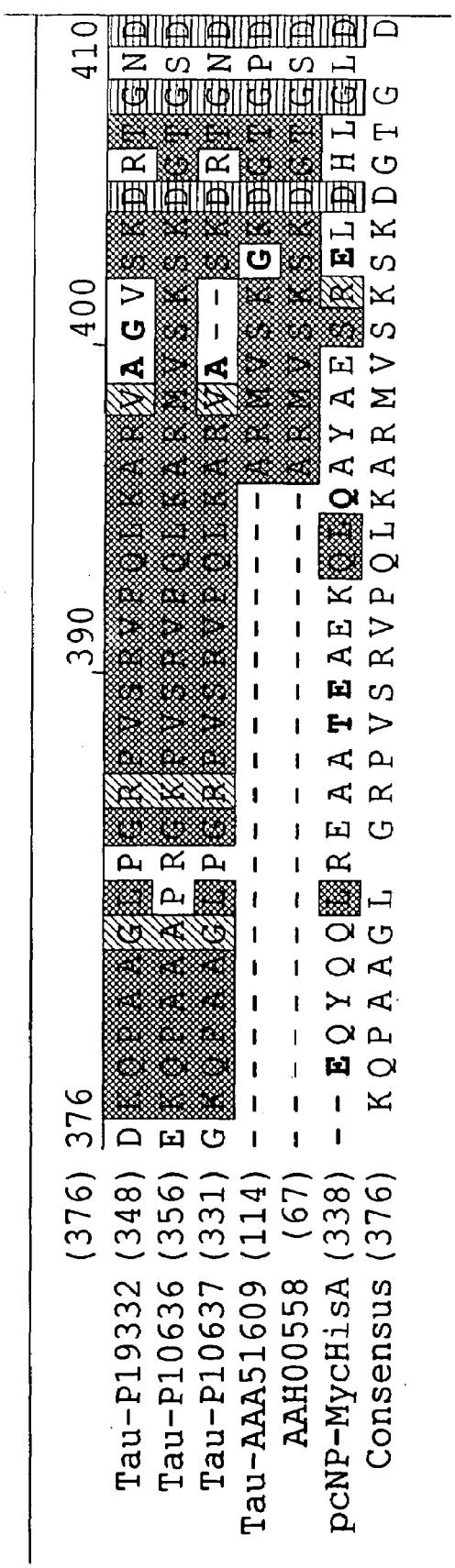
FIG. 7B₅

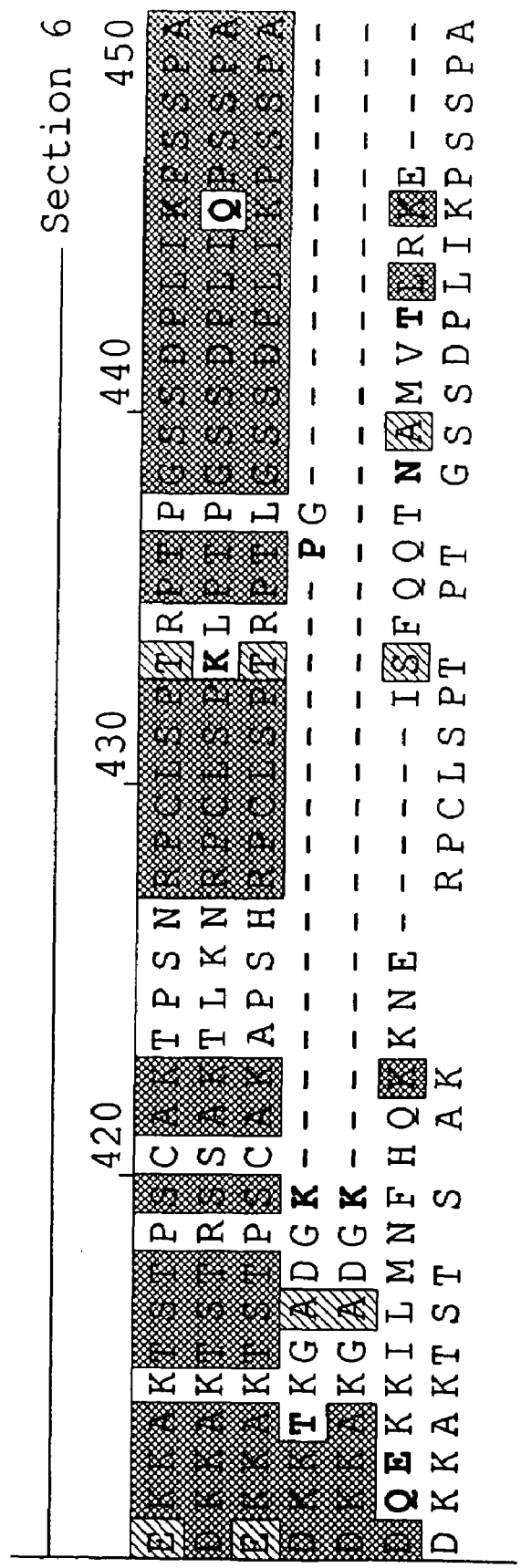
FIG. 7B6

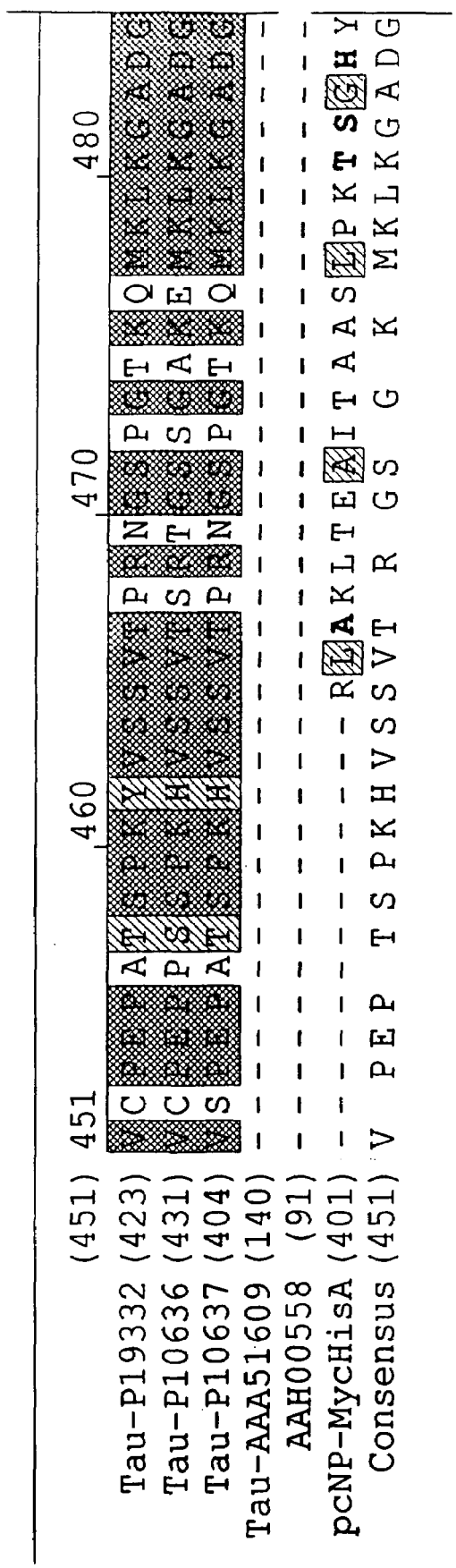
FIG. 7C₁

FIG. 7C₂

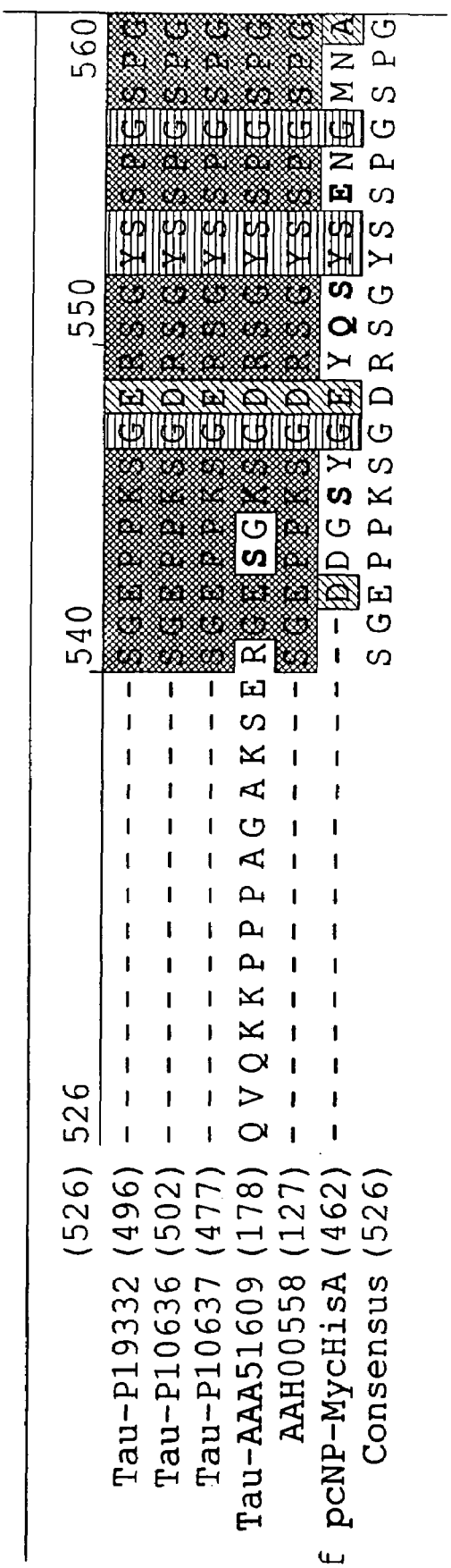
FIG. 7C₃

FIG. 7C4

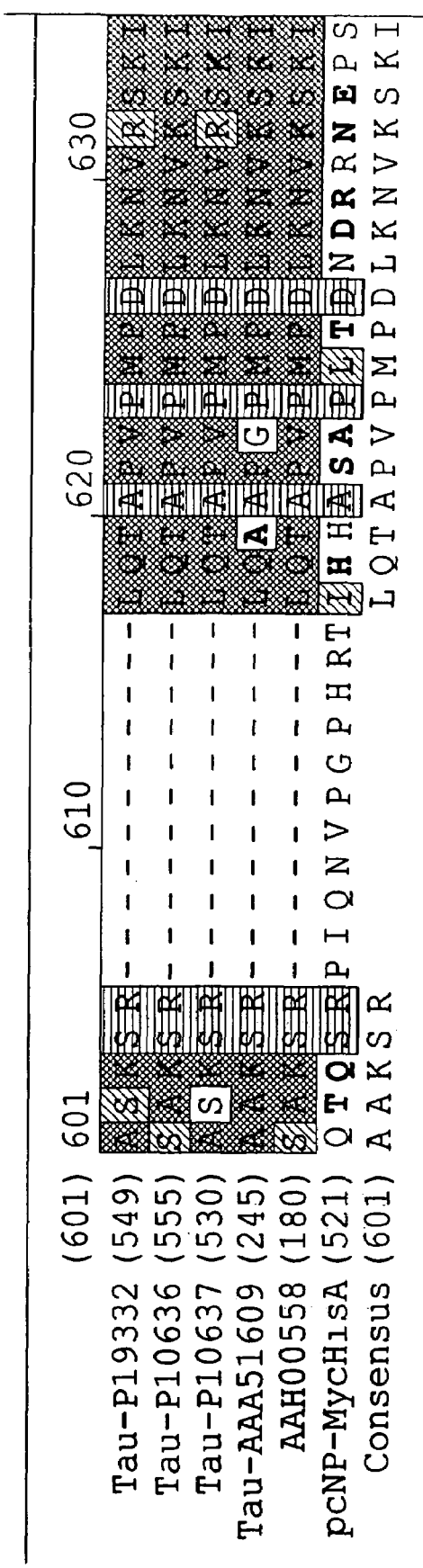
FIG. 7C5

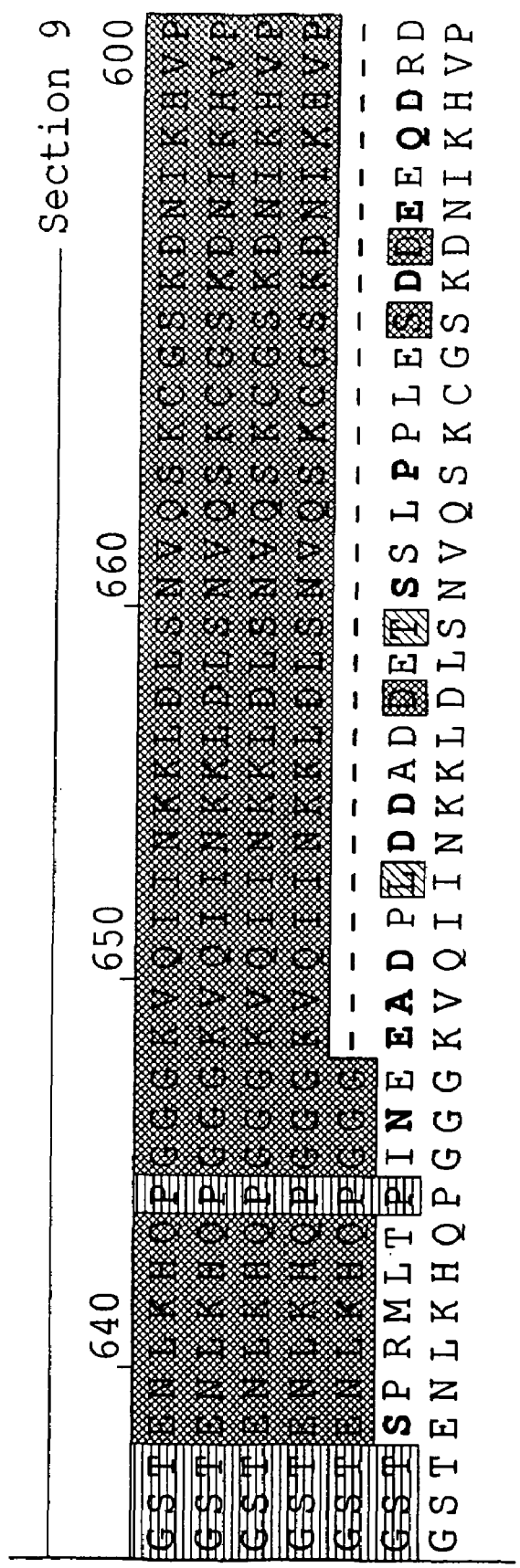
FIG. 7C6

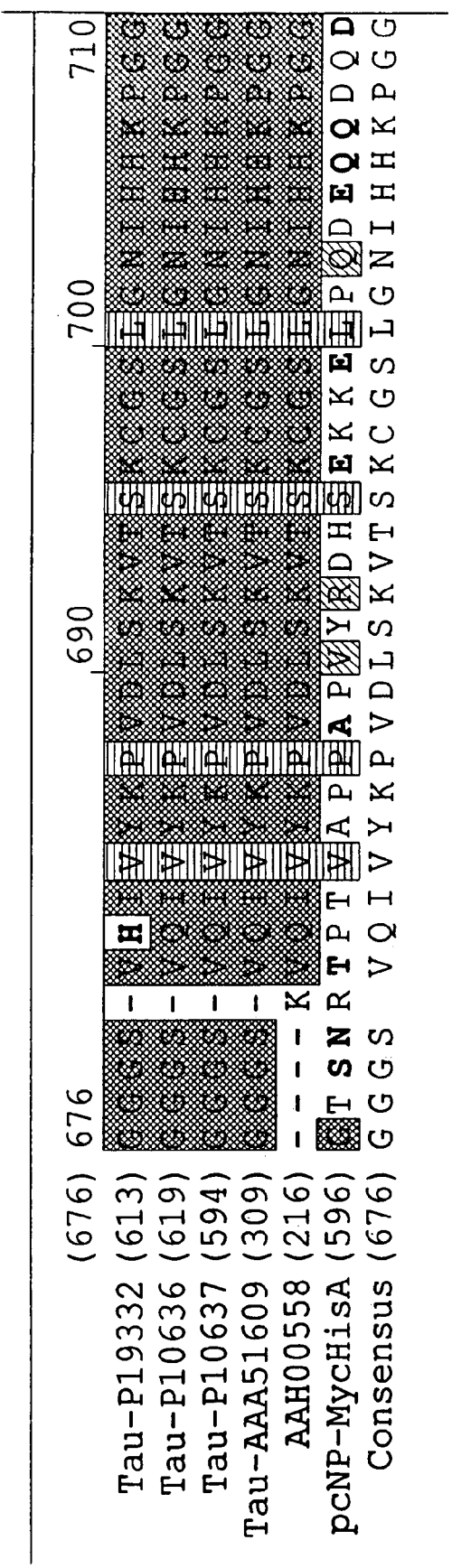
FIG. 7D₁

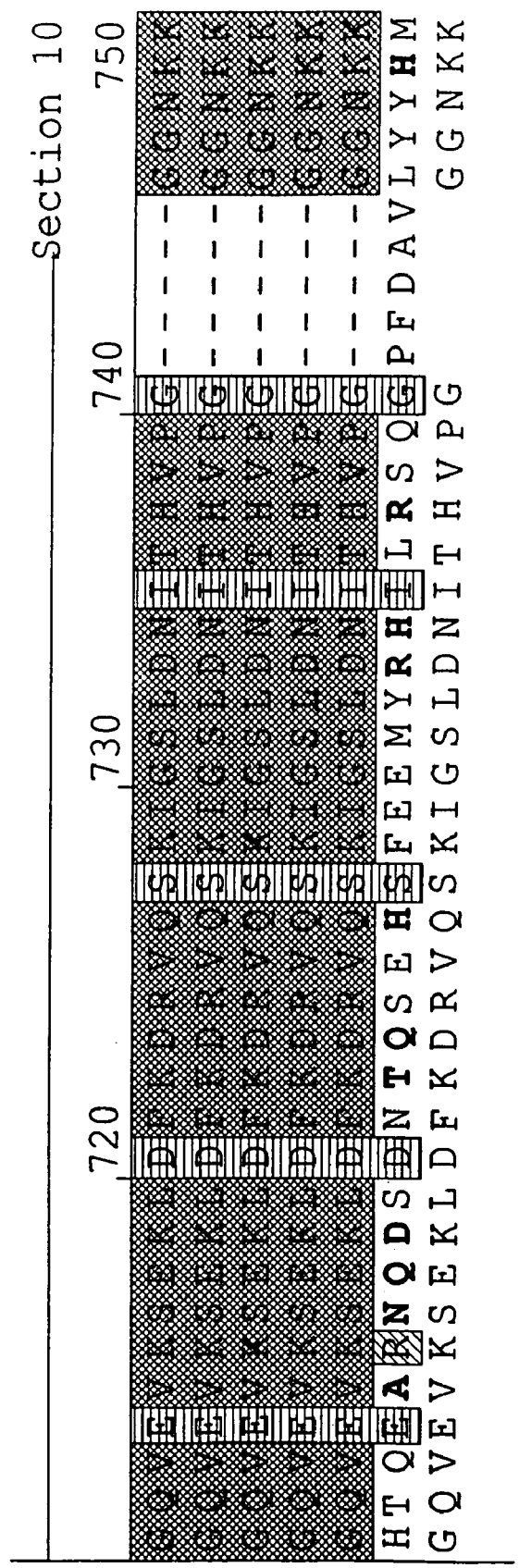
FIG. 7D2

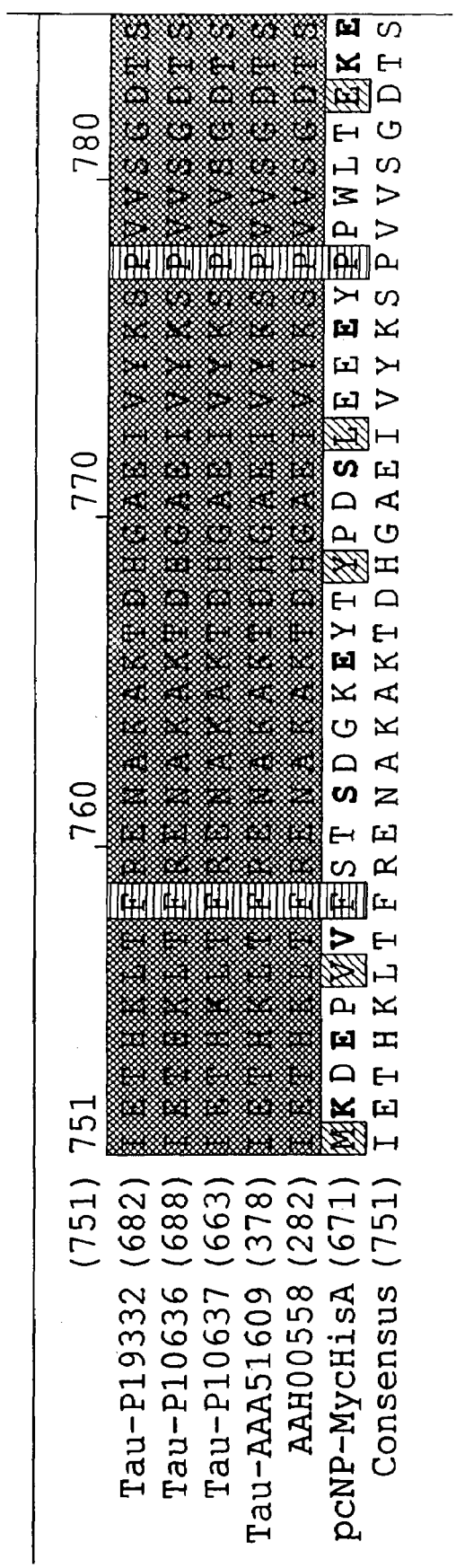
FIG. 7D₃

FIG. 7D₄

PRHLSNVSSTGSIDMVDSPQLATLADEVSASLAKQGL
AMNEERFVTLDGQQFYWPVNHKNKFMAILQHHQGPFEQK

|                    |       | 826 |   |   |   |   |   |   |   |   |   |   |   |   |   |   |   | Section 12 | 844 |
|--------------------|-------|---|---|---|---|---|---|---|---|---|---|---|---|---|---|---|---|---|---|
| Tau-P19332         | (753) | - | - | - | - | - | - | - | - | - | - | - | - | - | - | - | - | - | - |
| Tau-P10636         | (759) | - | - | - | - | - | - | - | - | - | - | - | - | - | - | - | - | - | - |
| Tau-P10637         | (734) | - | - | - | - | - | - | - | - | - | - | - | - | - | - | - | - | - | - |
| Tau-AAA51609       | (449) | - | - | - | - | - | - | - | - | - | - | - | - | - | - | - | - | - | - |
| AAH00558           | (353) | - | - | - | - | - | - | - | - | - | - | - | - | - | - | - | - | - | - |
| f pcNP-MycHisA     | (746) | L | I | S | E | E | D | L | N | M | H | T | G | H | H | H | H | H | R |
| Consensus          | (826) | - | - | - | - | - | - | - | - | - | - | - | - | - | - | - | - | - | - |

FIG. 7D5

ASSAYS FOR ASSEMBLY OF EBOLA VIRUS NUCLEOCAPSIDS

RELATED APPLICATIONS

This application is a continuation and claims the benefit of priority of International Application No. PCT/US2003/021757 filed Jul. 11, 2003, designating the United States of America and published in English on Jan. 22, 2004, as WO 2004/007747, which claims the benefit of priority of U.S. Provisional Application No. 60/395,876 filed Jul. 12, 2002, and U.S. Provisional Application No. 60/451,317 filed Feb. 28, 2003, all of which are hereby expressly incorporated by reference in their entireties.

FIELD OF THE INVENTION

The present invention relates to assays for the identification of compounds that inhibit assembly of NP, VP35, and VP24, or inhibit the glycosylation of NP, required for nucleocapsid formation, for use as anti-viral agents. The invention also relates to assays for the identification of compounds that block glycosylation of proteins having a glycosylation domain that is substantially homologous to a glycosylation domain of NP required for polymerization. The invention further relates to pseudoparticles for presentation of antigens or antigenic epitopes for immunogenic or vaccination purposes.

BACKGROUND OF THE INVENTION

Ebola viruses are enveloped, nonsegmented, negative-strand RNA viruses, which, together with Marburg viruses, are the only two known species in the family Filoviridae (Sanchez, A. et al. 2001 in: *Fields Virology*, D. M. Knipe and P. M. Howley, eds. Philadelphia: Lippincott Williams & Wilkens, pp. 1279-1304). Ebola and Marburg viruses have been linked to a number of lethal outbreaks of hemorrhagic fever in humans and in non-human primates (Feldmann, H. and Klenk, H.-D. 1996 *Adv Virus Res* 47:1-52). Filoviruses replicate rapidly in monocytes/macrophages, and fibroblasts during the early stage of the disease (Geisbert, T. W. et al. 1992 *J Comp Path* 106:137-152; Feldmann, H. et al. 1996 *J Virol* 70:2208-2214). They also infect endothelial cells, and the accumulation of Ebola glycoproteins, coupled with the massive loss of endothelial cells, plays an important role in its pathogenicity during the latter stages of the disease (Schnittler, H. J. et al. 1993 *J Clin Invest* 91:1301-1309; Yang, Z.-Y. et al. 1998 *Science* 282:843; Yang, Z.-Y. et al. 2000 *Nat Med* 6:886-889). There are four well-documented Ebola virus subtypes: Ebola-Zaire, Ebola-Sudan, Ebola-Reston (Geisbert, T. W. and Jahrling, P. B. 1995 *Virus Res* 39: 129-150) and Ebola-Cote d'Ivoire (Leguenno, B. et al. 1995 *Lancet* 345: 1271-1274). New outbreaks, such as those recently in Gulu, Uganda, and presently in Gabon are still emerging.

Ebola virions have a uniform diameter of 75-80 nm, with filamentous forms of approximately 970 nm in length showing peak infectivity (Geisbert, T. W. and Jahrling, P. B. 1995 *Virus Res* 39:129-150). An envelope putatively derived from the host cell membrane binds a 45-60 nm diameter nucleocapsid, and surface spikes are occasionally seen protruding from the viral envelope (Geisbert, T. W. and Jahrling, P. B. 1995 *Virus Res* 39:129-150). The 19 kb single negative-strand RNA genome encodes seven viral proteins: nucleoprotein (NP), virion protein (VP) 24, VP30, VP35, VP40, glycoprotein (GP), and RNA-dependent RNA polymerase (L) (Feldmann, H. et al. 1992 *Virus Res* 24:1-19; Sanchez, A. et al. 1993 *Virus Res* 29:215-240).

Despite the limited number of Ebola virus open reading frames, little is known about viral assembly and the control of Ebola virus replication. Some studies have suggested that replication occurs in the cytoplasm, and assembly and budding of new viral particles takes place at the plasma membrane (Feldmann, H. and Kiley, M. P. 1999 *Curr Top Microbiol Immunol* 235:1-21; Feldmann, H. et al. 1996 *J Virol* 70:2208-2214; Feldmann, H. and Klenk, H.-D. 1996 *Adv Virus Res* 47:1-52); however, the possibility of lytic replication and release from intracellular lysosomes cannot be excluded. Studies of Ebola and Marburg viruses using an artificial replication system based on vaccinia virus T7 expression have shown that three proteins, NP, VP35, and L, are able to support transcription of a monocistronic mini-replicon (Muhlberger, E. et al. 1998 *J Virol* 72:8756-8764; Muhlberger, E. et al. 1999 *J Virol* 73:2333-2342). More recently, an elegant reverse genetic system was utilized to generate infectious Ebola virus with a combination of viral genomic fragments and expression vectors derived from four cDNAs (NP, VP35, VP30, and L). This system was used to analyze the role of GP in viral cytopathicity in vitro (Volchkov, V. E. et al. 2001 *Science* 291:1965-1969).

SEGUE TO THE INVENTION

In the present report, analysis of Ebola virus assembly has been undertaken using cDNAs encoding six of the seven open reading frames. Co-transfection of these expression vectors gave rise to intracellular virus-like particles. The viral gene products and biochemical interactions required for this process have been defined. These results indicate a novel mechanism that regulates the assembly of filoviruses within cells.

SUMMARY OF THE INVENTION

The present invention relates to assays for the identification of compounds that inhibit assembly of NP, VP35, and VP24, or inhibit the glycosylation of NP, required for nucleocapsid formation, for use as anti-viral agents. The invention also relates to assays for the identification of compounds that block glycosylation of proteins having a glycosylation domain that is substantially homologous to a glycosylation domain of NP required for polymerization. The invention further relates to pseudoparticles for presentation of antigens or antigenic epitopes for immunogenic or vaccination purposes.

BRIEF DESCRIPTION OF THE SEQUENCES

Figure 1A:
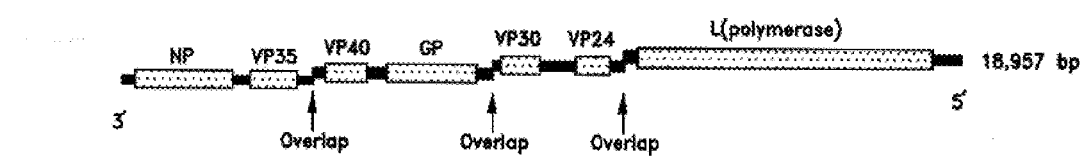
FIG. 1 is Ebola gene organization and transmission electron microscopy (TEM) analysis of Ebola capsid assembly. A. Schematic representation of Ebola genome organization. The genes encoding viral proteins are drawn to scale. Dotted areas denote the coding regions and bar areas denote the noncoding sequences. From 3' to 5': NP, VP35, VP40, GP, VP30, VP24 and L gene encoding for RNA polymerase (L). B. Electron micrographs of the assembly of Ebola capsids in transfected 293T cells (magnification×7000). Two µg of each of six plasmids coding for pVR1012-GP, NP, VP40, VP35, VP30, and VP24, respectively, were used to co-transfect $3 \times 10^6$ 293T cells, using the calcium phosphate method (12 µg total DNA per transfection). TEM analysis was performed using the method described in Table 1, legend. C. Longitudinal section (magnification×150,000) of 293 cells cotransfected with four plasmids (2 µg each) encoding NP, VP35, VP30, and VP24, respectively, and 4 µg of the vector backbone. A total of 12 µg DNA was used for each transfection, and cells were analyzed as described below. D. Transverse section (magnification×100,000) of cells described in 1C).

| Sequence | GenBank Accession No. |
|---|---|
| Ebola Zaire NP | AF272001 |
| Ebola Zaire VP35 | AF272001 |
| Ebola Zaire VP24 | AF272001 |
| Ebola Sudan NP | AF173836 |
| Ebola Sudan VP35 | None in Genbank |
| Ebola Sudan VP24 | None in Genbank |
| Ebola Reston NP | AB050936 |
| Ebola Reston VP35 | AB050936 |
| Ebola Reston VP24 | AB050936 |
| Ebola Cote d'Ivoire NP | None in Genbank |
| Ebola Cote d'Ivoire VP35 | None in Genbank |
| Ebola Cote d'Ivoire VP24 | None in Genbank |
| Marburg NP | NC_001608 |
| Marburg VP35 | NC_001608 |
| Marburg VP24 | NC_001608 |

DETAILED DESCRIPTION OF THE PREFERRED EMBODIMENT

Ebola virus encodes seven viral structural and regulatory proteins that support its high rates of replication, but little is known about nucleocapsid assembly of this virus in infected cells. In this disclosure, we report that three viral proteins are necessary and sufficient for the formation of Ebola virus particles and that intracellular post-translational modification regulates this process. Expression of the nucleoprotein (NP) and the virion-associated proteins VP35 and VP24 in the absence of other viral sequences led to the spontaneous assembly of nucleocapsids in transfected 293T cells by transmission electron microscopy (TEM). Full-length nuclear protein was required for formation of these complexes, and a specific biochemical interaction of these three proteins was demonstrated in vitro and in vivo. Interestingly, post-translational modification of nucleoprotein, including O-glycosylation and sialation, was required for their interaction, and a synthetic glycoside was identified that inhibited their biochemical interaction in vitro. Ebola virus therefore directs nucleocapsid assembly through three viral gene products and is dependent on intracellular post-translational modification. These results demonstrate a novel mechanism of regulation for virus assembly and indicate new approaches for the achievement of Ebola viral therapies and vaccines.

Assays for Compounds that Inhibit Assembly of NP, VP35, and VP24, or Inhibit Glycosylation of NP, Required for Nucleocapsid Formation The present invention relates to the identification and use of compounds that inhibit the assembly of NP, VP35, and VP24, or that inhibit the glycosylation of NP, required for nucleocapsid formation. Assays are described to identify compounds that inhibit the interaction of NP, VP35, and VP24, or that inhibit the covalent attachment of sugars to NP, remove the attached sugars from NP, or inhibit the biosynthesis of sugars, and disrupt the formation of infectious virus. Inhibitory compounds that are relatively non-toxic, e.g., display a good therapeutic index, may be utilized as antiviral agents for the treatment of viral infection in animals, including humans.

For clarity of discussion, the invention is described in the subsections below for filoviruses. However, the principles may be analogously applied to other viruses in which interactions of analogues of these proteins, N(NP) and P proteins, have been seen. These viruses include paramyxoviruses (e.g., sendai virus, mumps virus, measles virus, distemper virus, rinderpest virus, and respiratory syncytial virus), arenaviruses, bornaviruses, bunyviruses, orthomyxoviruses (e.g., influenza virus), and rhabdoviruses that are negative-stranded RNA viruses capable of forming filaments.

Screening Assays

The following assays are designed to identify compounds that inhibit nucleocapsid assembly. The compounds which may be screened in accordance with the invention include, but are not limited to, small organic molecules, peptides, and peptidomimetics that interact with (e.g., bind to) NP, VP35, or VP24, or block glycosylation of NP, and inhibit nucleocapsid assembly; as well as small organic molecules, peptides, and peptidomimetics that mimic binding domains of NP, VP35, or VP24 and act as molecular decoys to bind and "neutralize" natural ligand, or that mimic glycosylation domains of NP. In one example, peptide fragments corresponding to binding domains of NP, VP35, or VP24 compete with and inhibit the interaction of these proteins, or peptide fragments corresponding to glycosylation domains compete with and inhibit glycosylation of NP. Inhibitory compounds identified in the foregoing screening assays that may be used in accordance with the invention, may include but are not limited to small organic molecules, peptides, and peptidomimetics. The assays can be used to identify compounds that inhibit the interaction of NP, VP35, and VP24, or that inhibit the glycosylation of NP, by, for example, competing with domains of NP as the recipient of sugars, or blocking the sites for sugar attachment, or by blocking the nucleocapsid assembly sites or competing with proteins as substrates for nucleocapsid assembly.

The principle of the assays used to identify compounds that bind to NP, VP35, or VP24 involves preparing a reaction mixture of NP, VP35, or VP24 and the test compound under conditions and for a time sufficient to allow the two components to interact and bind, thus forming a complex which can be removed and/or detected in the reaction mixture. The NP, VP35, or VP24 species used can vary depending upon the goal of the screening assay. For example, the full length NP, VP35, or VP24, a peptide corresponding to the binding domain of NP, VP35, or VP24, or a fusion protein containing full length NP, VP35, or VP24, or a peptide corresponding to the binding domain of NP, VP35, or VP24, fused to a protein or polypeptide that affords advantages in the assay system (e.g., labeling, isolation of the resulting complex, etc.) can be utilized.

The screening assays can be conducted in a variety of ways. For example, one method to conduct such an assay would involve anchoring the NP, VP35, or VP24 protein, peptide or fusion protein or the test substance onto a solid phase and detecting NP, VP35, or VP24/test compound complexes anchored on the solid phase at the end of the reaction. In one embodiment of such a method, the NP, VP35, or VP24 reactant may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for NP, VP35, or VP24 protein, peptide or fusion protein or the test compound to anchor any complexes formed in solution, and a labeled antibody specific for the other component of the possible complex to detect anchored complexes.

Alternatively, cell-based assays can be used to identify compounds that interact with NP, VP35, or VP24. To this end, cell lines that express NP, VP35, or VP24, or cell lines (e.g., COS cells, CHO cells, 293 cells, etc.) that have been genetically engineered to express NP, VP35, or VP24 (e.g., by transfection or transduction of NP, VP35, or VP24 cDNA) can be used. Interaction of a cell-permeable test compound with the NP, VP35, or VP24 expressed by the host cell can be determined by comparison or competition with native ligand.

Any method suitable for detecting protein-protein interactions may be employed for identifying compounds that inhibit nucleocapsid assembly. Among the traditional methods which may be employed are co-immunoprecipitation, crosslinking and co-purification through gradients or chromatographic columns of cell lysates or proteins obtained from cell lysates and NP, VP35, or VP24 to identify proteins in the lysate that interact with NP, VP35, or VP24. For these assays, the NP, VP35, or VP24 component used can be a full length NP, VP35, or VP24, a peptide corresponding to the binding domain of NP, VP35, or VP24, or a fusion protein containing full length NP, VP35, or VP24, or a peptide corresponding to the binding domain of NP, VP35, or VP24, fused to a protein or polypeptide.

The macromolecules that interact with NP, VP35, or VP24 are referred to, for purposes of this discussion, as "binding partners" (i.e., for NP: VP35 or VP24; for VP35: NP or VP24; and for VP24: NP or VP35). The basic principle of the assay systems used to identify compounds that inhibit the interaction between NP, VP35, or VP24 and its binding partner or partners involves preparing a reaction mixture containing full length NP, VP35, or VP24, a peptide corresponding to the binding domain of NP, VP35, or VP24, or a fusion protein containing full length NP, VP35, or VP24, or a peptide corresponding to the binding domain of NP, VP35, or VP24, fused to a protein or polypeptide, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of the NP, VP35, or VP24 moiety and its binding partner. Control reaction mixtures are incubated without the test compound or with a placebo. The formation of any complexes between the NP, VP35, or VP24 moiety and the binding partner is then detected. The formation of a complex in the control reaction, but not in the reaction mixture containing the test compound, indicates that the compound interferes with the interaction of NP, VP35, or VP24 and the interactive binding partner.

The assay for compounds that inhibit the interaction of NP, VP35, or VP24 and binding partners can be conducted in a heterogeneous or homogeneous format. Heterogeneous assays involve anchoring either the NP, VP35, or VP24 moiety product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that inhibit the interaction by competition can be identified by conducting the reaction in the presence of the test substance; i.e., by adding the test substance to the reaction mixture prior to or simultaneously with the NP, VP35, or VP24 moiety and interactive binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the NP, VP35, or VP24 moiety or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the NP, VP35, or VP24 or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the NP, VP35, or VP24 moiety and the interactive binding partner is prepared in which either the NP, VP35, or VP24 or its binding partner is labeled, but the signal generated by the label is quenched due to formation of the complex (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt NP, VP35, or VP24/binding partner interaction can be identified.

In a particular embodiment, a NP, VP35, or VP24 fusion protein can be prepared for immobilization. For example, the full length NP, VP35, or VP24, or a peptide corresponding to the binding domain of NP, VP35, or VP24, can be expressed with glutathione-S-transferase (GST) using a fusion vector, such as pGEX-5X-1, in such a manner that its binding activity is maintained in the resulting fusion protein. The interactive binding partner can be purified and used to raise a monoclonal antibody, using methods routinely practiced in the art. This antibody can be labeled with a radioactive isotope by methods routinely practiced in the art. In a heterogeneous assay, e.g., the GST-NP, VP35, or VP24 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the NP, VP35, or VP24 and the interactive binding partner can be detected by measuring the amount of radioactivity that remains associated with the glutathione-agarose beads. A successful inhibition of the interaction by the test compound will result in a decrease in measured radioactivity.

Alternatively, the GST-NP, VP35, or VP24 fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the NP, VP35, or VP24/binding partner interaction can be detected by adding the labeled antibody and measuring the radioactivity associated with the beads.

In another embodiment of the invention, these same techniques can be employed using peptide fragments that correspond to the binding domains of NP, VP35, or VP24, in place of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, since the gene coding for the intracellular binding partner is available, short gene segments can be engineered to express peptide fragments of the protein, which can then be tested for binding activity and purified or synthesized.

For example, and not by way of limitation, NP, VP35, or VP24 can be anchored to a solid material as described, above, by making a GST-NP, VP35, or VP24 fusion protein and allowing it to bind to glutathione agarose beads. The interactive binding partner can be labeled with a radioactive isotope and cleaved with a proteolytic enzyme such as trypsin. Cleavage products can then be added to the anchored GST-NP, VP35, or VP24 fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

Compounds, including but not limited to binding compounds identified via assay techniques such as those described in the preceding sections above can be tested for the ability to inhibit nucleocapsid assembly. Cell-based systems can be used. Such systems can include, for example, recombinant or non-recombinant cells, such as cell lines, which express the NP, VP35, or VP24 gene. In addition, expression host cells (e.g., COS cells, CHO cells, 293 cells) genetically engineered to express a functional NP, VP35, or VP24 protein and to respond to association by the natural ligand (such as the corresponding NP, VP35, or VP24 protein), e.g., as measured by a chemical or phenotypic change, can be used as an end point in the assay.

Additional Cell Screening and In Vitro Screening Assays

The assays described herein are designed to measure assembly of NP, VP35, and VP24, or glycosylation of NP, synthesized by genetically engineered cells. These assays are conducted in cells or in vitro, and can be used to identify substances that inhibit assembly of NP, VP35, and VP24, or glycosylation of NP, and the production of nucleocapsids. In the assays of the invention, a protein selected from the group consisting of NP, VP35, and VP24 is reacted in cells or in vitro with a test substance to form a reaction mixture. The mixture is then incubated to determine if nucleocapsid formation is inhibited. In one example, as the nucleocapsids are formed, the mixture will become increasingly turbid, and thus the rate of nucleocapsid formation can be monitored by measuring the amount of light deflected or absorbed by the mixture over time. Inhibition of binding indicates the ability of the test substance to block the assembly of NP, VP35, and VP24 and inhibit the formation of infectious virus. Alternatively, NP is reacted in cells or in vitro with a sugar group or donor of a sugar group in the presence of a protein glycosylation enzyme that is responsible for glycosylation. Incorporation of the sugar group into NP is an indication of glycosylation. Inhibition of the incorporation of the sugar group by the test substance indicates the ability of the test substance to block glycosylation of NP and inhibit the formation of infectious virus.

In the assays of the invention, assembly of NP, VP35, and VP24, and glycosylation of NP, may be detected by a variety of methods. For example, binding of NP, VP35, and VP24, or incorporation of a sugar group into NP, can be detected by a change in the mobility of the reaction product as determined by chromatographic methods, including but not limited to TLC (thin layer chromatography), HPLC (high performance liquid chromatography), or electrophoretic methods such as SDS-PAGE. Additionally, any substrate, NP, VP35, or VP24, or a sugar group, may be labeled so that detection of the label in the reaction product can be used as an indicator of assembly of NP, VP35, and VP24, or glycosylation of NP. To this end, a variety of signal generating compounds, including but not limited to radiolabels (e.g., $^{3}$H, $^{14}$C, $^{32}$P, $^{35}$S, $^{125}$I, $^{131}$I), fluorogenic compounds, colorimetric compounds, enzymes, etc., may be incorporated into the substrate using standard metabolic labeling techniques or chemical conjugating techniques known in the art. Antibodies specific for the substrate may be used to isolate and/or capture the reaction product. Where solid supports are utilized, one of the reactants can be immobilized on the surface of the support by non-covalent or covalent attachments. For example, the immobilization of proteins such as anti-NP, anti-VP35, or anti-VP24 can be accomplished by coating the support with a solution of the protein and drying. The coated supports may be prepared in advance and stored prior to use.

Assay Components

The NP, VP35, or VP24, or a sugar group, sugar group donor, or protein glycosylation enzyme, that forms the components of the reaction may be obtained in a variety of ways.

The cell screening assays utilize genetically engineered cells that express a protein selected from the group consisting of NP, VP35, or VP24 in cells, optionally which are capable of glycosylation. Such cells or cell lines may be engineered to express NP, VP35, and VP24 using techniques known to those skilled in the art (e.g., see Sambrook et al. 1989 *Molecular Cloning: A Laboratory Manual*, Cold Spring Harbor Laboratory Press, Cold Spring Harbor, N.Y.). Such cells provide all the components necessary for assembly of NP, VP35, and VP24, or glycosylation of NP, and can be used as described herein with a labeled NP, VP35, or VP24, or with a labeled sugar, and/or with antibodies specific for NP, VP35, or VP24, or for the sugar, that can be used to recover the reaction product from the cells and/or for detection.

Antibodies specific for NP, VP35, and VP24 may be prepared by any of a variety of well-known techniques. In a preferred embodiment, the antibodies in the assay should be directed to epitopes of NP, VP35, and VP24 that do not interfere with assembly of NP, VP35, and VP24, or glycosylation of NP.

For the production of antibodies, various host animals may be immunized by injection with NP, VP35, and VP24 or portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique that provides for the production of antibody molecules by continuous cell lines in culture. These include but are not limited to the hybridoma technique originally described by Kohler and Milstein, (1975 *Nature* 256:495-497), the human B-cell hybridoma technique (Kosbor et al. 1983 *Immunol Today* 4:72; Cote et al. 1983 *PNAS USA* 80:2026-2030) and the EBV-hydridoma technique (Cole et al. 1985 *Monoclonal Antibodies and Cancer Therapy* Alan R. Liss, Inc., pp. 77-96). In addition, techniques developed for the production of "chimeric antibodies" (Morrison et al. 1984 *PNAS USA* 81:6851-6855; Neuberger et al. 1984 *Nature* 312:604-608; Takeda et al., 1985 *Nature* 314:452-454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce single chain antibodies specific to NP, VP35, and VP24.

Antibody fragments that recognize specific epitopes may be generated by known techniques. For example, such fragments include but are not limited to: the F(ab')2 fragments that can be produced by pepsin digestion of the antibody molecule and the Fab fragments that can be generated by reducing the disulfide bridges of the F(ab')2 fragments. Alternatively, Fab expression libraries may be constructed (Huse et al. 1989 *Science* 246:1275-1281) to allow rapid and easy identification of monoclonal Fab fragments with the desired specificity.

For in vitro assays, the NP, VP35, and VP24 may comprise any recombinantly produced protein, or in the case of using NP as a substrate for glycosylation, any protein that has the required motif for glycosylation. In the latter case, such NP proteins include, but are not limited to, unprocessed NP proteins in which the NP proteins have not been post-translationally modified by the addition of a sugar group. Unprocessed NP proteins may advantageously be obtained by cloning and expressing the NP gene in any of a variety of prokaryotic expression systems, using recombinant DNA techniques well known in the art (e.g., see Sambrook, 1989, supra). The NP protein expressed in such prokaryotic systems will not be processed or post-translationally modified, as they would be in eukaryotic systems. Alternatively, eukaryotic cell lines not capable of glycosylation may be used as expression hosts.

Alternatively, the NP, VP35, and VP24 may be chemically synthesized using techniques well known in the art (e.g., see Creighton 1983 *Proteins: Structures and Molecular Principles*, W.H. Freeman & Co., NY, Chapter 1).

Whether produced by molecular cloning methods or by chemical synthetic methods, the amino acid sequence of the NP, VP35, and VP24 which may be used in either the cell-based or in vitro assay of the invention need not be identical to the reported sequence of NP, VP35, and VP24. The NP, VP35, and VP24 may comprise altered sequences in which amino acid residues are deleted, added, or substituted resulting in a functionally equivalent product that serves as a substrate for assembly or glycosylation.

For example, functionally equivalent amino acid residues may be substituted for residues within the sequence resulting in a change of sequence. Such substitutes may be selected from other members of the class to which the amino acid belongs, e.g., the nonpolar (hydrophobic) amino acids include alanine, leucine, isoleucine, valine, proline, phenylalanine, tryptophan and methionine; the polar neutral amino acids include glycine, serine, threonine, cysteine, tyrosine, asparagine, and glutamine; the positively charged (basic) amino acids include arginine, lysine and histidine; the negatively charged (acidic) amino acids include aspartic and glutamic acid.

The glycosylation enzyme used in the in vitro assay may be obtained from a variety of sources. For example, the glycosylation enzyme may be isolated from any of a variety of mammalian cells, tissues or organs using purification schemes well known to those skilled in the art. Alternatively, crude lysates of cells that express the glycosylation enzyme, or fractions thereof, of cells, tissues, or organs that express the glycosylation enzyme may be utilized as a component of the assay systems. Alternatively, the glycosylation enzyme could be produced using chemical methods to synthesize the amino acid sequence in whole or in part (e.g., see Creighton, 1983, supra, pp. 34-49 and 50-60).

Cell Screening Assay

This assay detects compounds that inhibit the assembly of NP, VP35, and VP24, or that inhibit the glycosylation of NP, in cells engineered to express a substrate for assembly or glycosylation. Preferably, the test compounds are cell-permeable. The general operation involves adding a test compound to the cells to form a reaction mixture, incubating the reaction mixture for sufficient time to obtain a result, and determining whether the test compound inhibits the assembly of NP, VP35, and VP24, or the glycosylation of NP, as compared to cells in the absence of the test compound.

In one embodiment, the assay is conducted by adding a labeled sugar group or a labeled precursor of the sugar group, with and without test compound, to cells engineered to express NP, recovering the NP from the cells, and detecting whether the labeled sugar group or labeled precursor of the sugar group was incorporated into the NP recovered. The use of labeled precursors of the sugar groups allows for the detection of compounds that may inhibit the biosynthesis of sugar groups such that a selective inhibition of infectious virus formation is achieved. The use of labeled sugar groups or precursors of the sugar groups allows for detection of compounds that inhibit the attachment of sugar groups to the viral NP, such that a selective inhibition of infectious virus formation is achieved. Either the labeled precursor of the sugar groups or the labeled sugar groups may be used to detect compounds that remove sugar groups from NP, and inhibit the formation of infectious viruses.

In another embodiment, the test compound and the labeled sugar group or labeled precursor of the sugar group are added to a culture of cells engineered to express NP, VP35, and VP24. The use of these cells in the assay system offers an advantage, in that inhibition of nucleocapsid assembly can also be assayed. The use of genetically engineered cells that express NP but not VP35 or VP24 will identify only those compounds that inhibit glycosylation of NP.

In another embodiment, the assay is conducted by adding a test compound to cells engineered to express a protein selected from the group consisting of NP, VP35, and VP24, recovering the recombinantly produced protein from the cells, and detecting whether the compound binds a member of the group. Alternatively, the test compound is added to a culture of cells engineered to express all three members selected from the group consisting of NP, VP35, and VP24. The use of these cells in the assay system offers an advantage, in that inhibition of nucleocapsid assembly can also be assayed. The use of genetically engineered cells that express a protein selected from the group consisting of NP, VP35, and VP24 will identify only those compounds that inhibit glycosylation of NP or bind NP, VP35, or VP24, but the use of genetically engineered cells that express all three members selected from the group consisting of NP, VP35, and VP24 will identify inhibition of nucleocapsid assembly.

The order of addition of the test compound and the sugar group or precursor of the sugar group may be varied, e.g., simultaneous or sequential additions may be performed and can provide different information. For example, the prior addition of the test compound will identify compounds that prevent glycosylation of NP. The addition of the test compound subsequent to the addition of labeled sugar group could be used to identify compounds that remove sugar from NP. No test compound, or a placebo, is added to the controls.

After a suitable time period, NP, VP35, or VP24 is isolated from the culture. This may be accomplished by lysing the cells and isolating NP, VP35, or VP24 from the lysates with an anti-NP antibody, anti-VP35 antibody, or anti-VP24 antibody; e.g., an immobilized antibody that will capture and anchor. This system allows for rapid high throughput screening of test compounds. Alternatively, the NP, VP35, or VP24 can be isolated from the lysate by immunoprecipitation or immunoelectrophoresis (e.g., Western blot).

The presence or absence of labeled sugar groups incorporated into the isolated NP is then detected. If the test compound can prevent the glycosylation of viral NP, the NP will not incorporate the labeled sugar group and the assay will be scored by the absence of the incorporation of label. If a test compound does not inhibit NP glycosylation, the protein will incorporate the label and the labeled protein will be detected by techniques such as those described above.

In another embodiment, the presence or absence of binding of the test compound to the isolated NP, VP35, or VP24 is detected. If the test compound can bind viral NP, VP35, or VP24, the assay will be scored by the presence of such binding. If the test compound does not bind viral NP, VP35, or VP24, the unbound protein will be detected by techniques such as those described above.

In another embodiment, the presence or absence of nucleocapsid assembly is detected. If the test compound can prevent the assembly of NP, VP35, and VP24, unbound proteins will be detected by techniques such as those described above. If the test compound does not inhibit the assembly of NP, VP35, and VP24, the assay will be scored by the formation of nucleocapsids.

In Vitro Screening Assay

This assay detects compounds that inhibit the assembly of NP, VP35, and VP24, or that inhibit the glycosylation of NP, in vitro. The general principle involves adding a test compound to a reaction mixture, incubating the reaction mixture for sufficient time to obtain a result, and determining whether the test compound inhibits the assembly of NP, VP35, and VP24, or the glycosylation of NP, as compared to a reaction mixture in the absence of the test compound.

In one embodiment, the assay is conducted by adding a labeled sugar group, with and without test compound, to a reaction mixture containing NP and enzyme, recovering the NP from the cells, and detecting whether the labeled sugar group was incorporated into the NP recovered.

In another embodiment, the test compound and the labeled sugar group are added to a reaction mixture containing NP, VP35, and VP24, and enzyme. The use of this reaction mixture in the assay system offers an advantage, in that inhibition of nucleocapsid assembly can also be assayed. The use of a reaction mixture that contains NP but not VP35 or VP24 will identify only those compounds that inhibit glycosylation of NP.

In another embodiment, the assay is conducted by adding a test compound to a reaction mixture that contains a protein selected from the group consisting of NP, VP35, and VP24, recovering the recombinantly produced protein from the cells, and detecting whether the compound binds a member of the group. Alternatively, the test compound is added to a reaction mixture that contains all three members selected from the group consisting of NP, VP35, and VP24. The use of these reaction mixtures in the assay system offers an advantage, in that inhibition of nucleocapsid assembly can also be assayed. The use of a reaction mixture that contains a protein selected from the group consisting of NP, VP35, and VP24 will identify only those compounds that inhibit glycosylation of NP or bind NP, VP35, or VP24, but the use of a reaction mixture that contains all three members selected from the group consisting of NP, VP35, and VP24 will identify inhibition of nucleocapsid assembly.

As explained in the cell based assay systems, the order of addition of the test compound relative to the reactants may be varied to distinguish compounds that act by inhibiting or preventing glycosylation, and those that disrupt or remove sugars from NP.

After a suitable time period, NP, VP35, or VP24 is isolated from the reaction mixture. This may be accomplished by isolating NP, VP35, or VP24 from the reaction mixture with an anti-NP antibody, anti-VP35 antibody, or anti-VP24 antibody; e.g., an immobilized antibody that will capture and anchor. This system allows for rapid high throughput screening of test compounds. Alternatively, the NP, VP35, or VP24 can be isolated from the reaction mixture by immunoprecipitation or immunoelectrophoresis (e.g., Western blot).

The presence or absence of labeled sugar groups incorporated into the isolated NP is then detected. If the test compound can prevent the glycosylation of viral NP, the NP will not incorporate the labeled sugar group and the assay will be scored by the absence of the incorporation of label. If a test compound does not inhibit NP glycosylation, the protein will incorporate the label and the labeled protein will be detected by techniques such as those described above.

In another embodiment, the presence or absence of binding of the test compound to the isolated NP, VP35, or VP24 is detected. If the test compound can bind viral NP, VP35, or VP24, the assay will be scored by the presence of such binding. If the test compound does not bind viral NP, VP35, or VP24, the unbound protein will be detected by techniques such as those described above.

In another embodiment, the presence or absence of nucleocapsid assembly is detected. If the test compound can prevent the assembly of NP, VP35, and VP24, unbound proteins will be detected by techniques such as those described above. If the test compound does not inhibit the assembly of NP, VP35, and VP24, the assay will be scored by the formation of nucleocapsids.

In yet another embodiment of the invention, the NP, VP35, or VP24 may be immobilized prior to the addition of the test compound. To this end, a solution of the NP, VP35, or VP24 can be used to coat a solid support. Alternatively, an antibody may be used to coat the support in order to anchor the NP, VP35, or VP24. The ability of the immobilized NP, VP35, or VP24 to incorporate label sugar in the presence of the test compound is scored by the retention of the label by the protein. Alternatively, the ability of immobilized NP, VP35, or VP24 to bind a labeled test compound is scored in a binding assay. The presence or absence of labeled NP, VP35, or VP24 will be detected by autoradiographic analysis of the immobilized component. The evaluation of the test compound is by reference to a control experiment in which the test compound is not added.

Treatment of Filovirus Infection Using Compounds that Inhibit Virus Assembly

The particular compound that inhibits NP glycosylation or viral nucleocapsid assembly can be administered to a patient at therapeutically effective doses. A therapeutically effective dose refers to that amount of the compound sufficient to result in amelioration of symptoms of viral infection.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design the delivery system that targets such compounds to the site of infection in order to minimize damage to uninfected cells and reduce side effects.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in a conventional manner using one or more physiologically acceptable carriers or excipients.

Thus, the therapeutic compounds and their physiologically acceptable salts and solvates may be formulated for administration by inhalation or insufflation (either through the mouth or the nose) or for oral, buccal, parenteral or rectal administration.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of a therapeutic compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropylmethyl cellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry-product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

The therapeutic compounds may be formulated for parenteral administration by injection e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The therapeutic compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the therapeutic compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example, comprise metal or plastic foil, such as a blister pack. The pack or dispenser device may be accompanied by instructions for administration.

Assays for Compounds that Inhibit Glycosylation of Other Proteins Having a Glycosylation Domain that is Substantially Homologous to a Glycosylation Domain of NP Required for Polymerization In another embodiment, the invention relates to the identification and use of compounds that inhibit the glycosylation of other proteins (e.g., Tau) having a glycosylation domain that is substantially homologous to a glycosylation domain of NP required for polymerization. The assays described above to identify compounds that inhibit glycosylation of NP may be analogously applied to identify compounds that inhibit glycosylation of these other proteins (e.g., Tau). Inhibitory compounds that are relatively non-toxic, e.g., display a good therapeutic index, may be utilized as agents for the treatment of diseases (e.g., neurodegenerative diseases) mediated by polymerization due to glycosylation of these proteins (e.g., Tau) in animals, including humans.

As used herein, two proteins (or a region of the proteins) are substantially homologous when the amino acid sequences are at least about 15-20%, 20-50%, 50-70%, typically as least about 70-75%, more typically at least about 80-85%, and most typically at least about 90-95% or more homologous. As a practical matter, whether any particular polypeptide (or a region of the polypeptide) is substantially homologous to, for instance, the amino acid sequence of NP shown in GenBank Accession No. AF272001 (or a region of the amino acid sequence) can be determined conventionally using known computer programs such as Vector NTI alignment to do a comparison under the default parameters.

Figure 7A:
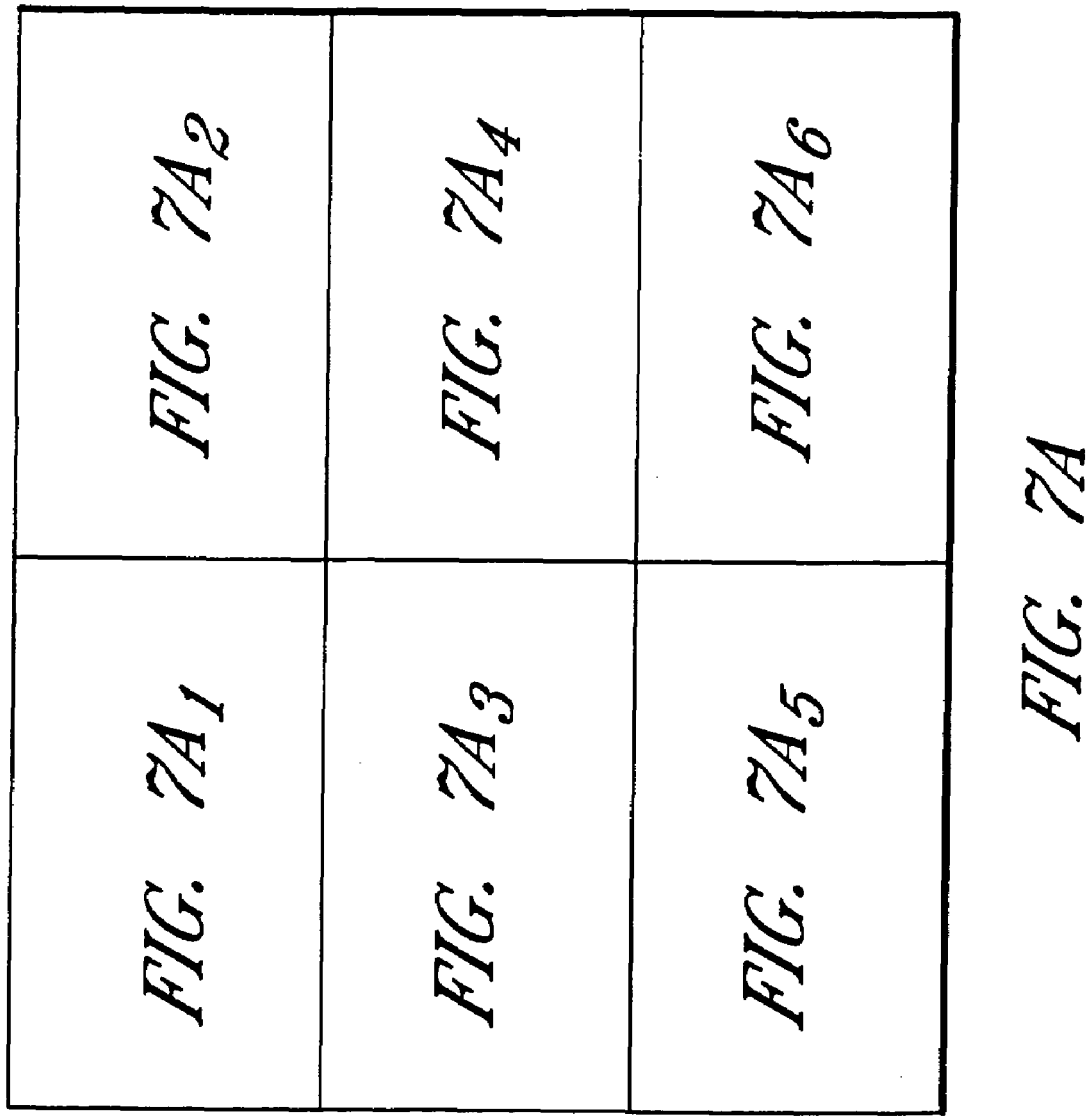
FIG. 7 A1-A6, B1-B6, C1-C6, D1-D5 compares Ebola NP with four clones of Human Tau (SEQ ID NO: 23, 24, 25, and 27; GenBank Accession Nos: P19332, P10636, P10637, and BC000558, respectively) and one Bovine Tau (SEQ ID NO: 26, GenBank Accession No: AAA51609). Ebola NP is from GenBank Accession No. AF272001 (SEQ ID NO: 28). SEQ ID NO: 29-consensus sequence.
Figure 7C:
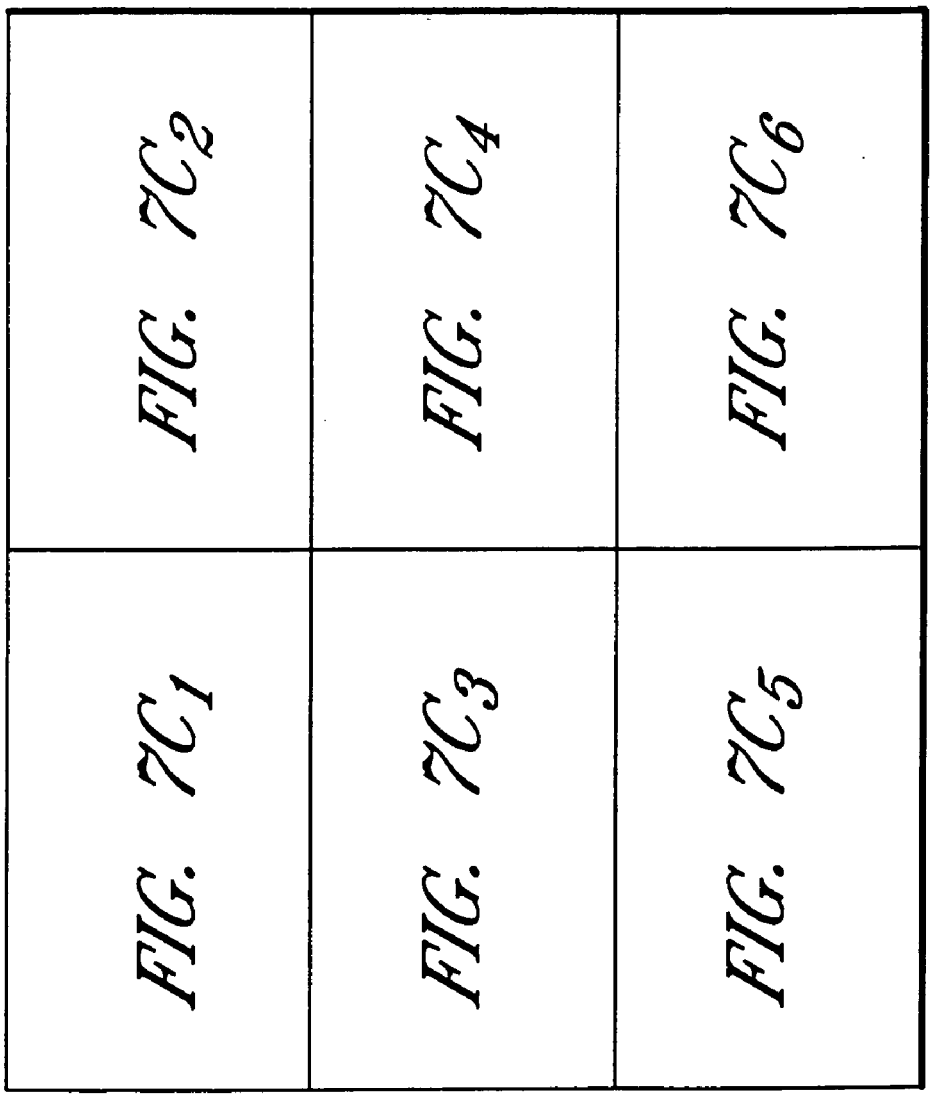
Figure 7D:
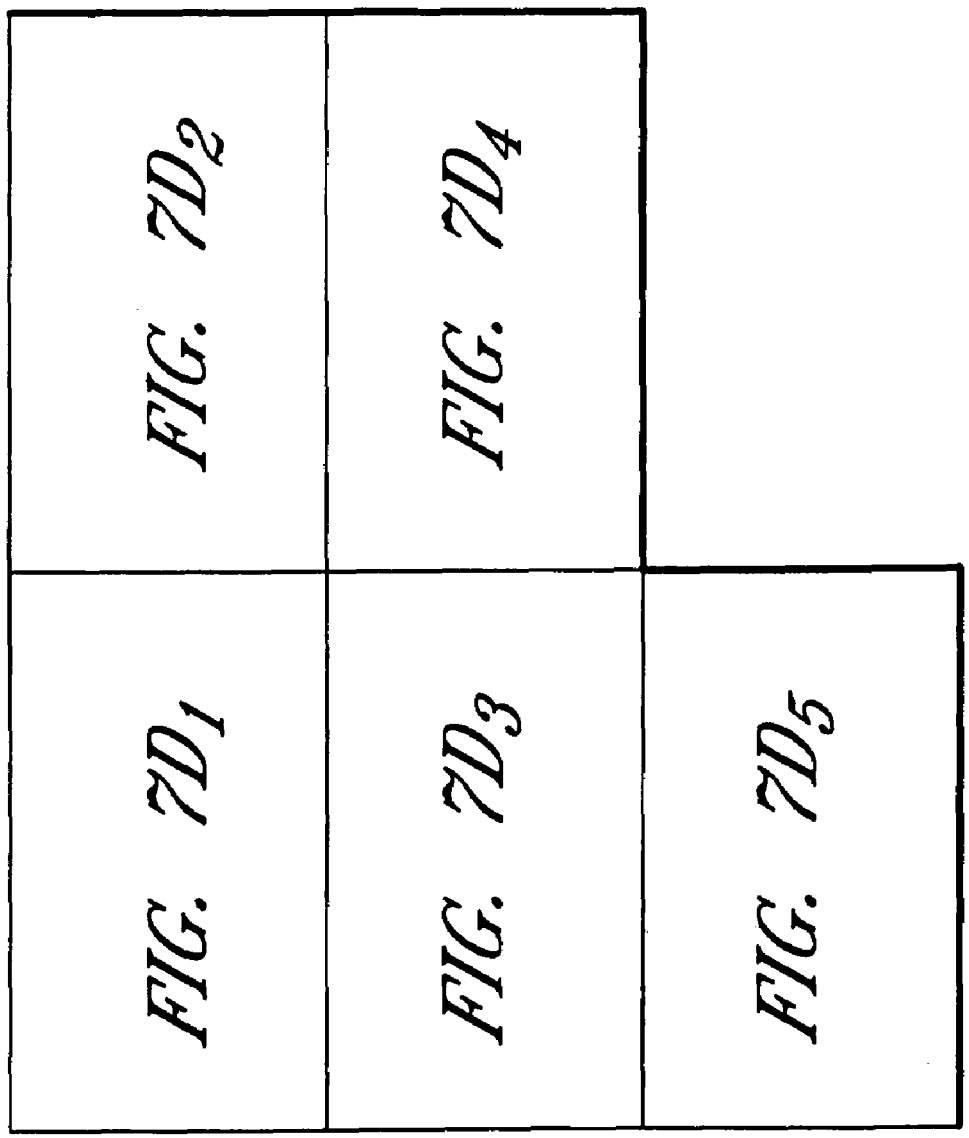

Comparison of Ebola NP (GenBank Accession No. AF272001) with four clones of Human Tau (GenBank Accession Nos: P19332, P10636, P10637, BC000558) and one Bovine Tau (GenBank Accession No. AAA51609) reveals that a glycosylation domain of NP is substantially homologous to a region that is present in Tau. FIG. 7. The homology region is amino acid 401 to 739 of NP and Tau's C-terminal domain. The comparison shows about 18.2% homology and 11.3% identity with Tau-BC000558. Accordingly, a sequence substantially homologous to a glycosylation domain in NP is present in Human Tau. Consequently, the invention also relates to assays for the identification of compounds that block glycosylation of proteins, like Tau, having a glycosylation domain that is substantially homologous to a glycosylation domain of NP required for polymerization for use in treatment of diseases mediated by polymerization due to glycosylation of these proteins, like diseases mediated by Tau, such as neurodegenerative diseases, e.g., Alzheimer's disease.

Mechanism of Ebola Virus Assembly

The assembly of Ebola virus nucleocapsid requires virion associated proteins 35 and 24 and post-translational modifications of nucleoprotein.

Assembly of Ebola in Human 293T Cells from Recombinant cDNAs

Figure 1B:
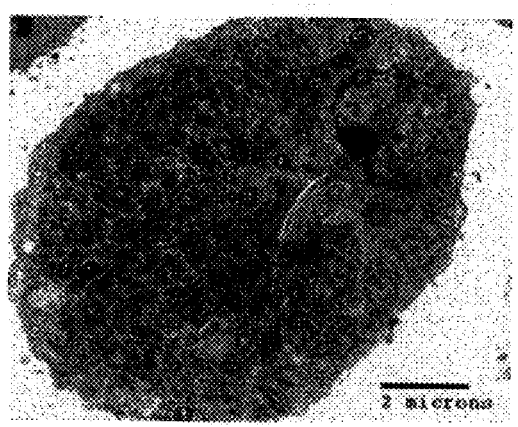

To determine whether Ebola capsids could assemble in a cell line expressing the appropriate recombinant viral cDNA gene products, expression vectors encoding multiple viral genes were co-transfected into the highly transfectable 293 human renal epithelial cell line. When six plasmids, encoding Ebola GP, NP, VP40, VP35, VP30, and VP24 respectively (FIG. 1A) were co-transfected, substantial accumulation of intracellular Ebola virus-like particles was observed by TEM (FIG. 1B). Aggregates of well-formed tubular viral nucleocapsids were seen within the cytoplasm of transfected cells. The structures are similar to infectious virions produced from Vero cells (Geisbert, T. W. and Jahrling, P. B. 1995 *Virus Res* 39:129-150).

Figure 1C:
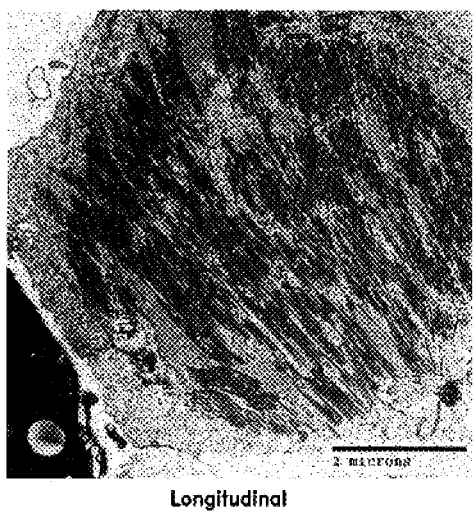

Co-expression of NP, VP35, VP30, and VP24 retained the ability to support capsid formation (FIG. 1C, D), as evidenced by the presence of filamentous strands in cross-section, or bundled hexamers in longitudinal sections. The length of the particles ranged from 1-4 μm (FIG. 1C). The cross-sectional diameter appeared uniform, approximately 45-50 nm (FIG. 1D), similar to that of Ebola virus described in previous ultrastructural studies (Geisbert, T. W. and Jahrling, P. B. 1995 *Virus Res* 39:129-150; Zaki, S. R. and Goldsmith, C. S. 1999 in: *Current Topics in Microbiology and Immunology*, H.-D. Klenk, ed. New York: Springer, pp. 97-116). The absence of the negative strand viral genomic RNA and viral RNA polymerase (L) from the cells indicated that they were not essential for the formation of Ebola nucleocapsid.

NP, VP35 and VP24 are Necessary and Sufficient for Ebola Assembly

To examine the minimum gene requirements for capsid assembly, different combinations of viral genes were systematically analyzed in transfection studies. Formation of the nucleocapsid structure did not occur in the absence of VP24, VP35 or NP (Table 1). No gene product alone, nor any combination of two, supported assembly, indicating that all three proteins were necessary for capsid assembly (Table 1). Similar levels of NP were detected in the presence or absence of other cotransfected genes, suggesting that NP protein expression was not sufficient for capsid assembly.

TABLE 1

Examination of viral capsid formation by scanning TEM
CO-TRANSFECTION OF EBOLA GENES FOR VIRAL
CAPSID FORMATION

| EBOLA GENES | | | | | | CAPSID |
| --- | --- | --- | --- | --- | --- | --- |
| NP | VP35 | VP40 | VP30 | VP24 | GP | FORMATION |
| + | + | + | + | + | + | + |
| + | + | + | + | + | − | + |
| + | + | + | − | + | − | + |
| + | + | + | + | − | − | − |
| + | + | − | + | + | − | + |
| + | + | − | − | + | − | + |
| + | + | + | − | − | − | − |
| + | + | − | + | − | − | − |
| + | + | − | − | − | − | − |
| + | − | + | − | − | − | − |
| + | − | − | + | − | − | − |
| + | − | − | − | + | − | − |
| − | + | + | − | − | − | − |
| + | − | − | − | − | − | − |

$3 \times 10^6$ 293T cells were transfected with the plasmids containing indicated genes as described below. The presence of specific viral genes (left) and formation of nucleocapsids by scanning TEM (right) is indicated (+ or −).

To characterize the Ebola capsids in 293T cells transfected with NP, VP35, and VP24 further, we performed buoyant density gradient sedimentation. The preformed nucleocapsid core failed to bud from the transfected cells, but was released from transfected 293T cells that were frozen and thawed (FIG. 2A). Fractions from a gradient of clarified cell lysates obtained after three freeze-thaw cycles were analyzed by Western blot analysis, and the peak of activity was detected at a density of 1.16-1.18 g/ml (FIG. 2B, lane 11), comparable but slightly less buoyant than previously described intact virions of 1.14 g/ml (Kiley, M. P. et al. 1988 *J Gen Virol* 69:1956-1967). By this analysis, NP and VP35 were found to be the major components in the particle, raising the possibility that VP24 catalyzed particle formation but remained more weakly associated (FIG. 2B, lanes 1 to 13). This finding is similar to those with purified Marburg virus used to isolate the nucleocapsids (Becker, S. et al. 1998 *Virology* 249:406-417).

Role of Specific Domains of NP in Particle Formation

The role of specific domains in the NP gene for Ebola capsid assembly was analyzed by using deletion mutations (FIG. 2C). Expression of these NP mutants was confirmed by Western blotting (FIG. 2D). Despite comparable levels of protein synthesis, deletion of the NP $NH_2$-terminal and middle regions abolished capsid assembly, and removal of the 234 amino acids from the COOH-terminus modified the shape of the assembled capsids (FIG. 2E, left), indicating that most of the NP coding region is essential for particle formation.

Post-translational Modification of NP is Required for NP-VP35 Interaction

The interactions among NP, VP35, and VP24 were examined by co-immunoprecipitation of these proteins following in vitro transcription and translation. VP35 and VP24 could be co-immunoprecipitated with an anti-NP antibody (FIG. 3A, lanes 6-8), indicating that NP interacts directly with the two proteins. VP24 co-immunoprecipitated with NP and VP35 more weakly in vitro (FIG. 3A, lane 6), and it did not co-distribute with them in buoyant density sedimentation fractions (FIG. 2B), suggesting that it may play an important role in formation of the NP-VP35 complex during capsid formation, but may not be as stably incorporated into viral capsids.

Although the Ebola NP gene encodes 739 amino acids, with a calculated molecular weight of 83 kDa, its migration by SDS-PAGE is consistent with a molecular weight of approximately 115 kDa. While the protein may undergo phosphorylation that might slightly increase its apparent molecular weight (MW), the possibility existed that another modification, such as glycosylation, accounted for this large size difference (Elliott, L. H. et al. 1985 *Virology* 147:169-176; Kiley, M. P. et al. 1988 *J Gen Virol* 69:1956-1967; Becker, S. et al. 1994 *J Gen Virol* 75:809-818). O-linked N-acetylglucosamine (O-GlcNAc) has been found in the nucleus and cytoplasm of eukaryotic cells. Rabbit reticulocyte lysates contain sufficient enzymes and cofactors to glycosylate translated products efficiently (Starr, C. M. and Hanover, J. A. 1990 *J Biol Chem* 265:6868-6873; Roquemore, E. P. et al. 1994 *Meth Enzymol* 230:443-460). We hypothesized that NPs translated from reticulocyte and *E. coli* expression systems should differ in their electrophoretic mobility. To test this hypothesis, we performed in vitro translation and analyzed NP post-translational modification as well as its interaction with VP35 and VP24. As expected, NP translated in the reticulocyte system was of higher MW than that translated from the *E. coli* S30 system (≧20 kDa), though both NPs were able to immunoprecipitate with anti-NP serum (FIG. 3B, lanes 13, 14). However, NP derived from the reticulocyte system was able to co-precipitate with VP35 whereas NP translated from *E. coli* S30 extracts did not interact with VP35 (FIG. 3C, lanes 17, 19, 21). These findings suggest that NP is extensively altered by post-translational modification, and this change is necessary for the interaction of NP with VP35 and VP24 required for particle formation.

Deglycosylation enzymes were used to digest the His-tagged purified NP from transfected 293 cells. After treatment, the migration of NP was altered, and a prominent band appeared on the gel consistent with a molecular weight of 85 kDa, as detected by polyclonal anti-NP antisera (FIG. 4A, lanes 3, 5). This effect was observed under both denaturing and non-denaturing conditions. Further analysis showed that treatment with α2-3,6,8,9 neuramimidase alone could produce a similar effect (FIG. 4B, lane 7), indicating the presence of sugars containing terminal sialic acid. The presence of additional lower molecular weight bands suggests possible contamination or sensitivity to other enzymes in the digestion reaction, for example, proteases. Treatment with N-acetylglucosidase or N-glycosidase failed to reduce the size of the band generated by neuramimidase. No effect was observed when NP-transfected 293 cells were incubated with tunicamycin and deoxymannojirimycin (dMM), and migration of this band did not change after digestion in vitro with endoglycosidase H (Endo H), suggesting that NP was primarily O-glycosylated rather than N-linked (FIG. 4B, lanes 9-11). This finding was again confirmed in vivo by treatment of NP-transfected 293 cells with tunicamycin, where synthesis of NP was unaffected at concentrations that abolished expression of HIV gp160 (FIG. 4C), which shows a high degree of N-linked glycosylation. In addition, point mutation of the four consensus N-linked glycosylation sites did not alter NP migration by SDS-PAGE.

The glycosylation of NP was further confirmed by $^3$H-glucosamine labeling. Glucosamine is converted by cells into N-acetyl-galactosamine (GalNAc), N-acetyl-neuraminic acid (sialic acid), and N-acetyl-glucosamine (GlcNAc). NP in transfected cells incorporated $^3$H-glucosamine and $^3$H-galactose at levels 53-fold and 18-fold higher than $^3$H-thymidine (FIG. 4D, left panel). These labels were immunoprecipitated with antibodies to NP, in contrast to $^3$H-thymidine (FIG. 4D, middle, lane 1), despite comparable levels of NP proteins detected by silver staining (FIG. 4D, right, lane 4).

To confirm the specificity of these carbohydrate moieties in NP, a lectin pull-down assay was performed. The following lectins were used for analysis: *Arachis hypogaea* (peanut) agglutinin (PNA), which recognizes unsubstituted galactose β(1-3)N-acetylgalactosamine cores in O-glycans; *Datura stramonium* agglutinin (DSA), which binds specifically to galactose β(1-4) glucosamine in complex or in hybrid type glycans; *Galantus nivalis* agglutinin (GNA), which recognizes terminal mannose-linked α(1-3)-, α(1-6)- or α(1-2)-mannose found in N-glycans; *Maackia amurensis* agglutinin (MAA) or *Sanbucus nigra* agglutinin (SNA) which react specifically with α(2-3)-linked or α(2-6)-linked sialic acids, respectively. After washing vigorously four times, NP reacted with four out of five lectins by Western blot analysis (FIG. 4E, lanes 8, 9, 10, 12). The strong reactions to MAA and SNA confirmed the presence of sialic acid on NP. It also reacted with DSA, indicating that NP may contain individual N-acetyl-glucosamine residues with O-glycosidic links to serine or threonine. The failure to react with PNA demonstrated that the disaccharide, galactose (1,3)-acetylgalactosamine, was well-substituted with sialic acid. The weakest reaction to NP was observed with the mannose-specific lectin, GNA.

Pharmacologic Inhibition of the NP/VP35 Interaction

Figure 5A:
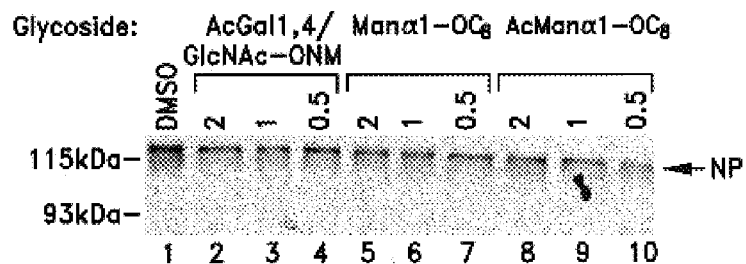
FIG. 5 shows that a synthetic glycoside inhibits the biochemical interaction associated with nucleocapsid formation in vitro. A. Effect of the indicated concentrations of specific glycoside analogues on the transcription/translation of NP, determined as in FIG. 5B. DMSO (2%) was used at the highest concentration as in the diluent for the synthetic glycoside as a negative control (lane 1). B. Inhibition of NP/VP35 interaction by Manα1-OC$_8$ by immunoprecipitation with anti-VP35 with in vitro transcribed/translated NP, VP35 and VP24, as described in FIG. 5C. DMSO was used as defined in panel A. Control refers to the use of normal mouse serum in the immunoprecipitation at the same concentration as anti-VP35 (5 μl) as a negative control. C. Quantitation of inhibition by Manα1-O-octyl. Image intensity from the indicated inhibitors in FIG. 8B (square, Manα1-OC$_8$; triangle, Ac Manα1-OC$_8$; diamond, AcGal1,4 GlcNAc-ONM; circle, DMSO) was determined from phosphorimaging relative to the DMSO control (0% inhibition).
Figure 5B:
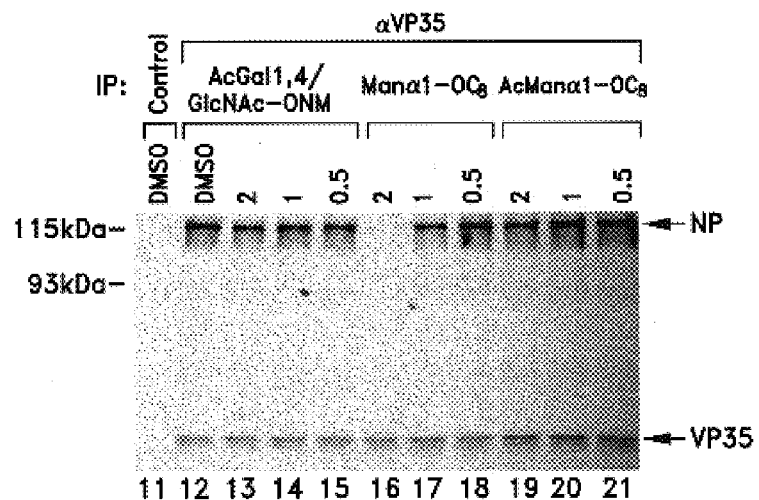
Figure 5C:
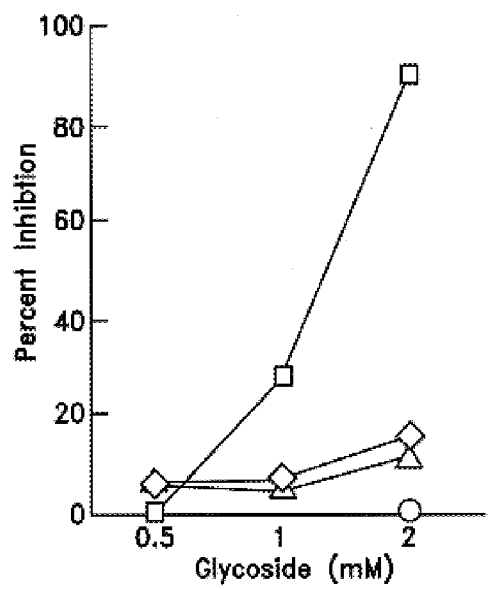

The reactivity of NP with several carbohydrate-specific lectins raised the possibility that this post-translational modification was required for the formation of the nucleocapsid. To test this hypothesis, several potential inhibitors of serine/threonine sites and/or cytoplasmic glycosylation were tested for their ability to inhibit the interaction of NP with VP35 using in vitro transcription/translation and immunoprecipitation with antisera to VP35. Among the compounds tested, none affected the synthesis of modified NP in rabbit reticulocyte lysates in vitro as determined by SDS-PAGE (FIG. 5A, lanes 2-10), though minor changes in molecular weight would not be detected by this method. In the association assay (FIG. 5B), one synthetic glycoside, mannose α1-O-octyl (Manα1-OC$_8$) substantially reduced the interaction of NP with VP35 at 2 mM (FIG. 5B, lane 16). This inhibition was specific, not seen with the acetylated version of this compound, AcManα1-OC$_8$ (FIG. 5B, lanes 19-21), and the effect was dose-dependent as determined by quantitative densitometry (FIG. 5C). Addition of Manα1-OC$_8$ after the in vitro translation of NP, just prior to incubation with VP35/24, did not inhibit the interaction, suggesting that the synthetic glycoside modifies post-translational glycosylation, disrupting critical determinants required for binding to VP35. This compound may therefore function as a prototype to develop antiviral agents that inhibit Ebola virus assembly.

Minimum Requirements of Ebola Viral Proteins for Capsid Assembly

Figure 1D:
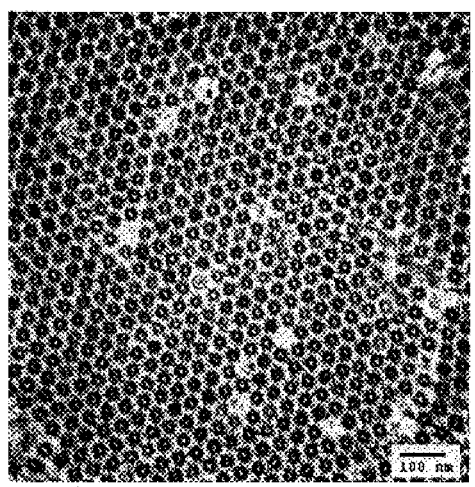
Figure 2A:
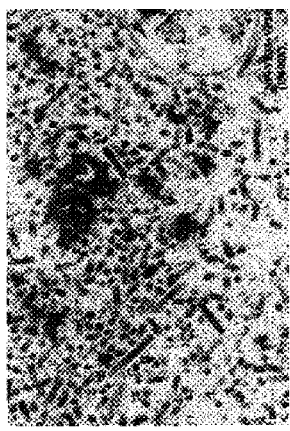
FIG. 2 shows release of assembled capsids from transfected 293T cells and TEM analysis of NP mutants for Ebola capsid assembly in transfected 293T cells. A. Electron micrograph of the lysis of 293T cells transfected with NP, VP35, and VP24 (magnification×19,600). 3×10$^6$ 293T cells were transfected with 3 μg of each of plasmids encoding for NP, VP35 and VP24. Three days after transfection, the cells were analyzed as described in Table 1, legend. B. Gradient sedimentation and Western blot analysis of assembled capsids. C. Schematic representation of NP mutants. A.A., amino acids. Plain areas denote that the amino acid sequences were deleted. D. Western blot analysis of the expression of NP deletion mutants. The cell lysates from 293T cells transfected with NP and different mutant NPs were extracted with RIPA (radioimmunoprecipitation assay) buffer, separated with 4-15% of SDS-PAGE, transferred onto an Immobilon™-P membrane and blotted with polyclonal anti-NP antibody (Ab). E. TEM analysis of capsid assembly of NP mutants (magnification from left to right-×40,000; ×30,000; ×20,000). 293T cells were co-transfected with 3 μg of each NP mutant, 3 μg of VP35 and VP24. Three days after transfection, TEM analysis was performed as described in Table 1, legend.
Figure 2B:
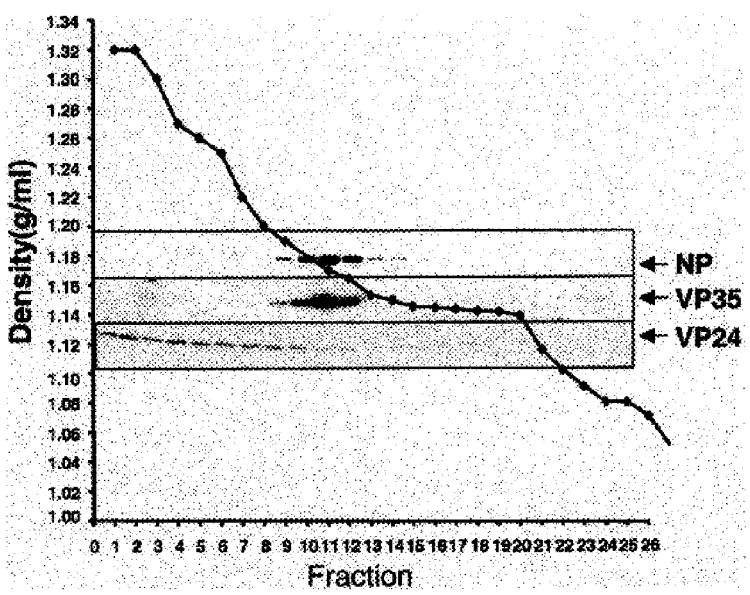
Figure 2C:
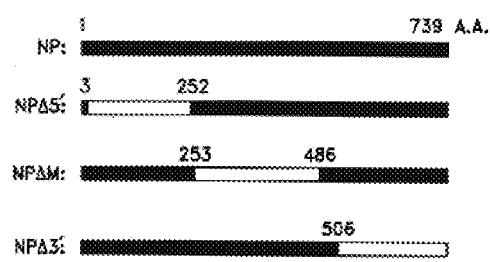
Figure 2D:
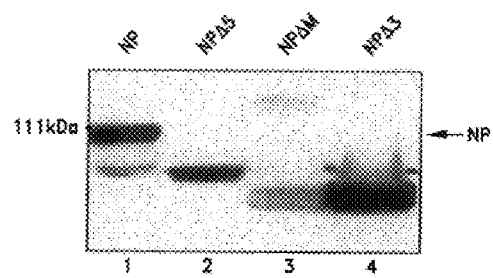
Figure 2E:
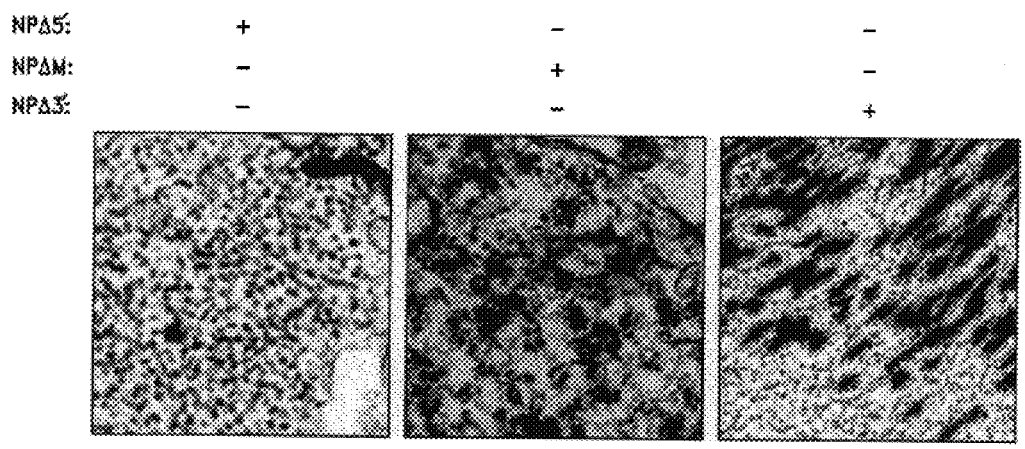
Figure 3A:
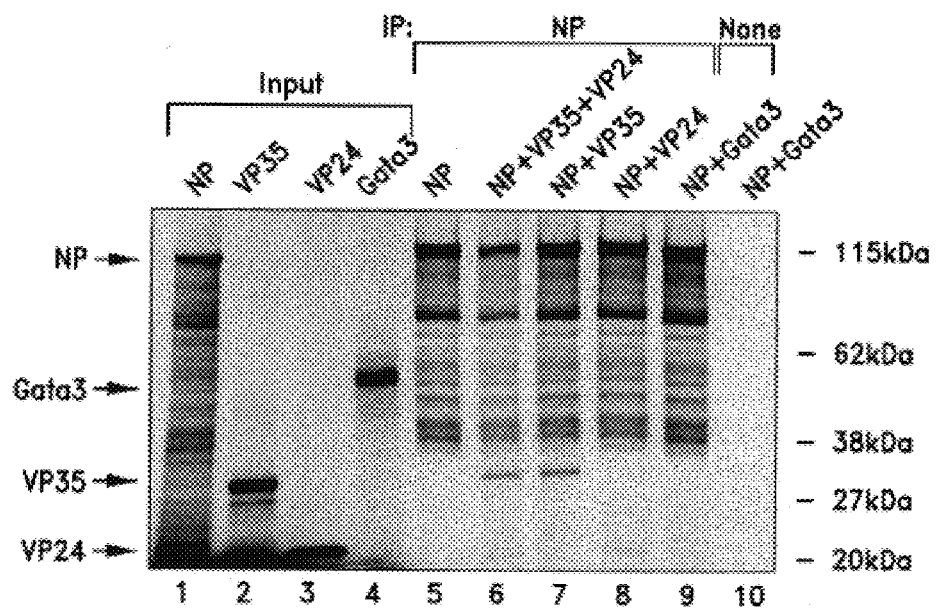
FIG. 3 shows immunoprecipitation analysis of NP, VP35 and VP24 interaction. A. Co-immunoprecipitation of VP35 and VP24 with NP. Human transcription factor Gata3 was used as an internal control. B. Immunoprecipitation of in vitro translated NP by anti-NP Ab. NPs in vitro translated either by reticulocytes lysate or *E. coli* S30 extract systems were immunoprecipitated by a polyclonal anti-NP Ab and protein G agarose. C. Immunoprecipitation of glycosylated or deglycosylated NP by anti-VP35 Ab. Glycosylated or deglycosylated NP in vitro translated either by reticulocytes lysate or *E. coli* S30 extract systems were co-immunoprecipitated by a polyclonal anti-VP35 Ab.
Figure 3B:
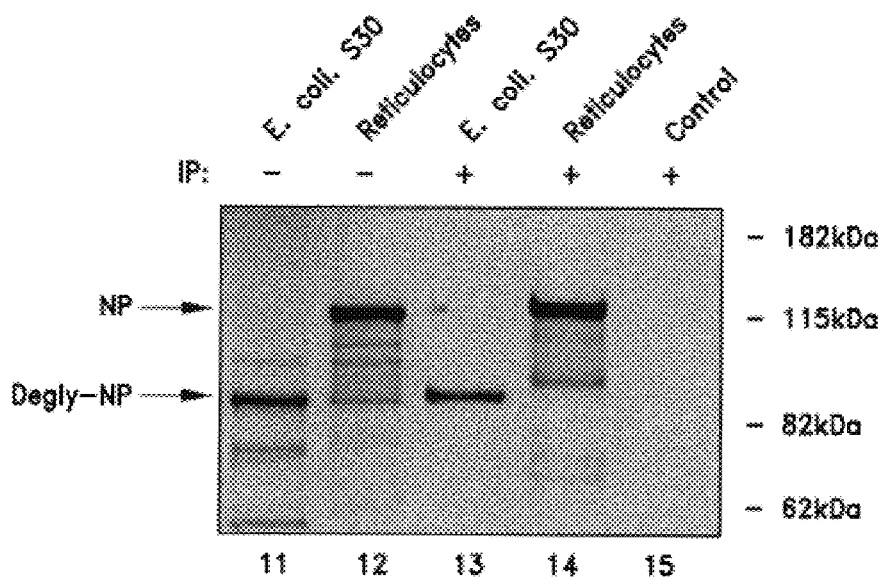
Figure 3C:
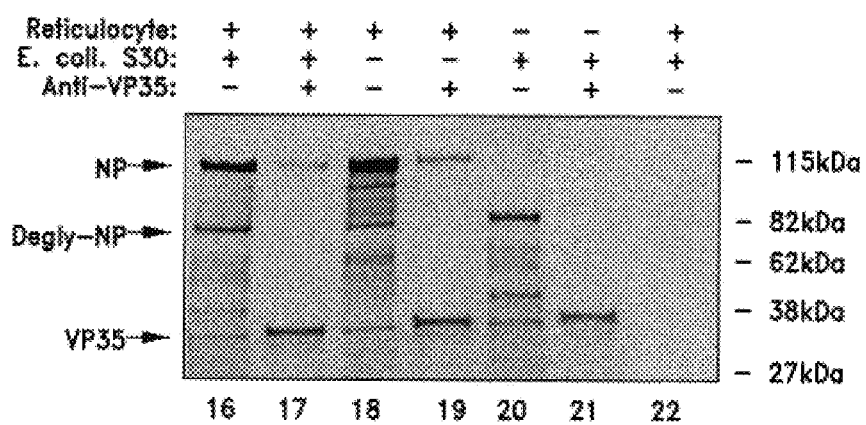

In this disclosure, we have shown that Ebola viral nucleocapsids are efficiently produced in 293T cells transfected with expression vectors encoding three viral gene products: NP, VP35 and VP24. In this transfected human cell line, Ebola capsids assembled in the cytoplasm and formed filamentous structures similar to the intact virus (FIG. 1B-D). Co-transfection of NP, VP35 and VP24 supported capsid formation, and omission of any one of these three genes abolished the effect, demonstrating that they are necessary and sufficient for viral particle formation. In the assembly of retroviruses and lentiviruses, expression of the Gag precursor polyprotein is sufficient to assemble virion-like particles (Gheysen, D. et al. 1989 *Cell* 59:103-112; Delchambre, M. et al. 1989 *EMBO J* 8:2653-2660; Luo, L. et al. 1994 *Virology* 205:496-502; Smith, A. J. et al. 1993 *J Virol* 67:2266-2275; Wills, J. W. et al. 1989 *J Virol* 63:4331-4343; Huang, Y. et al. 2001 *J Virol* 75:4947-4951). In this regard, Ebola viral assembly differs in several respects from other negative-strand viruses and retroviruses (Garoff, H. et al. 1998 *Microbiol Mol Biol Rev* 62:1171-1190). Such studies in retroviral and lentiviral models have led to the successful generation of HIV-1 particles in vitro and greater knowledge of HIV capsid biogenesis and structure.

The observations related to Ebola virus expression and NP post-translational modification may promote a better understanding of filovirus assembly. Previous studies have suggested that VP40, a viral matrix protein, plays a role in the formation of mature virus (Ruigrok, R. W. et al. 2000 *J Mol Biol* 300:103-112; Dessen, A. et al. 2000 *EMBO J.* 19:4228-4236). A careful examination of these structures reveals that VP40 facilitates the formation of hollow tubular membranes that may facilitate the formation of the surrounding envelope (Jasenosky, L. D. et al. 2001 *J Virol* 75:5205-5214; Timmins, J. et al. 2001 *Virology* 283:1-6; Martin-Serrano, J. et al. 2001 *Nat Med* 7:1313-1319), but there is no evidence that VP40 contributes to the generation of the filamentous viral capsid.

Post-translational Modification of Ebola NP is Required for Viral Assembly

There is increasing evidence that glycan structures play important roles in differential protein-protein interaction and immune responses (Han, I. and Kudlow, J. E. 1997 *Mol Cell Biol* 17: 2550-2558; Wells, L. et al. 2001 *Science* 291:2376-2378; Lowe, J. B. 2001 *Cell* 104:809-812; Moody, A. M. et al. 2001 *Cell* 107:501-512; Hanover, J. A. 2001 *FASEB J* 15:1865-1876). Here, we have found a novel role for O-glycosylation and sialation of Ebola NP, showing that it is required for the interaction of NP and VP35. The importance of NP and VP35 in viral replication has been shown previously in artificial replication assays (Muhlberger, E. et al. 1998 *J Virol* 72:8756-8764; Muhlberger, E. et al. 1999 *J Virol* 73:2333-2342), and though its involvement in capsid formation has not been previously shown, VP35 is also tightly associated with Ebola viruses produced from infected cells (Becker, S. et al. 1998 *Virology* 249:406-417). The interactions of analogues of these proteins, N(NP) and P protein, have been seen in paramyxo-, rhabdo- and bornaviruses, where they also play essential roles in their replication (Huber, M. et al. 1991 *Virology* 185:299-308; Horikami, S. M. et al. 1992 *J Virol* 66:4901-4908; Schwemmle, M. et al. 1998 *J Biol Chem* 273:9007-9012). We envision that this similarity is also related to their roles in capsid assembly for these viruses.

It is not clear how Ebola virus is released from cells during infection. Based on ultrastructure, apparent budding structures have been defined in infected cells and in tissues from patients (Geisbert, T. W. and Jahrling, P. B. 1995 *Virus Res* 39: 129-150; Zaki, S. R. and Goldsmith, C. S. 1999 in: *Current Topics in Microbiology and Immunology*, H.-D. Klenk, ed. New York: Springer, pp. 97-116); however, no budding or extracellular particles were observed here in 293 cells transfected with plasmids. This finding could reflect the fact that the transfected cells lack cellular factors or viral proteins, such as VP40, that are required for budding. The possibility remains, however, that the release of Ebola virus progeny could proceed through an alternative mechanism, such as cell lysis. A previous study has shown that Ebola virus infection of macrophages is associated with budding into the ER (Feldmann, H. et al. 1996 *J Virol* 70:2208-2214), consistent with this alternative.

Conserved Domains and Common Mechanisms of Viral Assembly

Figure 6A:
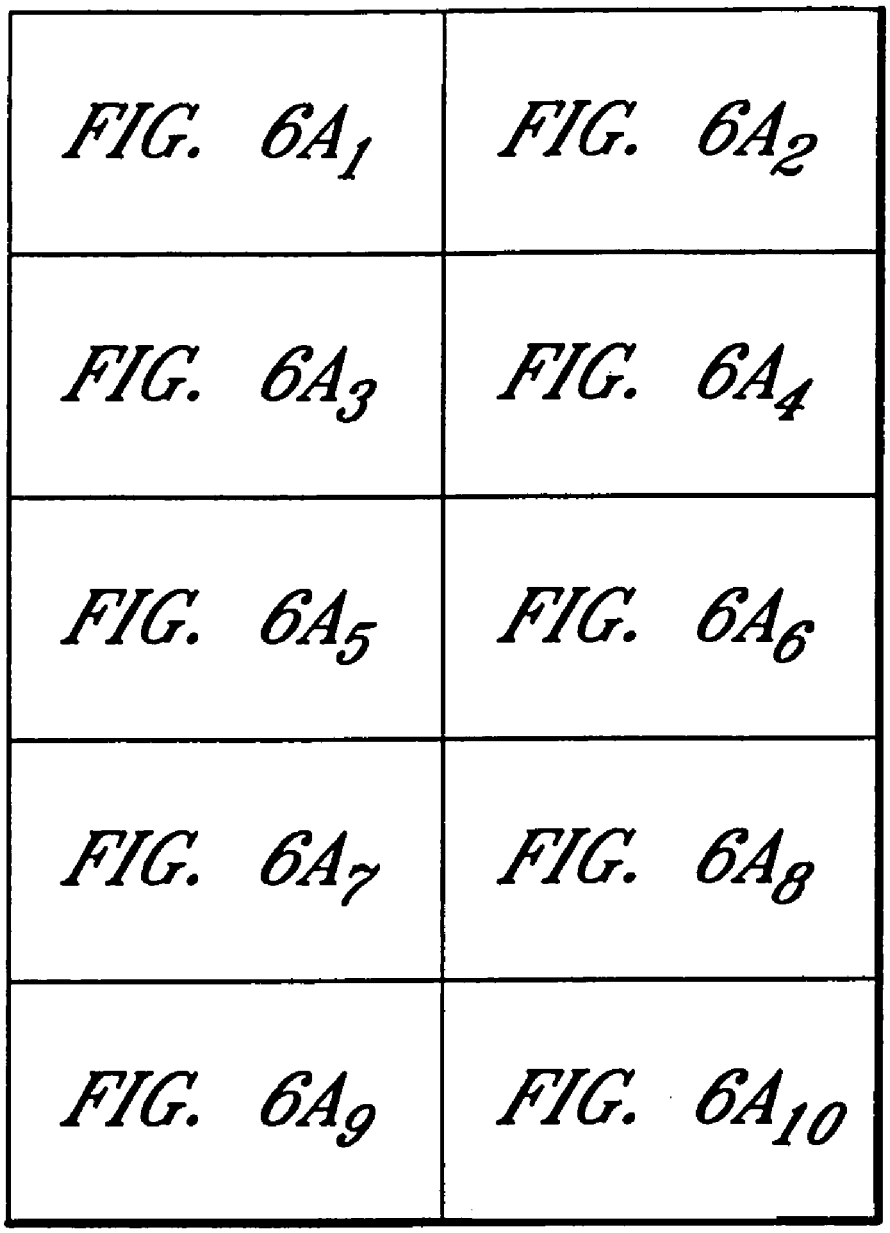
FIG. 6 shows amino acid similarity of filoviruses and paramyxovirus nucleoproteins. A1-A10. Sequence alignments of Ebola NP with related proteins from different strains and with other viruses (EBV-P, SEQ ID NO: 6; EBV-B, SEQ ID NO: 7; EBV-G, SEQ ID NO: 8; EBV-M, SEQ ID NO: 9; EBV-Z, SEQ ID NO: 10; MBV-V, SEQ ID NO: 11; MBV-P, SEQ ID NO: 12; MBV-O, SEQ ID NO: 13; consensus sequence, SEQ ID NO: 14; C-distemper, SEQ ID NO: 15; Measles, SEQ ID NO: 16; Rinderpest, SEQ ID NO: 17; Consensus sequence, SEQ ID NO: 18). B. Highly conserved motif of nucleoproteins from different filoviruses and paramyxoviruses (fragments of SEQ ID Nos: 6, 7, 8, 9, 10, 11, 112, 13, 15, 16 and 17; and Sendai, SEQ ID NO: 19; Mumps, SEQ ID NO: 20; hRSV, SEQ ID NO: 21; consensus sequence, SEQ ID NO: 22).
Figure 6B:
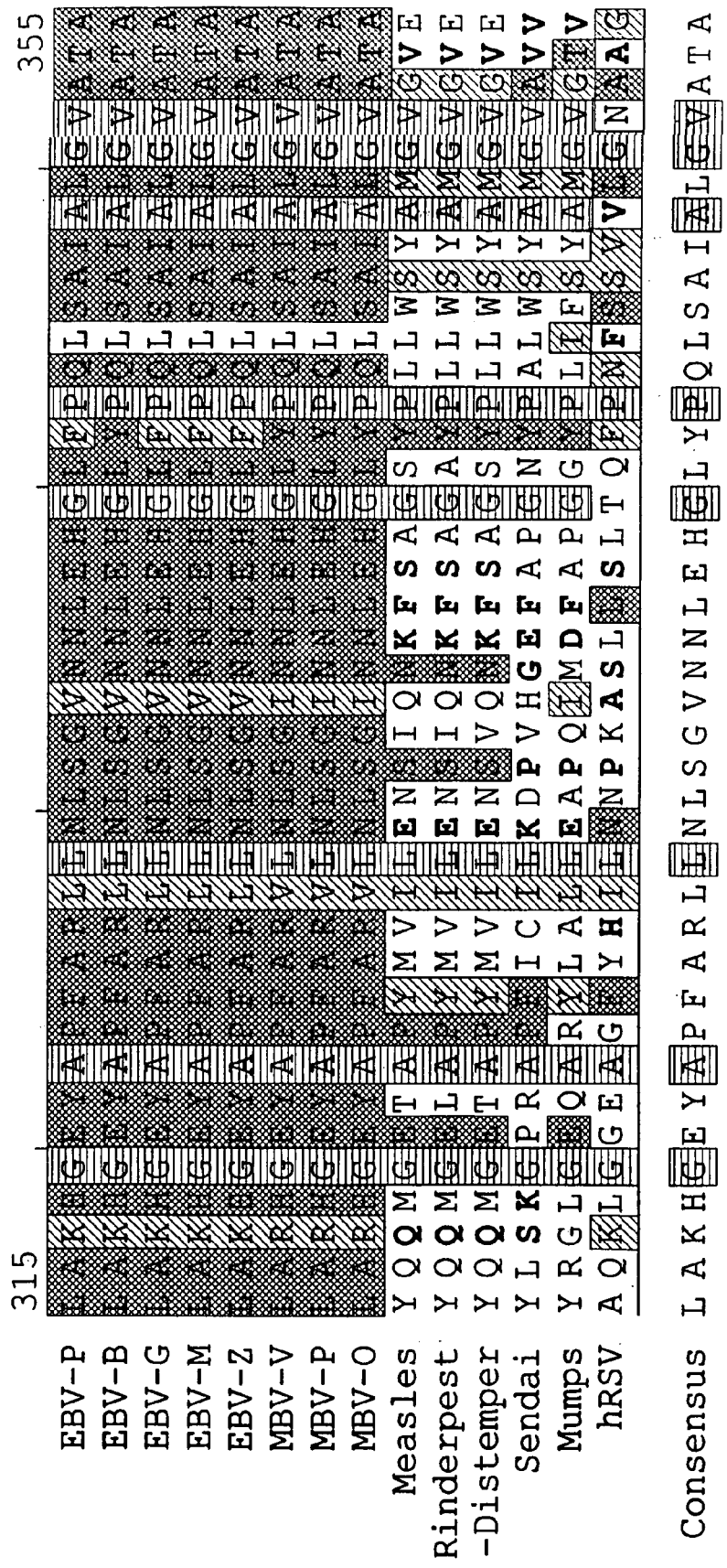

The mechanism described here provides insight into the assembly of filamentous viruses in general, including other filoviruses and a number of paramyxoviruses. Sequence comparison of the nucleoprotein between the various Ebola and Marburg NPs reveals a high degree of sequence conservation of these viral nucleoproteins. Interestingly, this sequence similarity is most striking within the filoviruses (FIG. 6A), but it is also seen in several paramyxoviruses, especially measles virus, the class most closely related to the filoviruses. An additional subsequence that is common to filoviruses, measles, rinderpest, and respiratory syncytial virus is also evident (FIG. 6B), suggesting that specific negative-stranded RNA viruses capable of forming filaments may use common mechanisms of assembly. The post-translational modification observed in Ebola virus represents a distinguishing feature that that may underlie the unique morphology of these viruses. Thus, the mechanism described in this disclosure provides insight into viral assembly, explains the unique properties of their structure, and provides a specific target for antiviral therapy (FIG. 5).

Figure 8:
FIG. 8 illustrates pseudoparticles for presentation of antigens or antigenic epitopes for immunogenic or vaccination purposes.
Figure 8:
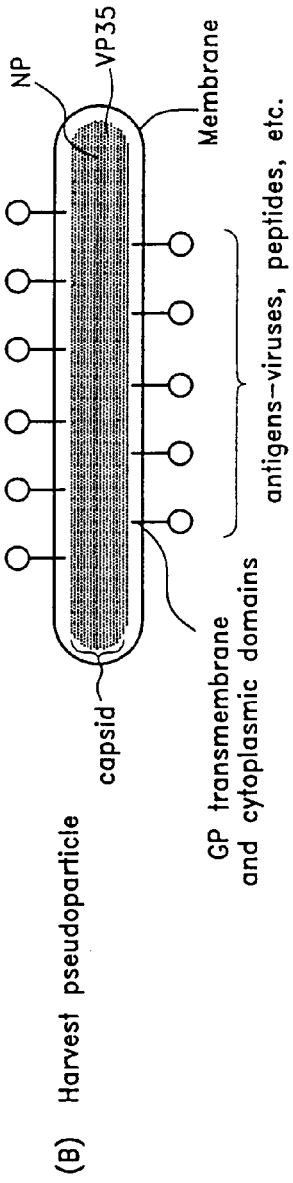

In another embodiment, the invention relates to pseudoparticles for presentation of antigens or antigenic epitopes for immunogenic or vaccination purposes. Referring to FIG. 8, pseudoparticles are generated by using an in vivo or in vitro approach. Referring to FIG. 8A, DNA plasmids (or adenoviral vectors or other gene-based vectors) encoding NP, VP35, VP24, and optionally VP40, as well as DNA plasmids (or adenoviral vectors or other gene-based vectors) encoding an antigen (possibly fused to Ebola GP transmembrane and cytoplasmic domains) are injected in vivo (into mice, or any other animal, including human) to generate pseudoparticles by an in vivo approach. Referring to FIG. 8B, these plasmids are alternatively transfected into producer cells, e.g., 293 cells, and the pseudoparticles are then harvested, to generate pseudoparticles by an in vitro approach, upon which the pseudoparticles are injected into recipients with or without adjuvant.

In conclusion, our data has demonstrated that it is achievable to assemble a large number of well-formed Ebola nucleocapsids in a human cell line with a minimum of three Ebola genes: NP, VP35 and VP24. Moreover, Ebola NP is O-glycosylated, which is required for protein-protein interactions. Though this critical step in the viral life cycle is catalyzed by normal cellular proteins, Ebola virus replication is acute and limited in duration. It is therefore envisioned as representing a target for antiviral therapies that may be common to different filoviruses. Alternatively, we envision targeting the VP35- or VP24-dependent steps of this process. These observations are therefore envisioned as helping to understand the pathogenesis of Ebola virus infection and disease as they facilitate the achievement of alternative antiviral targets and vaccines.

Plasmids

Plasmids containing GP, NP, VP40, VP35, VP30, and VP24 cDNA, provided by A. Sanchez (Sanchez, A. et al. 1993 *Virus Res* 29:215-240) were subcloned into the mammalian expression vector pVR1012 (Tooze, J. et al. 1988 *J Cell Biol* 106: 1475-1487); pVR1012-NPΔ5', ΔM, and Δ3' were created by mutagenesis PCR (Stratagene) using primers: CTGGATCCAGATCGATCCGAGTATGGATCATATC-CTACAAAAGACA (SEQ ID NO: 1) and its antisense for Δ5', primers CAAAACAGTACTTGATGATCTAGACGAG-GACGACGAGGACACT (SEQ ID NO: 2) and its antisense for ΔM, and primers CTTGGTCCTATTCGATCTAAAT-TCATGGCAATCCTGCAACATCATCAG (SEQ ID NO: 3) and its antisense for Δ3'.

pcDNA-NP-his was created by removal of the stop codon of NP by PCR using primers CGGATCCAGATCGATC-CGAGTATG (SEQ ID NO: 4) and GAAGGGCCCCTGAT-GATGTTGCAGGATTGCCA (SEQ ID NO: 5), and subcloned into the BamHI and ApaI sites of pcDNA-his-A (Invitrogen). All mutations have been confirmed by sequencing. pVR1012-VP35 and -V24 were digested with XbaI/BglII and subcloned into the XbaI/BamHI sites of pAdapt CMV to create pAd-VP35 and pAD-V24 for recombinant adenovirus production.

Transient Transfection and Electron Microscopy (EM)

293T cells were maintained in Dulbecco's Modified Eagle Medium (DMEM; Gibco-BRL), supplemented with 10% fetal bovine serum (FBS). Plasmid DNAs were purified using double cesium chloride sedimentation gradients. Approximately 3×10⁶ 293T cells were placed in a 10 cm dish one day before transfection. Two μg of each plasmid (each containing one of the Ebola genes) were mixed and used to transfect 293T cells, using the calcium phosphate method (Chen, C. and Okayama, H. 1987 *Mol Cell Biol* 7:2745-2752). The vector backbone was used as filler DNA to maintain the same amount of DNA in each transfection. Sixty three hours after transfection, the cells were lifted from plates by resuspending with DMEM, and then pelleted in a 15 ml conical tube by centrifugation at 1000 rpm. The supernatant was removed and a 10-fold volume of fixing solution was added (3% glutaraldehyde and 3% formaldehyde, cacodylate buffer, pH 7.3; Tousimis Research Corporation, Rockville, Md.). The specimens were mixed gently, and analyzed in the EM laboratory at the University of Michigan.

Immunoprecipitation and Western Blot Analysis

Recombinant adenoviruses containing VP35 and VP24 were produced for antibody production (Aoki, K. et al. 1999 *Mol Med* 5: 224-231). Polyclonal anti-NP, VP35 and VP24 were produced by the regimen described in (Sullivan, N. J. et al. 2000 *Nature* 408:605-609). The RNAs of NP, VP35 and VP24 were in vitro synthesized from plasmids of pcDNA-NP-his, pGEMgem-VP35, and pCR-VP24 by RiboMax RNA production system (Promega), and the $^{35}$S-labeled proteins were in vitro translated individually from these RNAs by Flexi Rabbit reticulocytes lysate or *E. coli* S30 extract systems from Promega, according to the user's manuals. Ten μl of each of $^{35}$S-methionine-labeled proteins were mixed and incubated at room temperature for 1 hour, then immunoprecipitated with 10 μl of antibody in 500 μl of immunoprecipitation buffer containing 50 mM Tris-HCl pH 7.4, 150 mM NaCl, 1% NP40, 1 mM DTT plus proteinase inhibitor cocktail for 1 hour at 4° C. Five μl of three-times washed Protein G agarose (Invitrogen) was added and incubated for another 1 hour. After washing five times with the buffer described above, the pellets were boiled in SDS gel loading buffer and resolved by SDS-PAGE with autoradiography. Western blot was performed as described (Friborg, J. et al. 1999 *Nature* 402:889-894).

Viral Capsid Production and Buoyant Density Gradient Analysis

3×10⁶ 293T cells were transfected with 3 μg of each of pVR1012-NP, VP35 and VP24 in a 100 mm tissue culture dish with DMEM medium. The cells were harvested after three days and freeze-thawed three times in PBS with 0.05% Tween 20. The cleared lysates were mixed with 60% of an Optipre™ (IODIXANOL) medium (Invitrogen) and final concentration of Optipre was adjusted to 30%. Density gradient was formed by centrifugation at 45K for 6 hours with a VTI50 rotor (according to the manufacturer's instructions; Invitrogen). The collected fractions were weighted at 1 ml of each fraction and plotted with density by fractions. Twenty μl of each fraction were separated on a 4-15% SDS-PAGE gel, transferred onto an Immobilon™-P membrane and blotted with mouse polyclonal anti-VP24, VP35 or NP. Each lane of Western blot represents and fits with one fraction of self-gradient OptiPre containing the cell lysates.

Biochemical Interactions Among Ebola Gene Products

In vitro translated and $^{35}$S-labeled NP, VP35 and VP24 were pulled down with anti-NP. The RNAs of NP, VP35 and VP24 were in vitro synthesized from plasmids of pcDNA-NP-his, pGEM-VP35, and pCR-VP24 by RiboMax RNA production system (Promega), and the $^{35}$S-labeled proteins were in vitro translated individually from these RNAs by Flexi Rabbit reticulocytes lysate. Ten μl of each of $^{35}$S-methionine-labeled proteins were mixed and incubated at room temperature for 1 hour to allow the interactions to occur, then immunoprecipitated with 10 μl of mouse polyclonal anti-NP in 500 μl of immunoprecipitation buffer containing 50 mM Tris-HCl pH 7.4, 150 mM NaCl, 1% NP40, 1 mM DTT plus proteinase inhibitor cocktail for 1 hour at 4° C. Five µl of three-times washed Protein G agarose (Invitrogen) were added and incubated for another 1 hour. After washing five times with the buffer described above, the pellets were boiled in 30 µl of Laemmli's sample buffer and resolved by SDS-PAGE with autoradiography.

Analysis of NP Sensitivity to Glycosylation

His-tagged NP was purified from pcDNA-NP-his-transfected 293T cells by the Xpress system (Invitrogen) and digested with a deglycosylation kit (CalBiochem) under denaturing and non-denaturing conditions. Five µg of purified NP was denatured at 100° C. for 5 minutes in 37.5 µl of buffer containing 35.7 mM sodium phosphate, 0.15% SDS and 70 mM β-mercaptoethanol, pH 7.0. It was then cooled to room temperature, 2.5 µl of TRITON X-100 solution was added, gently mixed, 1 µl each of N-Glycosidase F, α2-3,6,8,9-Neuramimidase, Endo-α-N-acetylgalactosamimidase, β1,4-galactosidase, and β-N-acetylglucosamimidase was added, and incubated for 3 hours at 37° C. Ten µl of the digested reactions were mixed with the same volume of Laemmli's sample buffer, separated with a 4-15% SDS-PAGE gel, and analyzed by Western blot with a mouse polyclonal anti-NP.

$0.5 \times 10^6$ 293T cells were transfected with 2 µg of pVR1012-NP in six-well plates. Six hours after transfection, glycosylation inhibitor deoxymannojirimycin (dMM) was added to final concentration of 2.5 mM and tunicamycin to 16 µg/ml. After 48 hours incubation, the cells were extracted with 300 µl of RIPA (radioimmunoprecipitation) buffer. Ten µl of the cleared cell lysates were denatured at 100° C. for 5 minutes in 37.5 µl of buffer containing 35.7 mM sodium phosphate, 0.15% SDS and 70 mM β-mercaptoethanol, pH 7.0. They were cooled to room temperature, 2.5 ml TRITON X-100 solution was added, and mixed gently. Then, 1 µl each of α2-3,6,8,9-neuramimidase, 0.5% SDS, 1% β-mercaptoethanol, and 50 mM sodium citrate, pH 5.5, for Endoglycosidase H was added. The controls were treated without adding the enzymes. After incubation for 1 hour at 37° C., 10 µl of the reactions were separated with a 4-15% SDS-PAGE gel and analyzed by Western blot with a polyclonal anti-NP.

Radiolabeling of Carbohydrates and Lectin Precipitation/Western Blotting $0.5 \times 10^6$ 293T cells were transfected with 2 µg of pcDNA-NP-his in six well plates. Sixteen hours later, the cells were labeled with 100 µCi each of $^3$H-thymidine, $^3$H-glycosamine, or $^3$H-galactose overnight in 3 ml of DMEM with 10% FCS and 100 µg/ml of D-glucose. The cells were extracted with RIPA buffer and equal amounts of cell lysates were used to pull out labeled NP with 50 µl of ProBond™ resin. After washing three times with 20 mM sodium phosphate, 500 mM sodium chloride and 100 mM Imidazole at pH 6.0, and then washing twice with the concentration of Imidazole at 200 mM, NP-his was eluted by heating at 100° C. for 5 minutes in 80 µl Laemmli's sample buffer. $^3$H incorporation was measured in a Liquid Scintillation Analyzer TRI-CARB-3100TR (Packard) using 5 µl of each sample mixed with 5 ml of MICROSCINT™ 20. SDS-PAGE was performed with 20 µl of Laemmli's sample buffer containing NP-his separated on a 4-15% gel. After incubation with 100 ml of fixation buffer (50% methanol, 10% acetic acid) for 30 minutes, soaking with Amplifer™ (Amersham) for 30 minutes, and drying for 120 minutes, the gel was exposed to Hyperfilm™ MP film (Amersham) at minus 75° C. for one week. Protein expression was detected with a Silver StainPlus kit (BioRad) on 20 µl of the same eluted sample was separated with 5-15% SDS-PAGE.

Figure 4A:
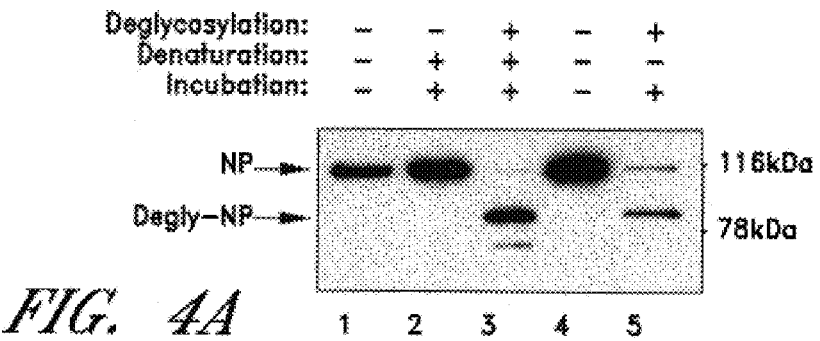
FIG. 4 shows post-translational modification of Ebola NP and biochemical characterization of NP glycosylation. A. Sensitivity of NP to deglycosylation. B. Relative resistance of NP in cell extracts from transfected 293 cells to digestion with Endo H in cells treated with no inhibitor (lane 9), 2.5 mM dMM (lane 10) or 16 μg/ml tunicamycin (lane 11) for 40 hours, in contrast to its sensitivity to neuramimidase (lane 6 vs. 7). C. Resistance of NP synthesis in transfected 293 cells in vivo to tunicamycin (left), in contrast to HIV gp160 (right). D. Labeling of NP with $^3$H-glycosamine and $^3$H-galactose. The methods used are identified as described below. E. Lectin precipitation and NP Western blot analysis. The identity and specificity of each lectin is indicated and described in the text below. Control, no lectin added, other conditions were same.
Figure 4B:
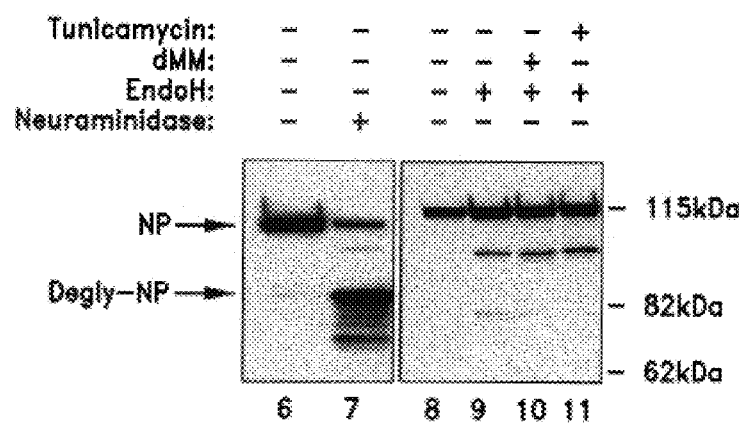
Figure 4C:
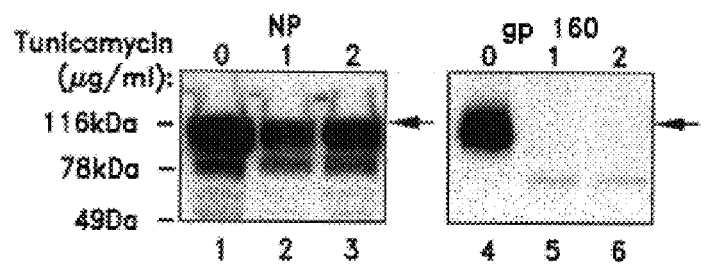
Figure 4D:
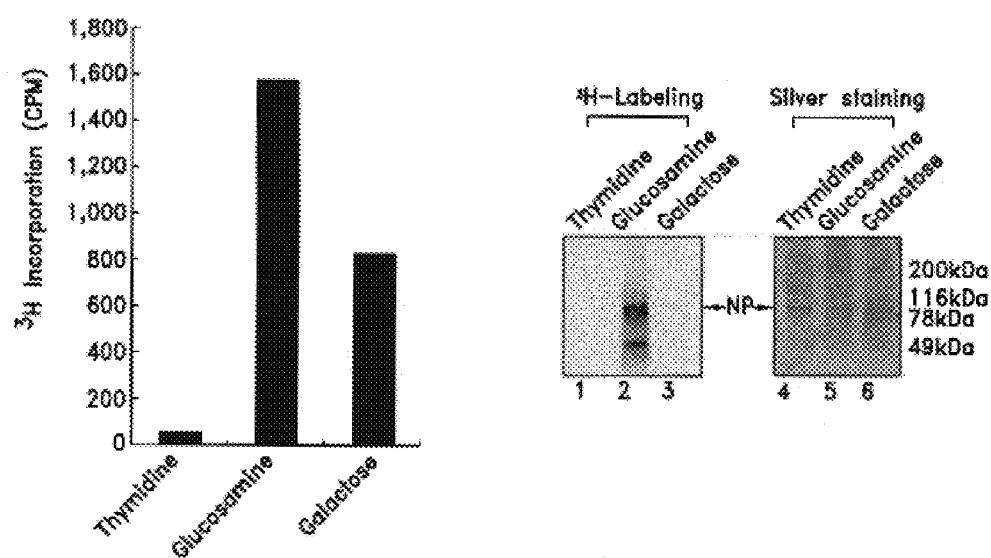
Figure 4E:
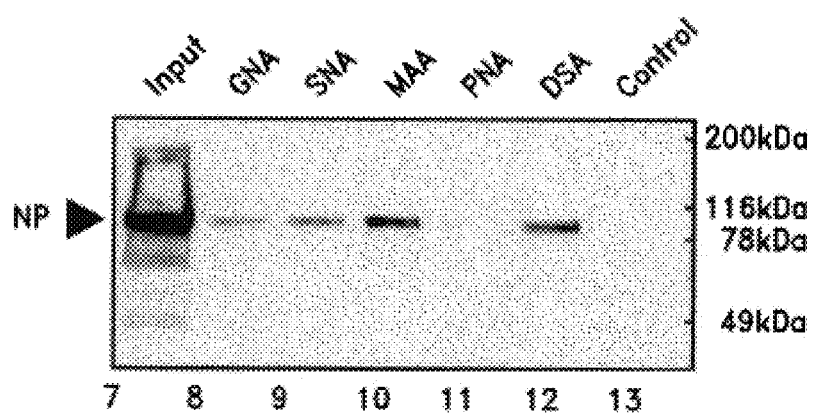

$3 \times 10^6$ 293T cells were transfected with 10 µg of pVR1012-NP in 100 mm dishes (FIG. 4B). Three days later, the cells were lifted from plates by resuspending with PBS, then pelleted in an Eppendorf tube by centrifugation at 3000 rpm. The cells were extracted in 1 ml of RIPA buffer. Fifty µl of cell lysates were mixed with H$_2$O and 2× binding buffer and adjusted to final 1× binding buffer (50 mM Tris-HCl, 150 mM NaCl, 1 mM MgCl$_2$, 1 mM MnCl$_2$, and 1 mM CaCl$_2$). Digoxigenin-labeled lectins (Roche Molecular Biochemicals) used for each reaction: GNA 25 µg, SNA 25 µg, DSA 25 µg, MAA 125 µg, PNA 250 µg. After 1 hour incubated at room temperature with agitation, Anti-Digoxigenin magnetic particles (Roche Molecular Biochemicals) were washed three times with 1× binding buffer and 30 µl was added to each reaction. After another one hour incubation, the particles were washed four times with 1× binding buffer, and recovered in 60 µl of Laemmli's sample buffer by heating at 100° C. for 5 minutes. Twenty five µl were separated with a 4-15% SDS-PAGE gel, and analyzed by Western blot with a mouse polyclonal anti-NP.

Synthetic Glycoside Analogues

Several potential inhibitors of the NP/VP35 interaction were tested for their ability to inhibit the synthesis of NP or the association of NP with VP35 and VP24. The inhibitor compounds under investigation are a variety of synthetic mono- and disaccharides. Manα1-O-octyl (Manα1-OC$_8$), acetylated Manα1-O-octyl (AcManα1-OC$_8$) and acetylated Manα1-3Manα-O-methyl (AcMan1-3Manα1-OMe) were prepared according to published procedures (Oscarson, S. and Tiden, A. K. 1993 Carbohydr Res 247:323-328; Brown, J. R. et al. 1997 Glycobiology 7:549-558). Acetylated Manα1-6Manα-O-dec-9-enyl (AcMan1-6Manα1-OC$_{10}$) was synthesized as described by Nikolaev and co-workers for the corresponding dec-9-enyl synthetic oligomer (Nikolaev, A. V. et al. 1995 J Chem Soc Perkin Trans 1:1977-1987.). Acetylated Galβ1-4GlcNAcβ-O-naphthalemethanol (Ac-Galβ1-4GlcNAcβ1-NM) was prepared according to published procedures (Sarkar, A. K. et al. 2000 Carbohydr Res 329:287-300). Per-O-acetylation is achieved with acetic anhydride and pyridine. All reaction products were analyzed by analytical thin-layer chromatography and Silica Gel 60$_{254}$ (E. Merck) plates and detection by charring by UV light or by charring with 5% (v/v) sulfuric acid in ethanol. Column chromatography was performed on Silica Gel 60$_{254}$ (Aldrich). All synthetic compounds that were subjected to biological testing gave electrospray mass spectra consistent with their proposed structures (Brown, J. R. et al. 2001 Bioorg Med Chem 9:815-824; Brown, J. R. et al. 1997 Glycobiology 7:549-558; Sarkar, A. K. et al. 2000 Carbohydr Res 329:287-300). These synthetic glycosides were added to the radiolabeled in vitro transcription/translation reaction prior to translation at 0.5, 1.0, or 2.0 mM concentrations and analyzed by SDS-PAGE or by co-immunoprecipitation with an antiserum to VP35 as described above.

Additional compounds tested in this system without any effect included benzyl 2-acetamido-2-deoxy-a-D-galactopyranoside, benzyl 2-acetamido-2-deoxy-3-O-b-D-galactopyranosyl-a-D-galactopyranoside, phenyl N-acetyl-a-D-galactosaminide, benzyl Z-a-D-glucosaminide, benzyl Z-b-D-glucosaminide, benzyl 2-acetamido-2-deoxy-b-D-glucopyranoside (Sigma, St. Louis, Mo.); and Brefeldin A (Calbiochem, San Diego, Calif.).

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A pseudoparticle comprising:
    a) a 45-50 nm filovirus nucleocapsid consisting of NP, VP35 and VP24 proteins, and optionally, VP40 protein; and
    b) an antigen or antigenic epitope from a filovirus protein that is exposed on the surface of the pseudoparticle.

2. The pseudoparticle of claim 1 wherein said antigen or antigenic epitope is suited to induce an immune response against infectious disease.

3. A pharmaceutical composition comprising the pseudoparticle of claim 1 and an acceptable pharmaceutical carrier.

4. An immunogenic composition comprising the pseudoparticle of claim 1 and an adjuvant.

5. The pseudoparticle of claim 1 wherein said nucleocapsid includes said VP40 protein and wherein said antigen or antigenic epitope is from a filovirus protein.

6. The pseudoparticle of claim 1 wherein said nucleocapsid excludes said VP40 protein and wherein said antigen or antigenic epitope is from a filovirus protein.

7. The pseudoparticle of claim 2 wherein said nucleocapsid includes said VP40 protein, wherein said antigen or antigenic epitope is from a filovirus protein, and wherein said antigen or antigenic epitope is selected from proteins suited to induce an immune response against infectious diseases.

8. The pseudoparticle of claim 2 wherein said nucleocapsid excludes said VP40 protein, wherein said antigen or antigenic epitope is from a filovirus protein, and wherein said antigen or antigenic epitope is selected from proteins suited to induce an immune response against infectious diseases.

9. A pharmaceutical composition comprising the pseudoparticle of claim 2 and an acceptable pharmaceutical carrier.

10. An immunogenic composition comprising the pseudoparticle of claim 2 and an adjuvant.

* * * * *

SEQUENCE LISTING

<160> NUMBER OF SEQ ID NOS: 29

<210> SEQ ID NO 1
<211> LENGTH: 46
<212> TYPE: DNA
<213> ORGANISM: Artificial Sequence
<220> FEATURE:
<223> OTHER INFORMATION: synthetic primer

<400> SEQUENCE: 1
ctggatccag atcgatccga gtatggatca tatcctacaa aagaca        46

<210> SEQ ID NO 2
<211> LENGTH: 43
<212> TYPE: DNA
<213> ORGANISM: Artificial Sequence
<220> FEATURE:
<223> OTHER INFORMATION: synthetic primer

<400> SEQUENCE: 2
caaaacagta cttgatgatc tagacgagga cgacgaggac act        43

<210> SEQ ID NO 3
<211> LENGTH: 48
<212> TYPE: DNA
<213> ORGANISM: Artificial Sequence
<220> FEATURE:
<223> OTHER INFORMATION: synthetic primer

<400> SEQUENCE: 3
cttggtccta ttcgatctaa attcatggca atcctgcaac atcatcag        48

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
cggatccaga tcgatccgag tatg        24

<210> SEQ ID NO 5
<211> LENGTH: 32
<212> TYPE: DNA
<213> ORGANISM: Artificial Sequence
<220> FEATURE:
<223> OTHER INFORMATION: synthetic primer

<400> SEQUENCE: 5
gaagggcccc tgatgatgtt gcaggattgc ca        32

<210> SEQ ID NO 6
<211> LENGTH: 384
<212> TYPE: PRT
<213> ORGANISM: Ebola virus P

<400> SEQUENCE: 6

```
Met Asp Ser Arg Pro Gln Lys Ile Trp Met Ala Pro Ser Leu Thr Glu
 1               5                  10                  15

Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
```

-continued

```
                35                  40                  45

Leu Glu Glu Ile Cys Gln Leu Ile Ile Gln Ala Phe Glu Ala Gly Val
 50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                 85                  90                  95

Lys Tyr Leu Glu Gly His Gly Phe Arg Phe Glu Val Lys Lys Arg Asp
                100                 105                 110

Gly Val Lys Arg Leu Glu Glu Leu Pro Ala Val Ser Ser Gly Lys
            115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
            195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
            275                 280                 285

Lys His Gly Glu Tyr Ala Pro Phe Ala Arg Leu Leu Asn Leu Ser Gly
290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
            355                 360                 365

Asp Asp Gln Glu Lys Lys Ile Leu Met Asn Phe His Gln Lys Lys Asn
370                 375                 380

<210> SEQ ID NO 7
<211> LENGTH: 384
<212> TYPE: PRT
<213> ORGANISM: Ebola virus B

<400> SEQUENCE: 7

Met Asp Arg Gly Thr Arg Arg Ile Trp Val Ser Gln Asn Gln Gly Asp
 1               5                  10                  15

Thr Asp Leu Asp Tyr His Lys Ile Leu Thr Ala Gly Leu Thr Val Gln
                20                  25                  30
```

```
Gln Gly Ile Val Arg Gln Lys Ile Ile Ser Val Tyr Leu Val Asp Asn
        35                  40                  45

Leu Glu Ala Met Cys Gln Leu Val Ile Gln Ala Phe Glu Ala Gly Ile
 50                  55                  60

Asp Phe Gln Glu Asn Ala Asp Ser Phe Leu Leu Met Leu Cys Leu His
 65                  70                  75                  80

His Ala Tyr Gln Gly Asp Tyr Lys Leu Phe Leu Glu Ser Asn Ala Val
                 85                  90                  95

Gln Tyr Leu Glu Gly His Gly Phe Lys Phe Glu Leu Arg Lys Lys Asp
            100                 105                 110

Gly Val Asn Arg Leu Glu Glu Leu Pro Ala Ala Thr Ser Gly Lys
            115                 120                 125

Asn Ile Arg Arg Thr Leu Ala Ala Leu Pro Glu Glu Thr Thr Glu
            130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
            195                 200                 205

Leu Ile Lys Tyr Leu Leu Ile His Gln Gly Met His Met Val Ala Gly
            210                 215                 220

His Asp Ala Asn Asp Ala Val Ile Ala Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Gln Gly Val Arg Leu His Pro Leu Ala Arg Thr Ala Lys
            260                 265                 270

Val Arg Asn Glu Val Asn Ala Phe Lys Ala Ala Leu Ser Ser Leu Ala
            275                 280                 285

Lys His Gly Glu Tyr Ala Pro Phe Ala Arg Leu Leu Asn Leu Ser Gly
            290                 295                 300

Val Asn Asn Leu Glu His Gly Leu Tyr Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp Ser Leu Gly Leu
            355                 360                 365

Asp Asp Gln Glu Arg Arg Ile Leu Met Asn Phe His Gln Lys Lys Asn
370                 375                 380

<210> SEQ ID NO 8
<211> LENGTH: 384
<212> TYPE: PRT
<213> ORGANISM: Ebola virs G

<400> SEQUENCE: 8

Met Asp Ser Arg Pro Gln Lys Val Trp Met Thr Pro Ser Leu Thr Glu
 1               5                  10                  15

Ser Asp Met Asp Tyr His Lys Ile Leu Thr Ala Gly Leu Ser Val Gln
                 20                  25                  30
```

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
 50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
            115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Arg Lys Val Gln Arg Gln Ile
            165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
            195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
            245                 250                 255

Lys Thr Gln Arg Gly Val Arg Leu His Pro Leu Ala Arg Thr Ala Lys
            260                 265                 270

Val Lys Asn Glu Val Asn Ser Leu Lys Ala Ala Leu Ser Ser Leu Ala
            275                 280                 285

Lys His Gly Glu Tyr Ala Pro Phe Ala Arg Leu Leu Asn Leu Ser Gly
            290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
            325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
            355                 360                 365

Asp Asp Gln Glu Lys Lys Ile Leu Met Asn Phe His Gln Lys Lys Asn
            370                 375                 380

<210> SEQ ID NO 9
<211> LENGTH: 384
<212> TYPE: PRT
<213> ORGANISM: Ebola virus M

<400> SEQUENCE: 9

Met Asp Ser Arg Pro Gln Lys Ile Trp Met Ala Pro Ser Leu Thr Glu
 1                   5                  10                  15

Ser Asp Met Asp Tyr His Lys Ile Leu Thr Ala Gly Leu Ser Val Gln

-continued

```
                 20                  25                  30
Gln Gly Ile Val Arg Gln Arg Val Ile Pro Val Tyr Gln Val Asn Asn
             35                  40                  45

Leu Glu Glu Ile Cys Gln Leu Ile Ile Gln Ala Phe Glu Ala Gly Val
 50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                 85                  90                  95

Lys Tyr Leu Glu Gly His Gly Phe Arg Phe Glu Val Lys Lys Arg Asp
             100                 105                 110

Gly Val Lys Arg Leu Glu Glu Leu Pro Ala Val Ser Ser Gly Lys
             115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Arg Lys Val Gln Arg Gln Ile
                 165                 170                 175

Gln Val His Ala Glu Gln Gly Leu Ile Gln Tyr Pro Thr Ala Trp Gln
             180                 185                 190

Ser Val Gly His Met Met Val Ile Phe Arg Leu Met Arg Thr Asn Phe
             195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                 245                 250                 255

Lys Thr Glu Arg Gly Val Arg Leu His Pro Leu Ala Arg Thr Ala Lys
             260                 265                 270

Val Lys Asn Glu Val Asn Ser Leu Lys Ala Ala Leu Ser Ser Leu Ala
             275                 280                 285

Lys His Gly Glu Tyr Ala Pro Phe Ala Arg Leu Leu Asn Leu Ser Gly
             290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                 325                 330                 335

Gly Glu Gln Tyr Gln Gln Leu Arg Glu Ala Ala Thr Glu Ala Glu Lys
             340                 345                 350

Gln Leu Gln Gln Tyr Ala Glu Ser Arg Glu Leu Asp His Leu Gly Leu
             355                 360                 365

Asp Asp Gln Glu Lys Lys Ile Leu Met Asn Phe His Gln Lys Lys Asn
370                 375                 380

<210> SEQ ID NO 10
<211> LENGTH: 384
<212> TYPE: PRT
<213> ORGANISM: Ebola virus Z

<400> SEQUENCE: 10

Met Asp Ser Arg Pro Gln Lys Val Trp Met Thr Pro Ser Leu Thr Glu
 1               5                  10                  15
```

```
Ser Asp Met Asp Tyr His Lys Ile Leu Thr Ala Gly Leu Ser Val Gln
            20                  25                  30

Gln Gly Ile Val Arg Gln Arg Val Ile Pro Val Tyr Gln Val Asn Asn
        35                  40                  45

Leu Glu Glu Ile Cys Gln Leu Ile Ile Gln Ala Phe Glu Ala Gly Val
    50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Leu Leu Pro Ala Val Ser Ser Gly Lys
            115                 120                 125

Asn Ile Lys Arg Thr Leu Ala Ala Met Pro Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
    210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Glu Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
        355                 360                 365

Asp Asp Gln Glu Lys Lys Ile Leu Met Asn Phe His Gln Lys Lys Asn
370                 375                 380

<210> SEQ ID NO 11
<211> LENGTH: 366
<212> TYPE: PRT
<213> ORGANISM: MBV-V

<400> SEQUENCE: 11

Met Asp Leu His Ser Leu Leu Glu Leu Gly Thr Lys Pro Thr Ala Pro
1               5                   10                  15
```

His Val Arg Asn Lys Lys Val Ile Leu Phe Asp Thr Asn His Gln Val
            20                  25                  30

Ser Ile Cys Asn Gln Ile Ile Asp Ala Ile Asn Ser Gly Ile Asp Leu
        35                  40                  45

Gly Asp Leu Leu Glu Gly Gly Leu Leu Thr Leu Cys Val Glu His Tyr
50                  55                  60

Tyr Asn Ser Asp Lys Asp Lys Phe Asn Thr Ser Pro Val Ala Lys Tyr
65                  70                  75                  80

Leu Arg Asp Ala Gly Tyr Glu Phe Asp Val Ile Lys Asn Ala Asp Ala
                85                  90                  95

Thr Arg Phe Leu Asp Val Ser Pro Asn Glu Pro His Tyr Ser Pro Leu
            100                 105                 110

Ile Leu Ala Leu Lys Thr Leu Glu Ser Thr Glu Ser Gln Arg Gly Arg
        115                 120                 125

Ile Gly Leu Phe Leu Ser Phe Cys Ser Leu Phe Leu Pro Lys Leu Val
    130                 135                 140

Val Gly Asp Arg Ala Ser Ile Glu Lys Ala Leu Arg Gln Val Thr Val
145                 150                 155                 160

His Gln Glu Gln Gly Ile Val Thr Tyr Pro Asn His Trp Leu Thr Thr
                165                 170                 175

Gly His Met Lys Val Ile Phe Gly Ile Leu Arg Ser Ser Phe Ile Leu
            180                 185                 190

Lys Phe Val Leu Ile His Gln Gly Val Asn Leu Val Thr Gly His Asp
        195                 200                 205

Ala Tyr Asp Ser Ile Ile Ser Asn Ser Val Gly Gln Thr Arg Phe Ser
    210                 215                 220

Gly Leu Leu Ile Val Lys Thr Val Leu Glu Phe Ile Leu Gln Lys Thr
225                 230                 235                 240

Asp Ser Gly Val Thr Leu His Pro Leu Val Arg Thr Ser Lys Val Lys
                245                 250                 255

Asn Glu Val Ala Ser Phe Lys Gln Ala Leu Ser Asn Leu Ala Arg His
            260                 265                 270

Gly Glu Tyr Ala Pro Phe Ala Arg Val Leu Asn Leu Ser Gly Ile Asn
        275                 280                 285

Asn Leu Glu His Gly Leu Tyr Pro Gln Leu Ser Ala Ile Ala Leu Gly
    290                 295                 300

Val Ala Thr Ala His Gly Ser Thr Leu Ala Gly Val Asn Val Gly Glu
305                 310                 315                 320

Gln Tyr Gln Gln Leu Arg Glu Ala Ala His Asp Ala Glu Val Lys Leu
                325                 330                 335

Gln Arg Arg His Glu His Gln Glu Ile Gln Ala Ile Ala Glu Asp Asp
            340                 345                 350

Glu Glu Arg Lys Ile Leu Glu Gln Phe His Leu Gln Lys Thr
        355                 360                 365

<210> SEQ ID NO 12
<211> LENGTH: 366
<212> TYPE: PRT
<213> ORGANISM: MBV-P

<400> SEQUENCE: 12

Met Asp Leu His Ser Leu Leu Glu Leu Gly Thr Lys Pro Thr Ala Pro
1               5                   10                  15

His Val Arg Asn Lys Lys Val Ile Leu Phe Asp Thr Asn His Gln Val

```
                 20                  25                  30
Ser Ile Cys Asn Gln Ile Ile Asp Ala Ile Asn Ser Gly Ile Asp Leu
             35                  40                  45

Gly Asp Leu Leu Glu Gly Gly Leu Leu Thr Leu Cys Val Glu His Tyr
 50                  55                  60

Tyr Asn Ser Asp Lys Asp Lys Phe Asn Thr Ser Pro Val Ala Lys Tyr
65                  70                  75                  80

Leu Arg Asp Ala Gly Tyr Glu Phe Asp Val Ile Lys Asn Ala Asp Ala
                 85                  90                  95

Thr Arg Phe Leu Asp Val Ser Pro Asn Glu Pro His Tyr Ser Pro Leu
            100                 105                 110

Ile Leu Ala Leu Lys Thr Leu Glu Ser Thr Glu Ser Gln Arg Gly Arg
            115                 120                 125

Ile Gly Leu Phe Leu Ser Phe Cys Ser Leu Phe Leu Pro Lys Leu Val
            130                 135                 140

Val Gly Asp Arg Ala Ser Ile Glu Lys Ala Leu Arg Gln Val Thr Val
145                 150                 155                 160

His Gln Glu Gln Gly Ile Val Thr Tyr Pro Asn His Trp Leu Thr Thr
                165                 170                 175

Gly His Met Lys Val Ile Phe Gly Ile Leu Arg Ser Ser Phe Ile Leu
            180                 185                 190

Lys Phe Val Leu Ile His Gln Gly Val Asn Leu Val Thr Gly His Asp
            195                 200                 205

Ala Tyr Asp Ser Ile Ile Ser Asn Ser Val Gly Gln Thr Arg Phe Ser
            210                 215                 220

Gly Leu Leu Ile Val Lys Thr Val Leu Glu Phe Ile Leu Gln Lys Thr
225                 230                 235                 240

Asp Ser Gly Val Thr Leu His Pro Leu Val Arg Thr Ser Lys Val Lys
                245                 250                 255

Asn Glu Val Ala Ser Phe Lys Gln Ala Leu Ser Asn Leu Ala Arg His
            260                 265                 270

Gly Glu Tyr Ala Pro Phe Ala Arg Val Leu Asn Leu Ser Gly Ile Asn
            275                 280                 285

Asn Leu Glu His Gly Leu Tyr Pro Gln Leu Ser Ala Ile Ala Leu Gly
            290                 295                 300

Val Ala Thr Ala His Gly Ser Thr Leu Ala Gly Val Asn Val Gly Glu
305                 310                 315                 320

Gln Tyr Gln Gln Leu Arg Glu Ala Ala His Asp Ala Glu Val Lys Leu
                325                 330                 335

Gln Arg Arg His Glu His Gln Glu Ile Gln Ala Ile Ala Glu Asp Asp
            340                 345                 350

Glu Glu Arg Lys Ile Leu Glu Gln Phe His Leu Gln Lys Thr
            355                 360                 365

<210> SEQ ID NO 13
<211> LENGTH: 366
<212> TYPE: PRT
<213> ORGANISM: MBV-O

<400> SEQUENCE: 13

Met Asp Leu His Ser Leu Leu Glu Leu Gly Thr Lys Pro Thr Ala Pro
 1               5                  10                  15

His Val Arg Asn Lys Lys Val Ile Leu Phe Asp Thr Asn His Gln Val
                 20                  25                  30
```

```
Ser Ile Cys Asn Gln Ile Ile Asp Ala Ile Asn Ser Gly Ile Asp Leu
         35                  40                  45

Gly Asp Leu Leu Glu Gly Gly Leu Leu Thr Leu Cys Val Glu His Tyr
 50                  55                  60

Tyr Asn Ser Asp Lys Asp Lys Phe Asn Thr Ser Pro Ile Ala Lys Tyr
 65                  70                  75                  80

Leu Arg Asp Ala Gly Tyr Glu Phe Asp Val Val Lys Asn Ala Asp Ala
                 85                  90                  95

Thr Arg Phe Leu Asp Val Ile Pro Asn Glu Pro His Tyr Ser Pro Leu
                100                 105                 110

Ile Leu Ala Leu Lys Thr Leu Glu Ser Thr Glu Ser Gln Arg Gly Arg
                115                 120                 125

Ile Gly Leu Phe Leu Ser Phe Cys Ser Leu Phe Leu Pro Lys Leu Val
                130                 135                 140

Val Gly Asp Arg Ala Ser Ile Glu Lys Ala Leu Arg Gln Val Thr Val
145                 150                 155                 160

His Gln Glu Gln Gly Ile Val Thr Tyr Pro Asn His Trp Leu Thr Thr
                    165                 170                 175

Gly His Met Lys Val Ile Phe Gly Ile Leu Arg Ser Ser Phe Ile Leu
                180                 185                 190

Lys Phe Val Leu Ile His Gln Gly Val Asn Leu Val Thr Gly His Asp
                195                 200                 205

Ala Tyr Asp Ser Ile Ile Ser Asn Ser Val Gly Gln Thr Arg Phe Ser
                210                 215                 220

Gly Leu Leu Ile Val Lys Thr Val Leu Glu Phe Ile Leu Gln Lys Thr
225                 230                 235                 240

Asp Ser Gly Val Thr Leu His Pro Leu Val Arg Thr Ser Lys Val Lys
                    245                 250                 255

Asn Glu Val Ala Ser Phe Lys Gln Ala Leu Ser Asn Leu Ala Arg His
                260                 265                 270

Gly Glu Tyr Ala Pro Phe Ala Arg Val Leu Asn Leu Ser Gly Ile Asn
                275                 280                 285

Asn Leu Glu His Gly Leu Tyr Pro Gln Leu Ser Ala Ile Ala Leu Gly
                290                 295                 300

Val Ala Thr Ala His Gly Ser Thr Leu Ala Gly Val Asn Val Gly Glu
305                 310                 315                 320

Gln Tyr Gln Gln Leu Arg Glu Ala Ala His Asp Ala Glu Ile Lys Leu
                325                 330                 335

Gln Arg Arg His Glu His Gln Glu Ile Gln Ala Ile Ala Glu Asp Asp
                340                 345                 350

Glu Glu Arg Lys Ile Leu Glu Gln Phe His Leu Gln Lys Thr
                355                 360                 365

<210> SEQ ID NO 14
<211> LENGTH: 384
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(384)
<223> OTHER INFORMATION: Xaa = Any Amino Acid

<400> SEQUENCE: 14

Met Asp Ser Arg Pro Gln Lys Ile Trp Met Xaa Pro Ser Leu Thr Glu
  1               5                  10                  15
```

Ser Asp Met Asp Tyr His Lys Ile Leu Thr Ala Gly Leu Ser Val Gln
            20                  25                  30

Gln Gly Ile Val Arg Gln Lys Val Ile Pro Val Tyr Gln Val Asn Asn
        35                  40                  45

Leu Glu Glu Ile Cys Gln Leu Ile Ile Gln Ala Phe Glu Ala Gly Ile
 50                  55                  60

Asp Phe Gln Glu Ser Ala Asp Ser Phe Leu Leu Met Leu Cys Leu His
 65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Pro Ala Val Ser Ser Gly Lys
        115                 120                 125

Asn Ile Lys Arg Thr Leu Ala Ala Leu Pro Glu Glu Thr Thr Glu
    130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Gly Met His Met Val Ala Gly
210                 215                 220

His Asp Ala Asn Asp Ala Val Ile Ser Asn Ser Val Ala Gln Ala Arg
225                 230                 235                 240

Phe Ser Gly Leu Leu Ile Val Lys Thr Val Leu Asp His Ile Leu Gln
                245                 250                 255

Lys Thr Asp Arg Gly Val Arg Leu His Pro Leu Ala Arg Thr Ala Lys
            260                 265                 270

Val Lys Asn Glu Val Asn Ser Phe Lys Ala Ala Leu Ser Ser Leu Ala
        275                 280                 285

Lys His Gly Glu Tyr Ala Pro Phe Ala Arg Leu Leu Asn Leu Ser Gly
    290                 295                 300

Val Asn Asn Leu Glu His Gly Leu Phe Pro Gln Leu Ser Ala Ile Ala
305                 310                 315                 320

Leu Gly Val Ala Thr Ala His Gly Ser Thr Leu Ala Gly Val Asn Val
                325                 330                 335

Gly Glu Gln Tyr Gln Gln Leu Arg Glu Ala Ala Thr Glu Ala Glu Lys
            340                 345                 350

Gln Leu Gln Gln Tyr Ala Glu Ser Arg Glu Leu Asp His Leu Gly Leu
        355                 360                 365

Asp Asp Gln Glu Lys Lys Ile Leu Met Asn Phe His Gln Lys Lys Asn
    370                 375                 380

<210> SEQ ID NO 15
<211> LENGTH: 375
<212> TYPE: PRT
<213> ORGANISM: C-Distemper virus
<220> FEATURE:
<221> NAME/KEY: VARIANT
<222> LOCATION: (1)...(375)
<223> OTHER INFORMATION: Xaa = Any Amino Acid

```
<400> SEQUENCE: 15

Phe Lys Arg Thr Arg Asp Gln Pro Pro Leu Ala Ser Gly Ser Gly Gly
 1               5                  10                  15

Ala Ile Arg Gly Ile Lys His Val Ile Val Leu Ile Pro Gly Asp
             20                  25                  30

Ser Ser Ile Val Thr Arg Ser Arg Leu Leu Asp Arg Leu Val Arg Leu
             35                  40                  45

Val Gly Asp Pro Lys Ile Asn Gly Pro Lys Leu Thr Gly Ile Leu Ile
         50                  55                  60

Ser Ile Leu Ser Leu Phe Val Glu Ser Pro Gly Gln Leu Ile Gln Arg
 65                  70                  75                  80

Ile Ile Asp Xaa Pro Asp Val Ser Ile Lys Leu Val Glu Val Ile Pro
                 85                  90                  95

Ser Ile Asn Ser Val Cys Gly Leu Thr Phe Ala Ser Arg Gly Ala Ser
             100                 105                 110

Leu Asp Ser Glu Ala Asp Glu Phe Phe Lys Ile Val Asp Glu Gly Ser
         115                 120                 125

Lys Ala Gln Gly Gln Leu Gly Trp Leu Glu Asn Lys Glu Gln Phe Asn
130                 135                 140

Ile Leu Leu Ala Ser Ile Leu Ala Gln Ile Trp Ile Leu Leu Ala Lys
145                 150                 155                 160

Ala Val Thr Ala Pro Asp Thr Ala Ala Asp Ser Glu Met Arg Arg Trp
                165                 170                 175

Ile Lys Tyr Thr Gln Gln Gly Glu Phe Arg Met Asn Lys Ile Trp Leu
            180                 185                 190

Asp Ile Val Arg Asn Arg Ile Ala Glu Asp Leu Ser Leu Arg Arg Phe
        195                 200                 205

Met Val Ala Leu Ile Leu Asp Ile Lys Ser Pro Gly Asn Lys Pro Arg
    210                 215                 220

Ile Ala Glu Met Ile Cys Asp Ile Asp Asn Tyr Ile Val Glu Ala Gly
225                 230                 235                 240

Leu Ala Ser Phe Ile Leu Thr Ile Lys Phe Gly Ile Glu Thr Met Tyr
                245                 250                 255

Pro Ala Leu Gly Leu His Glu Phe Ser Gly Glu Leu Thr Thr Ile Glu
            260                 265                 270

Ser Leu Met Met Leu Tyr Gln Gln Met Gly Glu Thr Ala Pro Tyr Met
        275                 280                 285

Val Ile Leu Glu Asn Ser Val Gln Asn Lys Phe Ser Ala Gly Ser Tyr
    290                 295                 300

Pro Leu Leu Trp Ser Tyr Ala Met Gly Val Gly Val Glu Leu Glu Asn
305                 310                 315                 320

Ser Met Gly Gly Leu Asn Phe Glu Ser Ser Tyr Phe Asp Pro Ala Tyr
                325                 330                 335

Phe Arg Leu Gly Gln Glu Met Val Arg Arg Ser Ala Gly Lys Val Ser
            340                 345                 350

Ser Ala Ala Glu Leu Gly Ile Thr Lys Glu Glu Ala Gln Leu Val Ser
        355                 360                 365

Glu Ile Ala Ser Lys Thr Thr
    370                 375

<210> SEQ ID NO 16
<211> LENGTH: 376
<212> TYPE: PRT
```

<213> ORGANISM: Measles virus

<400> SEQUENCE: 16

```
Phe Lys Arg Asn Lys Asp Lys Pro P

```
<212> TYPE: PRT
<213> ORGANISM: Rinderpest

<400> SEQUENCE: 17
```

| | | | | | | | | | | | | | | |
|---|---|---|---|---|---|---|---|---|---|---|---|---|---|---|
|Phe|Lys|Lys|Asn|Lys|Asp|Lys|Pro|Pro|Leu|Ala|Ala|Gly|Ser|Gly|Gly
1| | | |5| | | | |10| | | | |15

Ala Ile Arg Gly Ile Lys His Val Ile Val Pro Ile Pro Gly Asp
        20                  25                  30

Ser Ser Ile Thr Thr Arg Ser Arg Leu Leu Asp Cys Leu Val Lys Met
65            35                  40                  45

Val Gly Asp Pro Asp Ile Ser Gly Pro Lys Leu Thr Gly Ala Leu Ile
50                      55                  60

Ser Ile Leu Ser Leu Phe Val Glu Ser Pro Gly Gln Leu Ile Gln Arg
65                  70                  75                  80

Ile Thr Asp Asp Pro Asp Ile Ser Ile Lys Leu Val Glu Val Ile Gln
                85                  90                  95

Ser Asp Lys Thr Gln Ser Gly Leu Thr Phe Ala Ser Arg Gly Ala Ser
                100                 105                 110

Met Asp Asp Glu Ala Gln Arg Tyr Phe Thr Tyr Asp Glu Pro Asn Gly
                115                 120                 125

Gly Glu Glu Arg Gln Ser Tyr Trp Phe Glu Asn Arg Glu Gly Phe Asn
130                 135                 140

Met Ile Leu Ala Thr Ile Leu Ala Gln Ile Trp Ile Leu Leu Ala Lys
145                 150                 155                 160

Ala Val Thr Thr Pro Asp Thr Ala Asp Ser Glu Leu Arg Arg Trp
                165                 170                 175

Val Lys Tyr Thr Gln Gln Gly Glu Phe Arg Leu Asp Lys Gly Trp Leu
                180                 185                 190

Asp Thr Val Arg Asn Arg Ile Ala Glu Asp Leu Ser Leu Arg Arg Phe
                195                 200                 205

Met Val Ala Leu Ile Leu Asp Ile Lys Arg Thr Pro Gly Asn Lys Pro
210                 215                 220

Arg Ile Ala Glu Met Ile Cys Asp Ile Asp Thr Tyr Ile Val Glu Ala
225                 230                 235                 240

Gly Leu Ala Ser Phe Ile Leu Thr Ile Lys Phe Gly Ile Glu Thr Met
                245                 250                 255

Tyr Pro Ala Leu Gly Leu His Glu Phe Ala Gly Glu Leu Ser Thr Ile
                260                 265                 270

Glu Ser Leu Met Asn Leu Tyr Gln Gln Met Gly Glu Leu Ala Pro Tyr
                275                 280                 285

Met Val Ile Leu Glu Asn Ser Ile Gln Asn Lys Phe Ser Ala Gly Ala
290                 295                 300

Tyr Pro Leu Leu Trp Ser Tyr Ala Met Gly Val Gly Val Glu Leu Glu
305                 310                 315                 320

Ser Ser Met Gly Gly Leu Asn Phe Gly Arg Ser Tyr Phe Asp Pro Ala
                325                 330                 335

Tyr Phe Arg Leu Gly Gln Glu Met Val Arg Arg Ser Ala Gly Lys Val
                340                 345                 350

Ser Ser Ala Ser Glu Leu Gly Ile Thr Glu Glu Ala Lys Leu Val
                355                 360                 365

Ser Glu Ile Ala Ala Tyr Thr Gly
                370                 375

```
<210> SEQ ID NO 18
```

<211> LENGTH: 376
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)...(376)
<223> OTHER INFORMATION: Xaa = Any Amino Acid

<400> SEQUENCE: 18

```
Met Asp Xaa Xaa Xaa Lys Ile Trp Met Xaa Xaa Xaa Xaa Xaa Glu
 1               5                  10                  15

Ser Asp Met Asp Tyr His Lys Ile Leu Thr Ala Gly Leu Ser Val Gln
            20                  25                  30

Gln Gly Ile Val Arg Gln Lys Val Ile Val Tyr Xaa Val Asn Asn
         35                  40                  45

Leu Glu Glu Ile Cys Gln Leu Ile Ile Gln Ala Phe Glu Ala Gly Ile
 50                  55                  60

Asp Phe Gln Glu Leu Ala Asp Ser Phe Leu Leu Met Leu Cys Leu His
 65                  70                  75                  80

His Gln Tyr Gln Gly Asp Tyr Lys Leu Phe Leu Glu Ser Xaa Ala Val
             85                  90                  95

Lys Tyr Leu Glu Gly His Gly Phe Arg Phe Glu Val Lys Lys Arg Asp
            100                 105                 110

Gly Val Xaa Arg Leu Glu Glu Leu Pro Ala Val Ser Ser Gly Lys
         115                 120                 125

Asn Ile Lys Arg Thr Leu Ala Ala Leu Pro Glu Glu Glu Thr Thr Glu
130                 135                 140

Ala Asn Ala Gly Gln Phe Leu Ser Phe Ala Ser Leu Phe Leu Pro Lys
145                 150                 155                 160

Leu Val Val Gly Glu Lys Ala Cys Leu Glu Lys Val Gln Arg Gln Ile
                165                 170                 175

Gln Val His Ala Glu Gln Gly Leu Ile Gln Tyr Pro Thr Ala Trp Gln
            180                 185                 190

Ser Val Gly His Met Met Val Ile Phe Arg Leu Met Arg Thr Asn Phe
        195                 200                 205

Leu Ile Lys Phe Leu Leu Ile His Gln Asp Ala Asn Asp Ala Val Ile
210                 215                 220

Ser Asn Ser Val Ala Gln Ala Arg Phe Ser Gly Leu Leu Ile Val Lys
225                 230                 235                 240

Thr Val Leu Asp His Ile Leu Gln Lys Thr Asp Xaa Gly Val Thr Leu
                245                 250                 255

His Pro Leu Ala Arg Thr Ala Lys Val Lys Asn Glu Val Asn Ser Phe
            260                 265                 270

Lys Ala Ala Leu Ser Ser Leu Ala Lys His Gly Glu Tyr Ala Pro Phe
        275                 280                 285

Ala Arg Leu Leu Asn Leu Ser Gly Val Asn Asn Leu Glu His Gly Leu
290                 295                 300

Tyr Pro Gln Leu Ser Ala Ile Ala Leu Gly Val Ala Thr Ala His Gly
305                 310                 315                 320

Ser Thr Leu Ala Gly Val Asn Val Gly Glu Gln Tyr Gln Gln Leu Arg
                325                 330                 335

Glu Ala Ala Thr Glu Ala Glu Lys Gln Leu Gln Gln Tyr Ala Glu Ser
            340                 345                 350

Arg Glu Leu Asp Xaa Leu Gly Leu Asp Asp Gln Glu Lys Lys Ile Leu
```

```
            355                 360                 365
Met Asn Phe His Gln Lys Lys Asn
    370                 375

<210> SEQ ID NO 19
<211> LENGTH: 40
<212> TYPE: PRT
<213> ORGANISM: Sendai virus

<400> SEQUENCE: 19

Tyr Leu Ser Lys Gly Pro Arg Ala Pro Phe Ile Cys Ile Leu Lys Asp
1               5                   10                  15

Pro Val His Gly Glu Phe Ala Pro Gly Asn Tyr Pro Ala Leu Trp Ser
            20                  25                  30

Tyr Ala Met Gly Val Ala Val Val
        35                  40

<210> SEQ ID NO 20
<211> LENGTH: 40
<212> TYPE: PRT
<213> ORGANISM: Mumps virus

<400> SEQUENCE: 20

Tyr Arg Gly Leu Gly Glu Gln Ala Arg Tyr Leu Ala Leu Leu Glu Ala
1               5                   10                  15

Pro Gln Ile Met Asp Phe Ala Pro Gly Gly Tyr Pro Leu Ile Phe Ser
            20                  25                  30

Tyr Ala Met Gly Val Gly Thr Val
        35                  40

<210> SEQ ID NO 21
<211> LENGTH: 40
<212> TYPE: PRT
<213> ORGANISM: Human respirotory syncitial virus

<400> SEQUENCE: 21

Ala Gln Lys Leu Gly Gly Glu Ala Gly Phe Tyr His Ile Leu Asn Asn
1               5                   10                  15

Pro Lys Ala Ser Leu Leu Ser Leu Thr Gln Phe Pro Asn Phe Ser Ser
            20                  25                  30

Val Val Leu Gly Asn Ala Ala Gly
        35                  40

<210> SEQ ID NO 22
<211> LENGTH: 40
<212> TYPE: PRT
<213> ORGANISM: Artificial Sequence
<220> FEATURE:
<223> OTHER INFORMATION: Consensus sequence

<400> SEQUENCE: 22

Leu Ala Lys His Gly Glu Tyr Ala Pro Phe Ala Arg Leu Leu Asn Leu
1               5                   10                  15

Ser Gly Val Asn Asn Leu Glu His Gly Leu Tyr Pro Gln Leu Ser Ala
            20                  25                  30

Ile Ala Leu Gly Val Ala Thr Ala
        35                  40

<210> SEQ ID NO 23
<211> LENGTH: 752
<212> TYPE: PRT
```

<213> ORGANISM: Homo sapiens

<400> SEQUENCE: 23

```
Met Ala Glu Pro Arg Gln Glu Phe Asp Thr Met Glu Asp Gln Ala Gly
1               5                   10                  15
Asp Tyr Thr Met Leu Gln Asp Gln Glu Gly Asp Met Asp His Gly Leu
            20                  25                  30
Lys Glu Ser Pro Pro Gln Pro Pro Ala Asp Asp Gly Ser Glu Glu Pro
        35                  40                  45
Gly Ser Glu Thr Ser Asp Ala Lys Ser Thr Pro Thr Ala Glu Asp Val
50                  55                  60
Thr Ala Pro Leu Val Glu Glu Arg Ala Pro Asp Lys Gln Ala Thr Ala
65                  70                  75                  80
Gln Ser His Thr Glu Ile Pro Glu Gly Thr Thr Ala Glu Glu Ala Gly
            85                  90                  95
Ile Gly Asp Thr Pro Asn Met Glu Asp Gln Ala Ala Gly His Val Thr
            100                 105                 110
Gln Glu Pro Gln Lys Val Glu Ile Phe Ser Gln Ser Leu Leu Val Glu
        115                 120                 125
Pro Gly Arg Arg Glu Gly Gln Ala Pro Asp Ser Gly Ile Ser Asp Trp
130                 135                 140
Thr His Gln Gln Val Pro Ser Met Ser Gly Ala Pro Leu Pro Pro Gln
145                 150                 155                 160
Gly Leu Arg Glu Ala Thr His Gln Pro Leu Gly Thr Arg Pro Glu Asp
            165                 170                 175
Val Glu Arg Ser His Pro Ala Ser Glu Leu Leu Trp Gln Glu Ser Pro
            180                 185                 190
Gln Lys Glu Ala Trp Gly Lys Asp Arg Leu Gly Ser Glu Glu Glu Val
        195                 200                 205
Asp Glu Asp Ile Thr Met Asp Glu Ser Ser Gln Glu Ser Pro Pro Ser
210                 215                 220
Gln Ala Ser Leu Ala Pro Gly Thr Ala Thr Pro Gln Ala Arg Ser Val
225                 230                 235                 240
Ser Ala Ser Gly Val Ser Gly Glu Thr Thr Ser Ile Pro Gly Phe Pro
            245                 250                 255
Ala Glu Gly Ser Ile Pro Leu Pro Ala Asp Phe Phe Ser Lys Val Ser
            260                 265                 270
Ala Glu Thr Gln Ala Ser Pro Pro Glu Gly Pro Gly Thr Gly Pro Ser
        275                 280                 285
Glu Glu Gly His Glu Ala Ala Pro Glu Phe Thr Phe His Val Glu Ile
290                 295                 300
Lys Ala Ser Ala Pro Lys Glu Gln Asp Leu Glu Gly Ala Thr Val Val
305                 310                 315                 320
Gly Ala Pro Ala Glu Glu Gln Lys Ala Arg Gly Pro Ser Val Gly Lys
            325                 330                 335
Gly Thr Lys Glu Ala Ser Leu Leu Glu Pro Thr Asp Lys Gln Pro Ala
            340                 345                 350
Ala Gly Leu Pro Gly Arg Pro Val Ser Arg Val Pro Gln Leu Lys Ala
        355                 360                 365
Arg Val Ala Gly Val Ser Lys Asp Arg Thr Gly Asn Asp Glu Lys Lys
370                 375                 380
Ala Lys Thr Ser Thr Pro Ser Cys Ala Lys Thr Pro Ser Asn Arg Pro
385                 390                 395                 400
```

```
Cys Leu Ser Pro Thr Arg Pro Thr Pro Gly Ser Ser Asp Pro Leu Ile
                405                 410                 415
Lys Pro Ser Ser Pro Ala Val Cys Pro Glu Pro Ala Thr Ser Pro Lys
            420                 425                 430
Tyr Val Ser Ser Val Thr Pro Arg Asn Gly Ser Pro Gly Thr Lys Gln
        435                 440                 445
Met Lys Leu Lys Gly Ala Asp Gly Lys Thr Gly Ala Lys Ile Ala Thr
    450                 455                 460
Pro Arg Gly Ala Ala Thr Pro Gly Gln Lys Gly Thr Ser Asn Ala Thr
465                 470                 475                 480
Arg Ile Pro Ala Lys Thr Thr Pro Ser Pro Lys Thr Pro Pro Gly Ser
                485                 490                 495
Gly Glu Pro Pro Lys Ser Gly Glu Arg Ser Gly Tyr Ser Ser Pro Gly
            500                 505                 510
Ser Pro Gly Thr Pro Gly Ser Arg Ser Arg Thr Pro Ser Leu Pro Thr
        515                 520                 525
Pro Pro Thr Arg Glu Pro Lys Lys Val Ala Val Val Arg Thr Pro Pro
530                 535                 540
Lys Ser Pro Ser Ala Ser Lys Ser Arg Leu Gln Thr Ala Pro Val Pro
545                 550                 555                 560
Met Pro Asp Leu Lys Asn Val Arg Ser Lys Ile Gly Ser Thr Glu Asn
                565                 570                 575
Leu Lys His Gln Pro Gly Gly Gly Lys Val Gln Ile Ile Asn Lys Lys
            580                 585                 590
Leu Asp Leu Ser Asn Val Gln Ser Lys Cys Gly Ser Lys Asp Asn Ile
        595                 600                 605
Lys His Val Pro Gly Gly Gly Ser Val His Ile Val Tyr Lys Pro Val
    610                 615                 620
Asp Leu Ser Lys Val Thr Ser Lys Cys Gly Ser Leu Gly Asn Ile His
625                 630                 635                 640
His Lys Pro Gly Gly Gly Gln Val Glu Val Lys Ser Glu Lys Leu Asp
                645                 650                 655
Phe Lys Asp Arg Val Gln Ser Lys Ile Gly Ser Leu Asp Asn Ile Thr
            660                 665                 670
His Val Pro Gly Gly Gly Asn Lys Lys Ile Glu Thr His Lys Leu Thr
        675                 680                 685
Phe Arg Glu Asn Ala Lys Ala Lys Thr Asp His Gly Ala Glu Ile Val
    690                 695                 700
Tyr Lys Ser Pro Val Val Ser Gly Asp Thr Ser Pro Arg His Leu Ser
705                 710                 715                 720
Asn Val Ser Ser Thr Gly Ser Ile Asp Met Val Asp Ser Pro Gln Leu
                725                 730                 735
Ala Thr Leu Ala Asp Glu Val Ser Ala Ser Leu Ala Lys Gln Gly Leu
            740                 745                 750

<210> SEQ ID NO 24
<211> LENGTH: 758
<212> TYPE: PRT
<213> ORGANISM: Homo sapiens

<400> SEQUENCE: 24

Met Ala Glu Pro Arg Gln Glu Phe Glu Val Met Glu Asp His Ala Gly
1               5                   10                  15
Thr Tyr Gly Leu Gly Asp Arg Lys Asp Gln Gly Gly Tyr Thr Met His
            20                  25                  30
```

-continued

```
Gln Asp Gln Glu Gly Asp Thr Asp Ala Gly Leu Lys Glu Ser Pro Leu
         35                  40                  45
Gln Thr Pro Thr Glu Asp Gly Ser Glu Glu Pro Gly Ser Glu Thr Ser
     50                  55                  60
Asp Ala Lys Ser Thr Pro Thr Ala Glu Asp Val Thr Ala Pro Leu Val
 65                  70                  75                  80
Asp Glu Gly Ala Pro Gly Lys Gln Ala Ala Gln Pro His Thr Glu
                 85                  90                  95
Ile Pro Glu Gly Thr Thr Ala Glu Glu Ala Gly Ile Gly Asp Thr Pro
                100                 105                 110
Ser Leu Glu Asp Glu Ala Ala Gly His Val Thr Gln Glu Pro Glu Ser
            115                 120                 125
Gly Lys Val Val Gln Glu Gly Phe Leu Arg Glu Pro Gly Pro Pro Gly
        130                 135                 140
Leu Ser His Gln Leu Met Ser Gly Met Pro Gly Ala Pro Leu Leu Pro
145                 150                 155                 160
Glu Gly Pro Arg Glu Ala Thr Arg Gln Pro Ser Gly Thr Gly Pro Glu
                165                 170                 175
Asp Thr Glu Gly Gly Arg His Ala Pro Glu Leu Leu Lys His Gln Leu
            180                 185                 190
Leu Gly Asp Leu His Gln Glu Gly Pro Pro Leu Lys Gly Ala Gly Gly
        195                 200                 205
Lys Glu Arg Pro Gly Ser Lys Glu Glu Val Asp Glu Asp Arg Asp Val
    210                 215                 220
Asp Glu Ser Ser Pro Gln Asp Ser Pro Pro Ser Lys Ala Ser Pro Ala
225                 230                 235                 240
Gln Asp Gly Arg Pro Pro Gln Thr Ala Ala Arg Glu Ala Thr Ser Ile
                245                 250                 255
Pro Gly Phe Pro Ala Glu Gly Ala Ile Pro Leu Pro Val Asp Phe Leu
            260                 265                 270
Ser Lys Val Ser Thr Glu Ile Pro Ala Ser Glu Pro Asp Gly Pro Ser
        275                 280                 285
Val Gly Arg Ala Lys Gly Gln Asp Ala Pro Leu Glu Phe Thr Phe His
    290                 295                 300
Val Glu Ile Thr Pro Asn Val Gln Lys Glu Gln Ala His Ser Glu Glu
305                 310                 315                 320
His Leu Gly Arg Ala Ala Phe Pro Gly Ala Pro Gly Glu Gly Pro Glu
                325                 330                 335
Ala Arg Gly Pro Ser Leu Gly Glu Asp Thr Lys Glu Ala Asp Leu Pro
            340                 345                 350
Glu Pro Ser Glu Lys Gln Pro Ala Ala Ala Pro Arg Gly Lys Pro Val
        355                 360                 365
Ser Arg Val Pro Gln Leu Lys Ala Arg Met Val Ser Lys Ser Lys Asp
    370                 375                 380
Gly Thr Gly Ser Asp Asp Lys Lys Ala Lys Thr Ser Thr Arg Ser Ser
385                 390                 395                 400
Ala Lys Thr Leu Lys Asn Arg Pro Cys Leu Ser Pro Lys Leu Pro Thr
                405                 410                 415
Pro Gly Ser Ser Asp Pro Leu Ile Gln Pro Ser Ser Pro Ala Val Cys
            420                 425                 430
Pro Glu Pro Pro Ser Ser Pro Lys His Val Ser Val Thr Ser Arg
        435                 440                 445
```

```
Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Glu Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755

<210> SEQ ID NO 25
<211> LENGTH: 733
<212> TYPE: PRT
<213> ORGANISM: Homo sapiens

<400> SEQUENCE: 25

Met Ala Asp Pro Arg Gln Glu Phe Asp Thr Met Glu Asp His Ala Gly
 1               5                  10                  15

Asp Tyr Thr Leu Leu Gln Asp Gln Glu Gly Asp Met Asp His Gly Leu
            20                  25                  30

Lys Glu Ser Pro Pro Gln Pro Pro Ala Asp Asp Gly Ala Glu Glu Pro
        35                  40                  45

Gly Ser Glu Thr Ser Asp Ala Lys Ser Thr Pro Thr Ala Glu Asp Val
    50                  55                  60
```

-continued

```
Thr Ala Pro Leu Val Asp Glu Arg Ala Pro Asp Lys Gln Ala Ala
 65                  70                  75                  80

Gln Pro His Thr Glu Ile Pro Glu Gly Ile Thr Ala Glu Ala Gly
             85                  90                  95

Ile Gly Asp Thr Pro Asn Gln Glu Asp Gln Ala Ala Gly His Val Thr
            100                 105                 110

Gln Gly Arg Arg Glu Gly Gln Ala Pro Asp Leu Gly Thr Ser Asp Trp
            115                 120                 125

Thr Arg Gln Gln Val Ser Ser Met Ser Gly Ala Pro Leu Leu Pro Gln
130                 135                 140

Gly Leu Arg Glu Ala Thr Cys Gln Pro Ser Gly Thr Arg Pro Glu Asp
145                 150                 155                 160

Ile Glu Lys Ser His Pro Ala Ser Glu Leu Leu Arg Arg Gly Pro Pro
                165                 170                 175

Gln Lys Glu Gly Trp Gly Gln Asp Arg Leu Gly Ser Glu Glu Val
            180                 185                 190

Asp Glu Asp Leu Thr Val Asp Glu Ser Ser Gln Asp Ser Pro Pro Ser
            195                 200                 205

Gln Ala Ser Leu Thr Pro Gly Arg Ala Ala Pro Gln Ala Gly Ser Gly
210                 215                 220

Ser Val Cys Gly Glu Thr Ala Ser Val Pro Gly Leu Pro Thr Glu Gly
225                 230                 235                 240

Ser Val Pro Leu Pro Ala Asp Phe Phe Ser Lys Val Ser Ala Glu Thr
                245                 250                 255

Gln Ala Ser Gln Pro Glu Gly Pro Gly Thr Gly Pro Met Glu Glu Gly
            260                 265                 270

His Glu Ala Ala Pro Glu Phe Thr Phe His Val Glu Ile Lys Ala Ser
            275                 280                 285

Thr Pro Lys Glu Gln Asp Leu Glu Gly Ala Thr Val Val Gly Val Pro
290                 295                 300

Gly Glu Glu Gln Lys Ala Gln Thr Gln Gly Pro Ser Val Gly Lys Gly
305                 310                 315                 320

Thr Lys Glu Ala Ser Leu Gln Glu Pro Pro Gly Lys Gln Pro Ala Ala
                325                 330                 335

Gly Leu Pro Gly Arg Pro Val Ser Arg Val Pro Gln Leu Lys Ala Arg
            340                 345                 350

Val Ala Ser Lys Asp Arg Thr Gly Asn Asp Glu Lys Lys Ala Lys Thr
            355                 360                 365

Ser Thr Pro Ser Cys Ala Lys Ala Pro Ser His Arg Pro Cys Leu Ser
370                 375                 380

Pro Thr Arg Pro Thr Leu Gly Ser Ser Asp Pro Leu Ile Lys Pro Ser
385                 390                 395                 400

Ser Pro Ala Val Ser Pro Glu Pro Ala Thr Ser Pro Lys His Val Ser
                405                 410                 415

Ser Val Thr Pro Arg Asn Gly Ser Pro Gly Thr Lys Gln Met Lys Leu
            420                 425                 430

Lys Gly Ala Asp Gly Lys Thr Gly Ala Lys Ile Ala Thr Pro Arg Gly
            435                 440                 445

Ala Ala Ser Pro Ala Gln Lys Gly Thr Ser Asn Ala Thr Arg Ile Pro
450                 455                 460

Ala Lys Thr Thr Pro Ser Pro Lys Thr Pro Pro Gly Ser Gly Glu Pro
465                 470                 475                 480
```

```
Pro Lys Ser Gly Glu Arg Ser Gly Tyr Ser Ser Pro Gly Ser Pro Gly
            485                 490                 495

Thr Pro Gly Ser Arg Ser Arg Thr Pro Ser Leu Pro Thr Pro Pro Thr
        500                 505                 510

Arg Glu Pro Lys Lys Val Ala Val Val Arg Thr Pro Lys Ser Pro
    515                 520                 525

Ser Ala Ser Lys Ser Arg Leu Gln Thr Ala Pro Val Pro Met Pro Asp
530                 535                 540

Leu Lys Asn Val Arg Ser Lys Ile Gly Ser Thr Glu Asn Leu Lys His
545                 550                 555                 560

Gln Pro Gly Gly Gly Lys Val Gln Ile Ile Asn Lys Lys Leu Asp Leu
                565                 570                 575

Ser Asn Val Gln Ser Lys Cys Gly Ser Lys Asp Asn Ile Lys His Val
                580                 585                 590

Pro Gly Gly Gly Ser Val Gln Ile Val Tyr Lys Pro Val Asp Leu Ser
            595                 600                 605

Lys Val Thr Ser Lys Cys Gly Ser Leu Gly Asn Ile His His Lys Pro
        610                 615                 620

Gly Gly Gly Gln Val Glu Val Lys Ser Glu Lys Leu Asp Phe Lys Asp
625                 630                 635                 640

Arg Val Gln Ser Lys Ile Gly Ser Leu Asp Asn Ile Thr His Val Pro
                645                 650                 655

Gly Gly Gly Asn Lys Lys Ile Glu Thr His Lys Leu Thr Phe Arg Glu
            660                 665                 670

Asn Ala Lys Ala Lys Thr Asp His Gly Ala Glu Ile Val Tyr Lys Ser
        675                 680                 685

Pro Val Val Ser Gly Asp Thr Ser Pro Arg His Leu Ser Asn Val Ser
690                 695                 700

Ser Thr Gly Ser Ile Asp Met Val Asp Ser Pro Gln Leu Ala Thr Leu
705                 710                 715                 720

Ala Asp Glu Val Ser Ala Ser Leu Ala Lys Gln Gly Leu
                725                 730

<210> SEQ ID NO 26
<211> LENGTH: 448
<212> TYPE: PRT
<213> ORGANISM: Bos taurus

<400> SEQUENCE: 26

Met Ala Glu Pro Arg Gln Glu Phe Asp Val Met Glu Asp His Ala Gln
1               5                   10                  15

Gly Asp Tyr Thr Leu Gln Asp Gln Glu Gly Asp Met Asp Pro Gly Leu
            20                  25                  30

Lys Glu Ser Pro Leu Gln Thr Pro Ala Asp Asp Gly Ser Glu Glu Pro
        35                  40                  45

Gly Ser Glu Thr Ser Asp Ala Lys Ser Thr Pro Thr Ala Glu Asp Ala
    50                  55                  60

Thr Ala Pro Leu Val Asp Glu Gly Ala Pro Gly Glu Gln Ala Ala Ala
65                  70                  75                  80

Gln Ala Pro Ala Glu Ile Pro Glu Gly Thr Ala Ala Glu Glu Ala Gly
                85                  90                  95

Ile Gly Asp Thr Ser Asn Leu Glu Asp Gln Ala Ala Gly His Val Thr
            100                 105                 110

Gln Ala Arg Met Val Ser Lys Gly Lys Asp Gly Thr Gly Pro Asp Asp
        115                 120                 125
```

```
Lys Lys Thr Lys Gly Ala Asp Gly Lys Pro Gly Thr Lys Ile Ala Thr
            130                 135                 140

Pro Arg Gly Ala Ala Pro Gly Gln Lys Gly Gln Ala Asn Ala Thr
145                 150                 155                 160

Arg Ile Pro Ala Lys Thr Thr Pro Thr Pro Lys Thr Ser Pro Ala Thr
                165                 170                 175

Met Gln Val Gln Lys Lys Pro Pro Ala Gly Ala Lys Ser Glu Arg
            180                 185                 190

Gly Glu Ser Gly Lys Ser Gly Asp Arg Ser Gly Tyr Ser Ser Pro Gly
                195                 200                 205

Ser Pro Gly Thr Pro Gly Ser Arg Ser Arg Thr Pro Ser Leu Pro Thr
            210                 215                 220

Pro Pro Thr Arg Glu Pro Lys Lys Val Ala Val Arg Thr Pro Pro
225                 230                 235                 240

Lys Ser Pro Ser Ala Ala Lys Ser Arg Leu Gln Ala Ala Pro Gly Pro
                245                 250                 255

Met Pro Asp Leu Lys Asn Val Lys Ser Lys Ile Gly Ser Thr Glu Asn
            260                 265                 270

Leu Lys His Gln Pro Gly Gly Gly Lys Val Gln Ile Ile Asn Lys Lys
            275                 280                 285

Leu Asp Leu Ser Asn Val Gln Ser Lys Cys Gly Ser Lys Asp Asn Ile
            290                 295                 300

Lys His Val Pro Gly Gly Gly Ser Val Gln Ile Val Tyr Lys Pro Val
305                 310                 315                 320

Asp Leu Ser Lys Val Thr Ser Lys Cys Gly Ser Leu Gly Asn Ile His
                325                 330                 335

His Lys Pro Gly Gly Gly Gln Val Glu Val Lys Ser Glu Lys Leu Asp
            340                 345                 350

Phe Lys Asp Arg Val Gln Ser Lys Ile Gly Ser Leu Asp Asn Ile Thr
            355                 360                 365

His Val Pro Gly Gly Gly Asn Lys Lys Ile Glu Thr His Lys Leu Thr
            370                 375                 380

Phe Arg Glu Asn Ala Lys Ala Lys Thr Asp His Gly Ala Glu Ile Val
385                 390                 395                 400

Tyr Lys Ser Pro Val Val Ser Gly Asp Thr Ser Pro Arg His Leu Ser
                405                 410                 415

Asn Val Ser Ser Thr Gly Ser Ile Asp Met Val Asp Ser Pro Gln Leu
            420                 425                 430

Ala Thr Leu Ala Asp Glu Val Ser Ala Ser Leu Ala Lys Gln Gly Leu
            435                 440                 445

<210> SEQ ID NO 27
<211> LENGTH: 352
<212> TYPE: PRT
<213> ORGANISM: Homo sapiens

<400> SEQUENCE: 27

Met Ala Glu Pro Arg Gln Glu Phe Glu Val Met Glu Asp His Ala Gly
  1               5                  10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
```

-continued

```
                50                  55                  60
Thr Gln Ala Arg Met Val Ser Lys Ser Lys Asp Gly Thr Gly Ser Asp
 65                  70                  75                  80

Asp Lys Lys Ala Lys Gly Ala Asp Gly Lys Thr Lys Ile Ala Thr Pro
                 85                  90                  95

Arg Gly Ala Ala Pro Pro Gly Gln Lys Gly Gln Ala Asn Ala Thr Arg
                100                 105                 110

Ile Pro Ala Lys Thr Pro Pro Ala Pro Lys Thr Pro Pro Ser Ser Gly
                115                 120                 125

Glu Pro Pro Lys Ser Gly Asp Arg Ser Gly Tyr Ser Ser Pro Gly Ser
            130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
                180                 185                 190

Pro Asp Leu Lys Asn Val Lys Ser Lys Ile Gly Ser Thr Glu Asn Leu
                195                 200                 205

Lys His Gln Pro Gly Gly Gly Lys Val Gln Ile Val Tyr Lys Pro Val
            210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
                260                 265                 270

His Val Pro Gly Gly Gly Asn Lys Lys Ile Glu Thr His Lys Leu Thr
                275                 280                 285

Phe Arg Glu Asn Ala Lys Ala Lys Thr Asp His Gly Ala Glu Ile Val
            290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                325                 330                 335

Ala Thr Leu Ala Asp Glu Val Ser Ala Ser Leu Ala Lys Gln Gly Leu
                340                 345                 350

<210> SEQ ID NO 28
<211> LENGTH: 764
<212> TYPE: PRT
<213> ORGANISM: Ebola virus

<400> SEQUENCE: 28

Met Asp Ser Arg Pro Gln Lys Ile Trp Met Ala Pro Ser Leu Thr Glu
  1               5                  10                  15

Ser Asp Met Asp Tyr His Lys Ile Leu Thr Ala Gly Leu Ser Val Gln
                 20                  25                  30

Gln Gly Ile Val Arg Gln Arg Val Ile Pro Val Tyr Gln Val Asn Asn
             35                  40                  45

Leu Glu Glu Ile Cys Gln Leu Ile Ile Gln Ala Phe Glu Ala Gly Val
             50                  55                  60

Asp Phe Gln Glu Ser Ala Asp Ser Phe Leu Leu Met Leu Cys Leu His
 65                  70                  75                  80
```

-continued

```
His Ala Tyr Gln Gly Asp Tyr Lys Leu Phe Leu Glu Ser Gly Ala Val
                85                  90                  95
Lys Tyr Leu Glu Gly His Gly Phe Arg Phe Glu Val Lys Lys Arg Asp
            100                 105                 110
Gly Val Lys Arg Leu Glu Glu Leu Leu Pro Ala Val Ser Ser Gly Lys
        115                 120                 125
Asn Ile Lys Arg Thr Leu Ala Ala Met Pro Glu Glu Thr Thr Glu
    130                 135                 140
Ala Asn Ala Gly Gln Phe Leu Ser Phe Ala Ser Leu Phe Leu Pro Lys
145                 150                 155                 160
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ala Trp Gln
            180                 185                 190
Ser Val Gly His Met Met Val Ile Phe Arg Leu Met Arg Thr Asn Phe
        195                 200                 205
Leu Ile Lys Phe Leu Leu Ile His Gln Gly Met His Met Val Ala Gly
    210                 215                 220
His Asp Ala Asn Asp Ala Val Ile Ser Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Glu Arg Gly Val Arg Leu His Pro Leu Ala Arg Thr Ala Lys
            260                 265                 270
Val Lys Asn Glu Val Asn Ser Phe Lys Ala Ala Leu Ser Ser Leu Ala
        275                 280                 285
Lys His Gly Glu Tyr Ala Pro Phe Ala Arg Leu Leu Asn Leu Ser Gly
    290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
            340                 345                 350
Gln Leu Gln Gln Tyr Ala Glu Ser Arg Glu Leu Asp His Leu Gly Leu
        355                 360                 365
Asp Asp Gln Glu Lys Lys Ile Leu Met Asn Phe His Gln Lys Lys Asn
    370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
                405                 410                 415
Thr Ser Gly His Tyr Asp Asp Asp Asp Ile Pro Phe Pro Gly Pro
            420                 425                 430
Ile Asn Asp Asp Asp Asn Pro Gly His Gln Asp Asp Pro Thr Asp
        435                 440                 445
Ser Gln Asp Thr Thr Ile Pro Asp Val Val Asp Pro Asp Asp Gly
    450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Glu Asp Thr Lys
                485                 490                 495
Pro Val Pro Asn Arg Ser Thr Lys Gly Gly Gln Gln Lys Asn Ser Gln
```

```
                500             505             510
Lys Gly Gln His Ile Glu Gly Arg Gln Thr Gln Ser Arg Pro Ile Gln
            515                 520                 525
Asn Val Pro Gly Pro His Arg Thr Ile His His Ala Ser Ala Pro Leu
        530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
                565                 570                 575
Asp Glu Thr Ser Ser Leu Pro Pro Leu Glu Ser Asp Asp Glu Glu Gln
            580                 585                 590
Asp Arg Asp Gly Thr Ser Asn Arg Thr Pro Thr Val Ala Pro Pro Ala
        595                 600                 605
Pro Val Tyr Arg Asp His Ser Glu Lys Lys Glu Leu Pro Gln Asp Glu
        610                 615                 620
Gln Gln Asp Gln Asp His Thr Gln Glu Ala Arg Asn Gln Asp Ser Asp
625                 630                 635                 640
Asn Thr Gln Ser Glu His Ser Phe Glu Glu Met Tyr Arg His Ile Leu
                645                 650                 655
Arg Ser Gln Gly Pro Phe Asp Ala Val Leu Tyr Tyr His Met Met Lys
            660                 665                 670
Asp Glu Pro Val Val Phe Ser Thr Ser Asp Gly Lys Glu Tyr Thr Tyr
        675                 680                 685
Pro Asp Ser Leu Glu Glu Glu Tyr Pro Pro Trp Leu Thr Glu Lys Glu
        690                 695                 700
Ala Met Asn Glu Glu Asn Arg Phe Val Thr Leu Asp Gly Gln Gln Phe
705                 710                 715                 720
Tyr Trp Pro Val Met Asn His Lys Asn Lys Phe Met Ala Ile Leu Gln
                725                 730                 735
His His Gln Gly Pro Phe Glu Gln Lys Leu Ile Ser Glu Glu Asp Leu
            740                 745                 750
Asn Met His Thr Gly His His His His His Arg
        755                 760

<210> SEQ ID NO 29
<211> LENGTH: 635
<212> TYPE: PRT
<213> ORGANISM: Artificial Sequence
<220> FEATURE:
<223> OTHER INFORMATION: Consensus sequence

<400> SEQUENCE: 29

Met Ala Glu Pro Arg Gln Glu Phe Asp Val Met Glu Asp His Ala Gly
  1               5                  10                  15
Thr Asp Tyr Thr Met Leu Gln Asp Gln Glu Gly Asp Met Asp Gly Leu
             20                  25                  30
Lys Glu Ser Pro Leu Gln Pro Pro Ala Asp Asp Gly Ser Glu Glu Pro
         35                  40                  45
Gly Ser Glu Thr Ser Asp Ala Lys Ser Thr Pro Thr Ala Glu Asp Val
     50                  55                  60
Thr Ala Pro Leu Val Asp Glu Ala Pro Lys Gln Ala Ala Ala Gln His
 65                  70                  75                  80
Thr Glu Ile Pro Glu Gly Thr Thr Ala Glu Glu Ala Gly Ile Gly Asp
                 85                  90                  95
Thr Pro Asn Leu Glu Asp Gln Ala Ala Gly His Val Thr Gln Arg Glu
```

-continued

```
                100                 105                 110
Gly Pro Asp Gly Ser Asp Thr Gln Gln Val Ser Met Ser Gly Ala Pro
            115                 120                 125
Leu Pro Gly Leu Arg Glu Ala Thr Gln Pro Gly Thr Arg Pro Glu Asp
        130                 135                 140
Val Glu Ala Glu Leu Leu Pro Lys Ala Gly Asp Arg Leu Gly Ser Glu
145                 150                 155                 160
Glu Val Asp Glu Asp Leu Val Asp Glu Ser Gln Asp Ser Pro Pro
                165                 170                 175
Ser Ala Ser Ala Pro Gln Ala Ser Val Glu Ser Ile Pro Gly Pro Glu
            180                 185                 190
Gly Ser Ile Pro Leu Pro Asp Phe Ser Lys Val Ser Glu Gln Ala Ser
        195                 200                 205
Pro Glu Gly Pro Gly Glu Gly Glu Ala Ala Glu Phe Thr Phe His Val
    210                 215                 220
Glu Ile Lys Glu Gln Leu Ala Thr Gly Ala Pro Gly Glu Ala Gly Pro
225                 230                 235                 240
Ser Val Gly Thr Lys Glu Ala Leu Glu Pro Lys Gln Pro Ala Ala Gly
                245                 250                 255
Leu Gly Arg Pro Val Ser Arg Val Pro Gln Leu Lys Ala Arg Met Val
            260                 265                 270
Ser Lys Ser Lys Asp Gly Thr Gly Asp Asp Lys Lys Ala Lys Thr Ser
        275                 280                 285
Thr Ser Ala Lys Arg Pro Cys Leu Ser Pro Thr Pro Thr Gly Ser Ser
    290                 295                 300
Asp Pro Leu Ile Lys Pro Ser Ser Pro Ala Val Pro Glu Pro Thr Ser
305                 310                 315                 320
Pro Lys His Val Ser Ser Val Thr Arg Gly Ser Gly Lys Met Lys Leu
                325                 330                 335
Lys Gly Ala Asp Gly Lys Thr Lys Ile Ala Thr Pro Arg Gly Ala Ala
            340                 345                 350
Pro Pro Gly Gln Lys Gly Gln Ala Asn Ala Thr Arg Ile Pro Ala Lys
        355                 360                 365
Thr Thr Pro Ala Pro Lys Thr Pro Ser Ser Gly Glu Pro Pro Lys
    370                 375                 380
Ser Gly Asp Arg Ser Gly Tyr Ser Ser Pro Gly Ser Pro Gly Thr Pro
385                 390                 395                 400
Gly Ser Arg Ser Arg Thr Pro Ser Leu Pro Thr Pro Pro Thr Arg Glu
                405                 410                 415
Pro Lys Lys Val Ala Val Val Arg Thr Pro Pro Lys Ser Pro Ser Ala
            420                 425                 430
Ala Lys Ser Arg Leu Gln Thr Ala Pro Val Pro Met Pro Asp Leu Lys
        435                 440                 445
Asn Val Lys Ser Lys Ile Gly Ser Thr Glu Asn Leu Lys His Gln Pro
    450                 455                 460
Gly Gly Gly Lys Val Gln Ile Ile Asn Lys Lys Leu Asp Leu Ser Asn
465                 470                 475                 480
Val Gln Ser Lys Cys Gly Ser Lys Asp Asn Ile Lys His Val Pro Gly
                485                 490                 495
Gly Gly Ser Val Gln Ile Val Tyr Lys Pro Val Asp Leu Ser Lys Val
            500                 505                 510
Thr Ser Lys Cys Gly Ser Leu Gly Asn Ile His His Lys Pro Gly Gly
        515                 520                 525
```

-continued

```
Gly Gln Val Glu Val Lys Ser Glu Lys Leu Asp Phe Lys Asp Arg Val
    530                 535                 540

Gln Ser Lys Ile Gly Ser Leu Asp Asn Ile Thr His Val Pro Gly Gly
545                 550                 555                 560

Gly Asn Lys Lys Ile Glu Thr His Lys Leu Thr Phe Arg Glu Asn Ala
                565                 570                 575

Lys Ala Lys Thr Asp His Gly Ala Glu Ile Val Tyr Lys Ser Pro Val
            580                 585                 590

Val Ser Gly Asp Thr Ser Pro Arg His Leu Ser Asn Val Ser Ser Thr
        595                 600                 605

Gly Ser Ile Asp Met Val Asp Ser Pro Gln Leu Ala Thr Leu Ala Asp
    610                 615                 620

Glu Val Ser Ala Ser Leu Ala Lys Gln Gly Leu
625                 630                 635
```